US007807815B2

(12) United States Patent
MacLachlan et al.

(10) Patent No.: US 7,807,815 B2
(45) Date of Patent: *Oct. 5, 2010

(54) COMPOSITIONS COMPRISING IMMUNOSTIMULATORY SIRNA MOLECULES AND DLINDMA OR DLENDMA

(75) Inventors: Ian MacLachlan, Mission (CA); Adam Judge, Vancouver (CA); James Heyes, Burnaby (CA); Lorne Palmer, Vancouver (CA)

(73) Assignee: Protiva Biotherapeutics, Inc., Burnaby, BC (CA)

( * ) Notice: Subject to any disclaimer, the term of this patent is extended or adjusted under 35 U.S.C. 154(b) by 263 days.

This patent is subject to a terminal disclaimer.

(21) Appl. No.: 11/174,453

(22) Filed: Jun. 30, 2005

(65) Prior Publication Data

US 2006/0025366 A1 Feb. 2, 2006

Related U.S. Application Data

(60) Provisional application No. 60/665,297, filed on Mar. 25, 2005, provisional application No. 60/627,326, filed on Nov. 12, 2004, provisional application No. 60/589,363, filed on Jul. 19, 2004, provisional application No. 60/585,301, filed on Jul. 2, 2004.

(51) Int. Cl.
*C07H 21/04* (2006.01)
(52) U.S. Cl. .................................... 536/24.5
(58) Field of Classification Search ................ 536/24.5
See application file for complete search history.

(56) References Cited

U.S. PATENT DOCUMENTS

| 4,394,448 | A | 7/1983 | Szoka, Jr. et al. |
| 4,438,052 | A | 3/1984 | Weder et al. |
| 4,515,736 | A | 5/1985 | Deamer |
| 4,598,051 | A | 7/1986 | Papahadjopoulos et al. |
| 4,897,355 | A | 1/1990 | Eppstein et al. |
| 5,013,556 | A | 5/1991 | Woodle et al. |
| 5,171,678 | A | 12/1992 | Behr et al. |
| 5,208,036 | A | 5/1993 | Eppstein et al. |
| 5,225,212 | A | 7/1993 | Martin et al. |
| 5,264,618 | A | 11/1993 | Felgner et al. |
| 5,279,833 | A | 1/1994 | Rose |
| 5,283,185 | A | 2/1994 | Epand et al. |
| 5,320,906 | A | 6/1994 | Eley et al. |
| 5,545,412 | A | 8/1996 | Eppstein et al. |
| 5,578,475 | A | 11/1996 | Jessee et al. |
| 5,641,662 | A | 6/1997 | Debs et al. |
| 5,656,743 | A | 8/1997 | Busch et al. |
| 5,703,055 | A | 12/1997 | Felgner et al. |
| 5,705,385 | A | 1/1998 | Bally et al. |
| 5,820,873 | A | 10/1998 | Choi et al. |
| 5,976,567 | A | 11/1999 | Wheeler et al. |
| 5,981,501 | A | 11/1999 | Wheeler et al. |
| 6,534,484 | B1 | 3/2003 | Wheeler et al. |
| 6,586,410 | B1 | 7/2003 | Wheeler et al. |
| 6,649,780 | B1 | 11/2003 | Eibl et al. |
| 6,680,068 | B2* | 1/2004 | Campbell et al. ........... 424/450 |
| 6,815,432 | B2 | 11/2004 | Wheeler et al. |
| 6,858,224 | B2 | 2/2005 | Wheeler et al. |
| 7,341,738 | B2 | 3/2008 | Semple et al. |
| 2003/0073640 | A1* | 4/2003 | Beigelman et al. ........... 514/19 |
| 2003/0077829 | A1 | 4/2003 | MacLachlan |
| 2003/0125263 | A1 | 7/2003 | Gold et al. |
| 2003/0143732 | A1 | 7/2003 | Fosnaugh et al. |
| 2004/0063654 | A1 | 4/2004 | Davis et al. |
| 2004/0142892 | A1 | 7/2004 | Finn et al. |
| 2004/0192626 | A1 | 9/2004 | McSwiggen et al. |
| 2004/0198640 | A1 | 10/2004 | Leake et al. |
| 2004/0248299 | A1* | 12/2004 | Jayasena et al. ............. 435/455 |
| 2004/0253723 | A1 | 12/2004 | Tachas et al. |
| 2004/0259247 | A1 | 12/2004 | Tuschl et al. |
| 2005/0020525 | A1 | 1/2005 | McSwiggen et al. |
| 2005/0064595 | A1 | 3/2005 | MacLachlan et al. |
| 2005/0119214 | A1 | 6/2005 | Manoharan et al. |
| 2005/0282188 | A1 | 12/2005 | Haeberli et al. |
| 2006/0008910 | A1 | 1/2006 | MacLachlan et al. |
| 2006/0083780 | A1* | 4/2006 | Heyes et al. ................ 424/450 |
| 2006/0105976 | A1 | 5/2006 | Soutschek et al. |
| 2006/0240554 | A1 | 10/2006 | Chen et al. |
| 2007/0042983 | A1 | 2/2007 | Haeberli et al. |
| 2007/0135370 | A1 | 6/2007 | MacLachlan et al. |

FOREIGN PATENT DOCUMENTS

| CA | 2359180 A1 | 8/2000 |
| WO | WO 91/16024 A1 | 10/1991 |
| WO | WO 93/05162 A1 | 3/1993 |
| WO | WO 93/12240 A1 | 6/1993 |
| WO | WO 93/12756 A2 | 7/1993 |
| WO | WO 93/24640 A2 | 12/1993 |
| WO | WO 93/25673 A1 | 12/1993 |
| WO | WO 95/02698 A1 | 1/1995 |
| WO | WO 95/18863 A1 | 7/1995 |
| WO | WO 95/35301 A1 | 12/1995 |

(Continued)

OTHER PUBLICATIONS

Hamada, et al. (2002) Antisenseand Nucleic Acid Drug Development, v.12:301-9).*
Nguyen, et al. (2008) RNAI Therapeutics: An Update on Delivery. Current Opinion in Molecular Therapeutics, v.10(2):158-67.*
Aoki, H. et al. "Inhibition of motility and invasiveness of renal cell carcinoma induced by short interfering RNA transfection of β1, 4GalNAc transferase." *FEBS Letters* (2004), 567:203-208.
Dalby, B. et al. "Advanced transfection with Lipofectamine 2000 reagent: primary neurons, siRNA, and high-throughput applications" *Methods* (2004), 33(2):95-103.

(Continued)

*Primary Examiner*—J. E Angell
(74) *Attorney, Agent, or Firm*—Townsend and Townsend and Crew, LLP

(57) ABSTRACT

The present invention provides siRNA molecules and methods of using such siRNA molecules to modulate an immune response and to silence expression of a target gene.

28 Claims, 39 Drawing Sheets

FOREIGN PATENT DOCUMENTS

| | | |
|---|---|---|
| WO | WO 96/02655 A1 | 2/1996 |
| WO | WO 96/10390 A1 | 4/1996 |
| WO | WO 96/41873 A1 | 12/1996 |
| WO | WO 98/51278 A2 | 11/1998 |
| WO | WO 01/05374 A1 | 1/2001 |
| WO | WO 02/34236 A2 | 5/2002 |
| WO | WO 02/072068 A2 | 9/2002 |
| WO | WO 02/087541 A1 | 11/2002 |
| WO | WO 03/029453 | 4/2003 |
| WO | WO 03/086280 A2 | 10/2003 |
| WO | WO 03/097805 A2 | 11/2003 |
| WO | WO 2004/029212 A2 | 4/2004 |
| WO | WO 2004/046324 A2 | 6/2004 |
| WO | WO 2004/065546 A2 | 8/2004 |
| WO | WO 2004/110499 A1 | 12/2004 |
| WO | WO 2005/007196 A2 | 1/2005 |
| WO | WO 2005/019453 A3 | 3/2005 |
| WO | WO 2005/021044 | 3/2005 |
| WO | WO 2005/026372 A1 | 3/2005 |
| WO | WO 2005/044981 A3 | 5/2005 |
| WO | WO 2005/078094 | 8/2005 |
| WO | WO 2005/120152 A2 | 12/2005 |
| WO | WO 2005/121348 A1 | 12/2005 |
| WO | WO 2006/074546 A1 | 7/2006 |
| WO | WO 2007/048046 A2 | 4/2007 |

OTHER PUBLICATIONS

Flynn, M.A. et al. "Efficient delivery of small interfering RNA for inhibition of IL-12p40 expression in vivo." *Journal of Inflammation* (Oct. 2004), 1(4):1-12.

GenBank accession No. BD134629 from JP 2002051788 patent application (Komori Toshifumii), Feb. 19, 2002.

Heil, F. et al. "Species-Specific Recognition of Single-Stranded RNA via Toll-like Receptor 7 and 8." *Science* (Mar. 2004), 303:1526-1529.

Judge, A.D. et al. "Sequence-dependent stimulation of the mammalian innate immune response by synthetic siRNA." *Nature Biotechnology* (Apr. 2005), 23(4):457-462.

Martinez, A. et al. "Small Interfering RNA Molecules as Potential Anti-Human Hepatitis C Virus Agents: Identification and Characterization of Two siRNA Molecules Highly Conserved in the Major Genotypes of the Virus." *Preclinica.* (Nov./Dec. 2003), 1(5):274-283.

Sioud, M. "Induction of Inflammatory Cytokines and Interferon Responses by Double-stranded and Single-stranded siRNAs is Sequence-dependent and Requires Endosomal Localization." *Journal of Molecular Biology* (2005), 348:1079-1090.

Ballas, N. et al., "Liposomes bearing a quarternary ammonium detergent as an efficient vehicle for functional transfer of TMV-RNA into plant protoplasts," *Biochim. Biophys. Acta*, 1998. pp. 8-18, vol. 939.

Barinaga, M., "Step Taken Toward Improved Vectors for Gene Transfer," *Science*, 1994, p. 1326, vol. 266.

Behr, J-P., "Synthetic Gene-Transfer Vectors," *Acc. Chem. Res.* 1993, pp. 274-278, vol. 26.

Brigham, K. et al., "Rapid Communication: In vivo Transfection of Murine Lungs with a Functioning Prokaryotic Gene Using a Liposome Vehicle," *Am. J. Med. Sci.*, 1989, pp. 278-281, vol. 298.

Cortesi, R., et al., "Effect of cationic liposome composition on in vitro cytotoxicity and protective effect on carried DNA," *International Journal of Pharmaceutics*, 1996, pp. 69-78, vol. 139.

Crystal, R., "Transfer of Genes to Humans: Early Lessons and Obstacles to Success," *Science*, 1995, pp. 404-410, vol. 270.

Culver K.,, "The First Human Gene Therapy Experiment," *Gene Therapy: A Handbook for Physicians*, 1994, pp. 33-40.

Duzgunes, N., "Membrane Fusion," *Subcellular Biochemistry*, 1985, pp. 195-286, vol. 11.

Dwarki, V.J., et al., "Cationic Liposime-Mediated RNA Transfection," *Methods in Enzymology*, 1993, pp. 644-654, vol. 217.

Enoch, H. et al., "Formation and properties of 1000-A-diameter, single-bilayer phospholipid vesicles," *Proc. Natl. Acad. Sci. USA*, 1979, pp. 145-149, vol. 76, No. 1.

Felgner, P. et al., "Lipofection: A highly efficient, lipid-mediated DNA-transfection procedure," *Proc. Natl. Acad. Sci. USA*, 1987, pp. 7413-7417, vol. 84.

Felgner, J.H., et al., "Enhanced Gene Delivery and Mechanism Studies with a Novel Series of Cationic Lipid Formulations," *The Journal of Biological Chemistry*, Jan. 1994, pp. 2550-2561, vol. 269, No. 4.

Felgner, J., et al., "Cationic Lipid-Mediated Transfection in Mammalian Cells: "Lipofection"," *J. Tiss. Cult. Meth.*, 1993, pp. 63-68, vol. 15.

Felgner, P.L., et al., "Cationic Liposome Mediated Transfection," *Proc. West. Pharmacol. Soc.*, 1989, pp. 115-121, vol. 32.

Gao, X. et al., "A Novel Cationic Liposome Reagent for Efficient Transfection of Mammalian Cells," *Biochem. Biophys. Res. Comm.*, 1991, pp. 280-285, vol. 179.

Gershon, H. et al., "Mode of Formation and Structural Feature of DNA-Cationic Liposome Complexes Used for Transfection," *Biochemistry*, 1993, pp. 7413-7151, vol. 32.

Guy-Caffey, J., et al., "Novel Polyaminolipids Enhance the Cellular Uptake of Oligonucleotides," *The Journal of Biological Chemistry*, Dec. 1995, pp. 31391-31396, vol. 270, No. 52.

Hawley-Nelson, et al., "LipofectAmine™ Reagent: A New, Higher Efficiency Polycationic Liposome Transfection Reagent," *Focus*, 1993, p. 73-80, vol. 15, No. 3.

Hyde, S., et al., "Correction of the ion transport defect in cystic fibrosis transgenic mice by gene therapy," *Nature*, 1993, pp. 250-256, vol. 362.

Jiang, Lei et al.; "Comparison of protein precipitation methods for sample preparation prior to proteomic analysis"; 2004, *Journal of Chromatography*, vol. 1023, No. 2, pp. 317-320.

Juliano R., and Stamp, D., "The Effect of Particle Size and Charge on the Clearance Rates of Liposomes and Liposome Encapsulated Drugs," *Biochem. Biophys. Res. Commun.*, 1975, pp. 651-658, vol. 63.

Legendre, J.Y. and Szoka, F., "Delivery of Plasmid DNA into Mammalian Cell Lines Using pH-Sensitive Liposomes: Comparison with Cationic Liposomes," *Pharm. Res.*, 1992, pp. 1235-1242, vol. 9, No. 10.

Leventis, R., et al.,, "Interactions of mammalian cells with lipid dispersions containing novel metabolizable cationic amphiphiles," *Biochem. Biophys. Acta*, 1990, p. 124, vol. 1023.

Marshall, E., "Gene Therapy's Growing Pains," *Science*, 1995, pp. 1050-1055, vol. 269.

Orkin, et al., *NIH Report, Report and Recommendations of the Panel to Assess the NIH Investment in Research on Gene Therapy*, 1995.

Paul, Cnythia P. et al.; "Effective expression of small interfering RNA in human cells"; 2002, *Nature Biotechnology*, vol. 20, pp. 505-508.

Puyal, C., et al., "A new cationic liposome encapsulating genetic material: A potential delivery system for polynucleotides," *Eur. J. Biochem.*, 1995, pp. 697-703, vol. 228.

Spagnou, Sebastien et al.; "Lipidic Carriers of siRNA: Differences in the Formulation, Cellular Uptake, and Delivery with Plasmid DNA"; 2004, *Biochemistry*, vol. 43, pp. 13348-13356.

Stamatatos, L., et al., "Interactions of Cationic Lipid Vesicles with Negatively Charged Phospholipid Vesicles and Biological Membranes," *Biochemistry*, 1988, pp. 3917-3925, vol. 27.

Szoka, F. et al., "Comparative Properties and Methods of Preparation of Lipid Vesicles (Liposomes)," *Ann. Rev. Biophys. Bioeng.*, 1980, pp. 467-508, vol. 9.

Szoka, F. et al., "Procedure for preparation of liposomes with large internal aqueous space and high capture by reverse-phase evaporation," *Proc. Natl. Acad. Sci. USA*, 1978, pp. 4194-4198, vol. 75, No. 9.

Van Der Woude, I., et al., "Parameters influencing the introduction of plasmid DNA into cells by the use of synthetic amphiphiles as a carrier system," *Biochimica et Biophysica Acta*, 1995, pp. 34-40, vol. 1240.

Wilson, R. et al., "Counterion-Induced Condensation of Deoxyribonucleic Acid. A Light-Scattering Study." *Biochemistry*, 1979, pp. 2192-2196, vol. 18.

Woodle, M.C. et al., "Versatility in lipid compositions showing prolonged circulation with sterically stabilized liposomes," *Biochem. Biophys. Acta*, 1992, pp. 193-200, vol. 1105.

Zhu, N., et al., "Systemic Gene Expression After Intravenous DNA Delivery into Adult Mice," Science, 1993, pp. 209-211, vol. 261.

Alexopoulou, L., et al., "Recognition of double-stranded RNA and activation of NF-kappaB by Toll-like receptor 3," Nature, 2001, vol. 413, No. 6857, pp. 732-738.

Beale, G., et al., "Gene Silencing Nucleic Acids Designed by Scanning Arrays: Anti-EGFR Activity of siRNA, Ribozyme and DNA Enzymes Targeting a Single Hybridization-accessible Region using the Same Delivery System," Journal of Drug Targeting, 2003, vol. 11, No. 7, pp. 449-456.

Bridge, A.J., et al., "Induction of an interferon response by RNAi vectors in mammalian cells," Nat. Genet., 2003, vol. 34, No. 3, pp. 263-264.

Diebold, S.S., et al., "Innate antiviral responses by means of TLR7-mediated recognition of single-stranded RNA," Science, 2004, vol. 303, No. 5663, pp. 1529-1531.

Hornung, V., et al., "Sequence-specific potent induction of IFN-alpha by short interfering RNA in plasmacytoid dendritic cells through TLR7," Nat. Med., 2005, vol. 11, No. 3, pp. 263-270.

Kariko, K., et al., "Small Interfering RNAs Mediate Sequence-Independent Gene Suppression and Induce Immune Activation by Signaling through Toll-Like Receptor 3," Journal of Immunology, 2004, vol. 172, No. 11, pp. 6545-6549.

Keough, K., "Influence of chain unsaturation and chain position on thermotropism and intermolecular interactions in membranes," Biochem. Soc. Transactions, 1990, vol. 18, No. 5, pp. 835-837.

Kim, D.H., et al., "Interferon induction by siRNAs and ssRNAs synthesized by phage polymerase," Nat. Biotechnol., 2004, vol. 22, No. 3, pp. 321-325.

Lund, J.M., et al., "Recognition of single-stranded RNA viruses by Toll-like receptor 7," Proc. Natl. Acad. Sci. USA, 2004, vol. 101, No. 15, pp. 5598-5603.

Sioud, M., et al., "Cationic liposome-mediated delivery of siRNAs in adult mice," Biochem. Biophys. Res. Commun., 2003, vol. 312, No. 4, pp. 1220-1225.

Sledz, C.A., et al., "Activation of the interferon system by short-interfering RNAs," Nat. Cell Biol., 2003, vol. 5, No. 9, pp. 834-839.

Allerson, C. R., et al., "Chemically-modified siRNA motifs with enhanced in vitro activity and stability—MEDI 174," General Oral Session, Division of Medicinal Chemistry, The 227th ACS National Meeting, 2004, 1 page.

Allerson, C. R., et al., "Fully 2'-Modified Oligonucleotide Duplexes with Improved in Vitro Potency and Stability Compared to Unmodified Small Interfering RNA," J. Med. Chem., 2005, vol. 48, No. 4, pp. 901-904.

Arpicco, S., et al., "Preparation and Characterization of Novel Cationic Lipids Developed for Gene Transfection," Proceed. Int'l Symp. Control. Rel. Bioact. Mater. (Controlled Release Society, Inc.), 1999, vol. 26, pp. 759-760.

Arpicco, S., et al., "Synthesis, characterization and transfection activity of new saturated and unsaturated cationic lipids," IL Farmaco, 2004, vol. 59, pp. 869-878.

Braasch, D. A., et al., "RNA Interference in Mammalian Cells by Chemically Modified RNA," Biochemistry, 2003, vol. 42, No. 26, pp. 7967-7975.

Cevc, G., "How Membrane Chain-Melting Phase-Transition Temperature is Affected by the Lipid Chain Asymmetry and Degree of Unsaturation: An Effective Chain-Length Model," Biochemistry, 1991, vol. 30, pp. 7186-7193.

Chiu, Y., et al., "siRNA function in RNAi: A chemical modification analysis," RNA, 2003, vol. 9, No. 9, pp. 1034-1048.

Czauderna, F., et al., "Structural variations and stabilizing modifications of synthetic siRNAs in mammalian cells," Nucleic Acids Research, 2003, vol. 31, No. 11, pp. 2705-2716.

Elbashir, S. M., et al., "Functional anatomy of siRNAs for mediating efficient RNAi in *Drosophila melanogaster* embryo lysate," The EMBO Journal, 2001, vol. 20, No. 23, pp. 6877-6888.

Heyes, James, "Cationic lipid saturation influences intracellular delivery of encapsulated nucleic acids," Journal of Controlled Release, 2005, vol. 107, pp. 276-287.

Judge, A. D., et al., "Design of Noninflammatory Synthetic siRNA Mediating Potent Gene Silencing in Vivo," Molecular Therapy, 2006, vol. 13, No. 3, pp. 494-505.

Manoharan, M., "RNA interference and chemically modified small interfering RNAs," Current Opinion in Chemical Biology, 2004, vol. 8, pp. 570-579.

Morrissey, D. V., et al., "Potent and persistent in vivo anti-HBV activity of chemically modified siRNAs," Nature Biotechnology, 2005, vol. 23, No. 8, pp. 1002-1007.

Prakash, T. P., et al., "Position effects of chemical modification on siRNA activity—MEDI 175," General Oral Session, Division of Medicinal Chemistry, The 227th ACS National Meeting, 2004, 1 page.

Sioud, M. "Single-stranded small interfering RNA are more immunostimulatory that their double-stranded counterparts: a central role for 2'-hydroxy uridines in immune responses," European Journal of Immunology, 2006, vol. 36, pp. 1222-1230.

Soutschek, J., et al., "Therapeutic silencing of an endogenous gene by systemic administration of modified siRNAs," Nature, 2004, vol. 432, pp. 173-178.

Hafez et al. "On the mechanism whereby cationic lipids promote intracellular delivery of polynucleic acids," Gene Therapy, 2001, vol. 8, pp. 1188-1196.

Jeffs et al. "A scalable, extrusion-free method for efficient liposomal encapsulation of plasmid DNA," Pharmaceutical Research, 2005, vol. 22 No. 3, pp. 362-372.

Tranchant et al. "Physicochemical optimisation of plasmid delivery by cationic lipids," The Journal of Gene Medicine, 2004, vol. 6, pp. S24-S35

Brummelkamp et al. "A System for Stable Expression of Short Interfering RNAs in Mammalian Cells," Science, 2002, vol. 296, pp. 550-553.

Heyes et al. "Synthesis of Novel Cationic Lipids: Effect of Structural Modification on the Efficiency of Gene Transfer," J. Med. Chem., 2002, vol. 45, pp. 99-114.

Interview Summary dated Sep. 30, 2009 issued in U.S. Appl. No. 11/148,152, filed Jun. 7, 2005. (4 pages).

Mashek et al. "Short Communication: Net Uptake of Nonesterified Long Chain Fatty Acids by the Perfused Caudate Lobe of the Caprine Liver," J. Dairy Sci., 2003, 86:1218-1220.

Office Action dated May 27, 2009 issued in U.S. Appl. No. 11/148,152, filed Jun. 7, 2005. (10 pages).

Office Action dated Jan. 28, 2010 issued in U.S. Appl. No. 11/283,550, filed Nov. 17, 2005. (16 pages).

Office Action dated Oct. 2, 2008 issued in U.S. Appl. No. 11/148,152, filed Jun. 7, 2005. (9 pages).

Office Action dated Oct. 8, 2009 issued in U.S. Appl. No. 11/148,430, filed Jun. 7, 2005. (19 pages).

Office Action dated Nov. 24, 2009 issued in U.S. Appl. No. 11/148,430, filed Jun. 7, 2005. (14 pages).

Office Action dated Sep. 20, 2007 issued in U.S. Appl. No. 11/148,152, filed Jun. 7, 2005. (13 pages).

Office Action dated Sep. 20, 2007 issued in U.S. Appl. No. 11/148,430, filed Jun. 7, 2005. (13 pages).

Office Action dated Sep. 23, 2008 issued in U.S. Appl. No. 11/148,430, filed Jun. 7, 2005. (8 pages).

Office Action dated Feb. 4, 2010 issued in U.S. Appl. No. 11/148,152, filed Jun. 7, 2005. (8 pages).

Vigh et al. "Does the membrane's physical state control the expression of heat shock and other genes?" TIBS, 1998, 23:369-374.

Interview Summary mailed on Apr. 6, 2010 for U.S. Appl. No. 11/148,152, filed Jun. 7, 2005; (3 pp.).

Advisory Action mailed on Feb. 25, 2010 for U.S. Appl. No. 11/148,430, filed Jun. 7, 2005; (3 pp.).

Notice of Allowance and Fee(s) Due mailed on Apr. 9, 2010 for U.S. Appl. No. 11/148,430, filed Jun. 7, 2005; (10 pp.).

* cited by examiner

FIG. 3
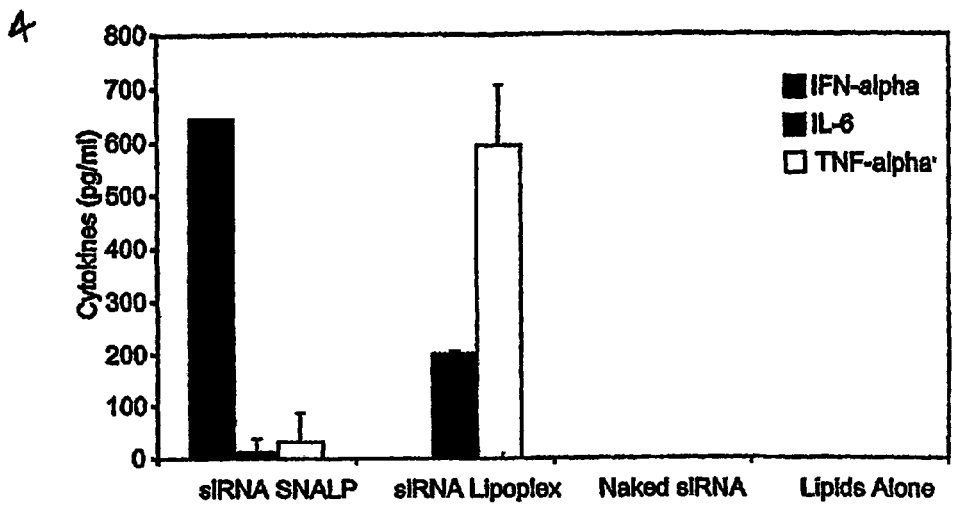
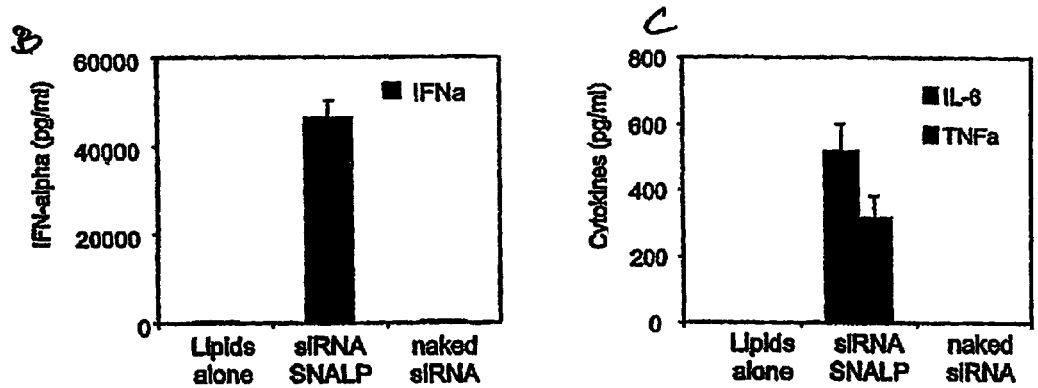
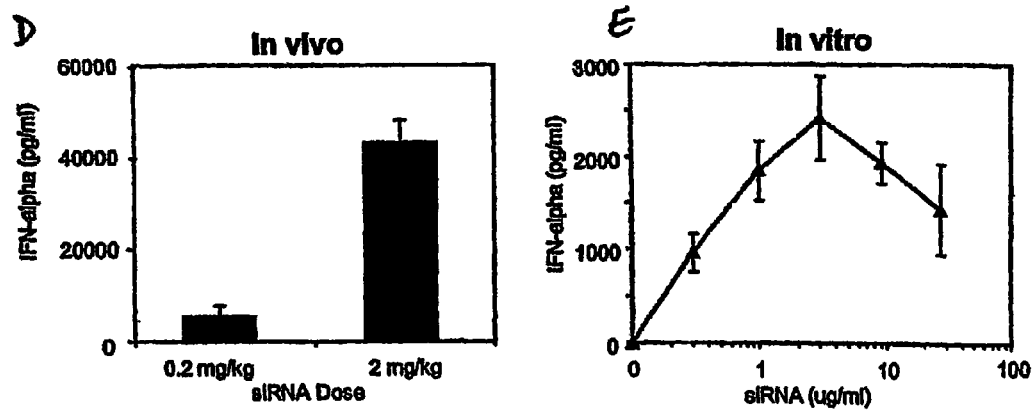

FIG. 9
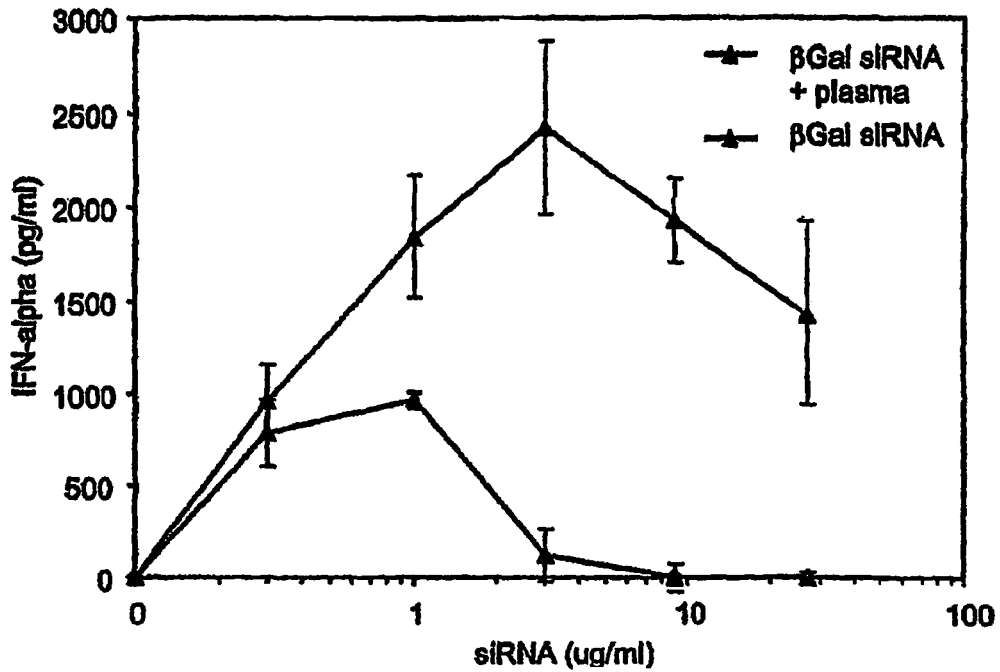
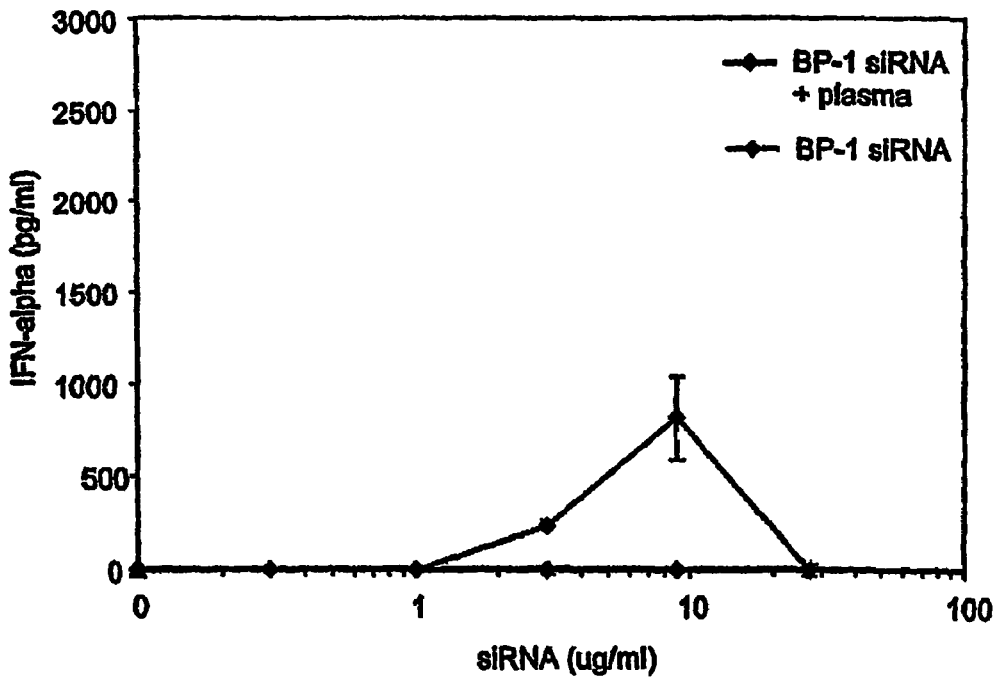

FIG. 10

Table 1

| siRNA | | IFN-α | In Vitro | | | In Vivo | | |
|---|---|---|---|---|---|---|---|---|
| | | | IL-6 | TNF-α | IFN-γ | IFN-α | IL-6 | TNF-α | IFN-γ |
| Anti-Luc | Target Sequence<br>AAGAUUAUGUCCGGGUUAUGUA<br><br>Sense Sequence<br>GAUUAUGUCCGGGUUAUGUAUU<br><br>Antisense Sequence<br>5'-P-UACAUAACCGGACAUAAUCUU | - | ++ | +++ | N/A | + | + | + | ++ |
| Non-specific Luc Control | Target Sequence<br>AAAUGUAUUGGCCUGUAUUAG<br><br>Sense Sequence<br>AUUGUAUUGGCCUGUAUUAGUU<br><br>Antisense Sequence<br>5'-P-CUAAUACAGGCCAAUACAUUU | - | ++ | +++ | N/A | + | + | + | ++ |
| Anti-β-gal | Target Sequence<br>AACUACACAAAAUCAGCGAUU<br><br>Sense Sequence<br>CUACACAAAAUCAGCGAUUUU<br><br>Antisense Sequence<br>5'-P-AAAUCGCUGAUUUUGUGUAGUU | +++ | +++ | +++ | N/A | +++ | +++ | +++ | +++ |
| Non-specific β-gal Control | Target Sequence<br>AAUAGCGACUAAACACAUCAA<br><br>Sense Sequence<br>UAGCGACUAAACACAUCAAUU | +++ | +++ | +++ | N/A | ++ | ++ | ++ | +++ |

FIG. 10 cnt.

| | | | | | | | | | |
|---|---|---|---|---|---|---|---|---|---|
| Anti-β-gal Mod 1 | Target Sequence<br>AAUAG.CG.ACU.AAA.CG.CAU.CAA<br><br>Sense Sequence<br>UAG.CG.AGU.AAA.CG.CAU.CAA.UU<br><br>Antisense Sequence<br>UUG.AUG.CGU.UUA.GU.CG.CUA.UU | N/A | N/A | N/A | N/A | -/+ | | -/+ | -/+ |
| Anti-β-gal Mod 2 | Target Sequence<br>AAUAG.CG.ACU.AAA.CG.CAU.CAA<br><br>Sense Sequence<br>UAG.CG.ACU.AAA.CG.CAU.CAA.UU<br><br>Antisense Sequence<br>UUG.AUG.CGU.UUA.GU.CG.CUA.UU | N/A | N/A | N/A | N/A | -/+ | - | - | -/+ |
| Anti-BP1-23 | Target Sequence<br>AAC.AG.CUU.UGG.AG.CCU.GGU.AU<br><br>Sense Sequence<br>CAG.CUU.UGG.AG.CUG.GUA.UU<br><br>Antisense Sequence<br>5'-P.AUACC.AGG.CU.CC.AAA.GCU.GUU | - | + | + | N/A | -/+ | | | + |
| Anti-BP1-23 Control | Target Sequence<br>AAC.AG.CUU.UGG.CU.GAG.CG.UAU<br><br>Sense Sequence<br>CAG.CUU.UGG.CU.GAG.CG.UAU.UU<br><br>Antisense Sequence<br>5'-P.AUACG.CU.CAG.CCA.AAG.CUG.UU | - | -/+ | + | N/A | - | - | - | -/+ |

FIG. 10 cont.

| | | | | | | | | |
|---|---|---|---|---|---|---|---|---|
| Anti-BP1-23 Mod 1 Target Sequence AACAGCUUUGUCUGAGCGUAU Sense Sequence CAGCUUUGUCUGAGCGUAUU Antisense Sequence AUACGCUCAGACAAAGCUGUU | N/A | N/A | N/A | N/A | + | +/- | + | -/+ |
| Anti-BP1-23 Mod 2 Target Sequence AACAGCUUUGUGUGAGCGUAU Sense Sequence CAGCUUUGUGUGAGCGUAUU Antisense Sequence AUACGCUCACACAAAGCUGUU | N/A | N/A | N/A | N/A | + | + | ++ | ++ |
| Anti-TetR 57 (see notes for in vitro TetR data) Target Sequence AAGGUCGGAAUCGAAGGUUUA Sense Sequence GGUCGGAAUCGAAGGUUUAUU Antisense Sequence 5'-P.UAAACCUUCGAUUCCGACCUU | N/A | +++ | +/- | N/A | N/A | N/A | N/A | N/A |
| Anti-TetR 547 Target Sequence AAGAGCCAGCCUUUCUUAUUCG Sense Sequence GAGCCAGCCUUUCUUAUUCGUU Antisense Sequence 5'-P.CGAAUAAGAAAGGCUGGCUCUU | N/A | + | -/+ | N/A | N/A | N/A | N/A | N/A |

FIG. 10 cont.

| | | | | | | | | | |
|---|---|---|---|---|---|---|---|---|---|
| Anti-TefR 1 | Target Sequence<br>AAUGAUAGUAUGCCGCCAUUA<br><br>Sense Sequence<br>UGAUAGUAUGCCGCCAUUAUU<br><br>Antisense Sequence<br>5'-P.UAAUGGCGGCAUACUAUCAUU | N/A | + | ++ | N/A | N/A | N/A | N/A | N/A |
| Control TefR | Target Sequence<br>AAGGUCGAAGCUAAAGGUUUA<br><br>Sense Sequence<br>GGUCGAAGCUAAAGGUUUAUU<br><br>Antisense Sequence<br>5'-P.UAAACCUUUAGCUUCGACCUU | N/A | ++ | -/+ | N/A | N/A | N/A | N/A | N/A |
| Anti-TefR 50 | Target Sequence<br>AAUUAAUGAGGUCGGAAUCGA<br><br>Sense Sequence<br>UUAAUGAGGUCGGAAUCGAUU<br><br>Antisense Sequence<br>5'-P.UCGAUUCCGACCUCAUUAAUU | N/A | N/A | N/A | N/A | N/A | N/A | N/A | N/A |
| Anti-TefR 324 | Target Sequence<br>AAACAGUAUGAAACUCUCGAA<br><br>Sense Sequence<br>ACAGUAUGAAACUCUCGAAUU<br><br>Antisense Sequence<br>5'-P.UUCGAGAGUUUCAUACUGUUU | N/A | N/A | N/A | N/A | N/A | N/A | N/A | N/A |

FIG. 10 cont.

| Anti-TetR 425 | N/A | N/A | N/A | N/A | N/A | N/A | N/A | N/A |
|---|---|---|---|---|---|---|---|---|
| Target Sequence<br>AAUAGGUUGCGUAUUGGAAGA.A<br>Sense Sequence<br>UAGGUUGCGUAUUGGAAGAUU<br>Antisense Sequence<br>5'-P.UCUUUCCAAUACGCAACCUAUU | | | | | | | | |

Fig. 10 cnt.

| | | N/A |
|---|---|---|
| ALB1#5 | Target Sequence<br>AAUGAAGUUGCCAAGAAGACAU<br><br>Sense Sequence<br>UGAAGUUGCCAAGAAGACAUUU<br><br>Antisense Sequence<br>AUGUCUUCUUGGCAACUUCAUU | |
| ALB1#6 | Target Sequence<br>AAUGACACCAUGCCUGCUGAU<br><br>Sense Sequence<br>UGACACCAUGCCUGCUGAUUU<br><br>Antisense Sequence<br>AUCAGCAGGCAUGGUGUCAUU | |
| ALB1#7 | Target Sequence<br>AAAGUGUGCAAGAACUAUGCU<br><br>Sense Sequence<br>AGUGUGCAAGAACUAUGCUUU<br><br>Antisense Sequence<br>AGCAUAGUUCUUGCACACUUU | |

FIG. 10 cnt

| | | N/A |
|---|---|---|
| F4/80#1 | Target Sequence<br>AA.G.C.C.A.A.G.U.G.C.A.G.C.U.G.U.C.U.U.A<br>Sense Sequence<br>G.C.C.A.A.G.U.G.C.A.G.C.U.G.U.C.U.U.A.U.U<br>Antisense Sequence<br>U.A.A.G.A.C.A.G.C.U.G.C.A.C.U.U.G.G.C.U.U | |
| F4/80#2 | Target Sequence<br>AA.C.A.G.C.U.G.U.A.C.C.U.G.U.C.A.A.C.C.A<br>Sense Sequence<br>C.A.G.C.U.G.U.A.C.C.U.G.U.C.A.A.C.C.A.U.U<br>Antisense Sequence<br>U.G.G.U.U.G.A.C.A.G.G.U.A.C.A.G.C.U.G.U.U | |
| F4/80#6 | Target Sequence<br>AA.G.A.A.G.U.C.U.G.A.G.A.G.G.C.C.U.A.U.C<br>Sense Sequence<br>G.A.A.G.U.C.U.G.A.G.A.G.G.C.C.U.A.U.C.U.U<br>Antisense Sequence<br>G.A.U.A.G.G.C.C.U.C.U.C.A.G.A.C.U.U.C.U.U | |

β-gal Control siRNA

5'-U U G A U G U G U U U A G U C G C U A-3'
3'-A A C U A C A C A A A U C A G C G A U-5'

Highly Immunostimulatory Duplex

β-gal Mod-1 Sequence

5'-U U G A U G C G U U U A G U C G C U A-3'
3'-A A C U A C G C A A A U C A G C G A U-5'

U→C Base Substitution

β-gal Mod-2 Sequence

5'-U U G A U G C G C U U A G U C G C U A-3'
3'-A A C U A C G C G A A U C A G C G A U-5'

U→C & U→C Substitutions

BP1 Control siRNA

5'-C A G C C U U G G C U U G A G C G U A-3'
3'-G U C G G A A C C G A A C U C G C A U-5'

Less Immunostimulatory Duplex

BP1 Mod-1 Sequence

5'-C A G C C U U G U C U U G A G C G U A-3'
3'-G U C G G A A C A G A A C U C G C A U-5

G→U Substitution

BP1 Mod-2 Sequence

5'-C A G C C U U G U G U U G A G C G U A-3'
3'-G U C G G A A C A C A A C U C G C A U-5'

G→U & C→G Substitutions

FIG. 12A

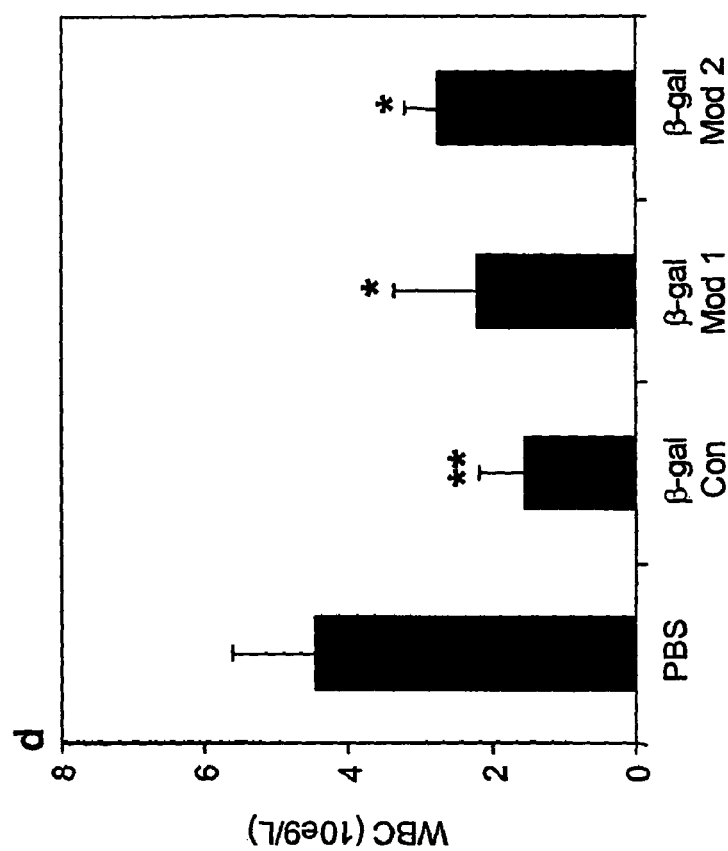
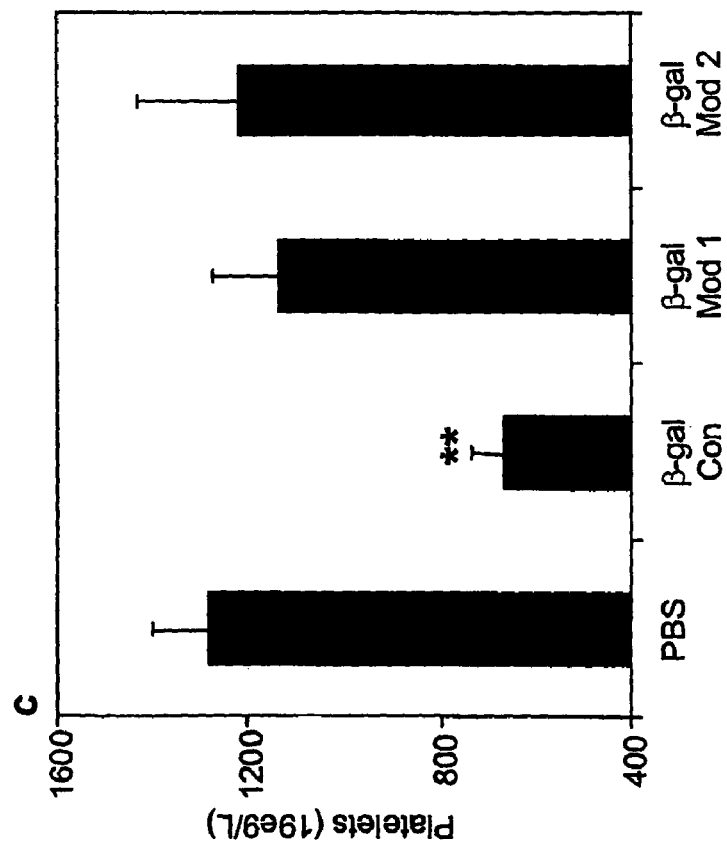
FIG. 12E

| siRNA | | |
|---|---|---|
| Luciferase | 5'-G.A.U.U.A.U.G.U.C.C.G.G.U.U.A.U.G.U.A<br>3'-C.U.A.A.U.A.C.A.G.G.C.C.A.A.U.A.C.A.U | | |
| Luciferase Control | 5'-A.U.G.U.A.U.U.G.G.C.C.U.G.U.A.U.U.A.G<br>3'-U.A.C.A.U.A.A.C.C.G.G.A.C.A.U.A.A.U.C | | |
| β-gal | 5'-C.U.A.C.A.C.A.A.A.U.C.A.G.C.G.A.U.U.U<br>3'-G.A.U.G.U.G.U.U.U.A.G.U.C.G.C.U.A.A.A | | |
| β-gal Control | 5'-U.A.G.C.G.A.C.U.A.A.A.C.A.C.A.U.C.A.A<br>3'-A.U.C.G.C.U.G.A.U.U.U.G.U.G.U.A.G.U.U | | |
| BP1-23 | 5'-C.A.G.C.U.U.U.G.G.A.G.C.C.U.G.G.U.A.U<br>3'-G.U.C.G.A.A.A.C.C.U.C.G.G.A.C.C.A.U.A | | |
| BP1-23 Control | 5'-C.A.G.C.U.U.U.G.G.C.U.G.A.G.C.G.U.A.U<br>3'-G.U.C.G.A.A.A.C.C.G.A.C.U.C.G.C.A.U.A | | |

FIG. 16

β-gal 728
5'-C.U.A.C.A.A.A.U.C.A.G.C.G.A.U.U.U
3'-G.A.U.G.U.U.U.A.G.U.C.G.C.U.A.A.A β-gal 478
5'-G.A.A.G.G.C.C.A.G.A.C.G.A.A.U.U.A
3'-C.U.U.C.C.G.G.U.C.U.G.C.U.U.A.A.U β-gal 924
5'-U.U.A.U.G.C.C.C.G.A.U.C.G.C.A.C.A
3'-A.A.U.A.C.G.G.C.U.A.G.C.G.U.G.U β-gal 2891
5'-G.G.A.C.G.C.G.C.G.A.A.U.U.G.A.A.U.A
3'-C.C.U.G.C.G.C.G.C.U.U.A.A.C.U.U.A.A.U

FIG. 17A

```
SEQUENCE LISTING

<160> NUMBER OF SEQ ID NOS: 113

<210> SEQ ID NO 1
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-Luc (luciferase) target sequence

<400> SEQUENCE: 1
aagauuaugu ccgguuaugu a                                                   21

<210> SEQ ID NO 2
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-Luc (luciferase) sense sequence

<400> SEQUENCE: 2
gauuaugucc gguuauguau u                                                   21

<210> SEQ ID NO 3
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-Luc (luciferase) antisense sequence
```

```
<221> NAME/KEY: modified_base
<222> LOCATION: (1)...(1)
<223> OTHER INFORMATION: n = u modified by 5'-phosphate

<400> SEQUENCE: 3
nacauaaccg gacauaaucu u                                              21

<210> SEQ ID NO 4
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) non-specific Luc (luciferase) control target
      sequence

<400> SEQUENCE: 4
aaauguauug gccuguauua g                                              21

<210> SEQ ID NO 5
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) non-specific Luc (luciferase) control sense
      sequence

<400> SEQUENCE: 5
auguauuggc cuguauuagu u                                              21

<210> SEQ ID NO 6
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) non-specific Luc (luciferase) control
      antisense sequence
<221> NAME/KEY: modified_base
<222> LOCATION: (1)...(1)
<223> OTHER INFORMATION: n = c modified by 5'-phosphate

<400> SEQUENCE: 6
nuaauacagg ccaauacauu u                                              21

<210> SEQ ID NO 7
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-beta-gal (beta-galactosidase) target
      sequence

<400> SEQUENCE: 7
aacuacacaa aucagcgauu u                                              21

<210> SEQ ID NO 8
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-beta-gal (beta-galactosidase) sense
      sequence
```

```
<400> SEQUENCE: 8
cuacacaaau cagcgauuuu u                                              21

<210> SEQ ID NO 9
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-beta-gal (beta-galactosidase) antisense
      sequence
<221> NAME/KEY: modified_base
<222> LOCATION: (1)...(1)
<223> OTHER INFORMATION: n = a modified by 5'-phosphate

<400> SEQUENCE: 9
naaucgcuga uuuguguagu u                                              21

<210> SEQ ID NO 10
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) non-specific beta-gal (beta-galactosidase)
      control target sequence

<400> SEQUENCE: 10
aauagcgacu aaacacauca a                                              21

<210> SEQ ID NO 11
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) non-specific beta-gal (beta-galactosidase)
      control sense sequence

<400> SEQUENCE: 11
uagcgacuaa acacaucaau u                                              21

<210> SEQ ID NO 12
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) non-specific beta-gal (beta-galactosidase)
      control antisense sequence
<221> NAME/KEY: modified_base
<222> LOCATION: (1)...(1)
<223> OTHER INFORMATION: n = u modified by 5'-phosphate

<400> SEQUENCE: 12
nugauguguu uagucgcuau u                                              21

<210> SEQ ID NO 13
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-beta-gal (beta-galactosidase) Mod 1
      target sequence

<400> SEQUENCE: 13
aauagcgacu aaacgcauca a                                              21
```

```
<210> SEQ ID NO 14
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-beta-gal (beta-galactosidase) Mod 1
      sense sequence

<400> SEQUENCE: 14
uagcgacuaa acgcaucaau u                                             21

<210> SEQ ID NO 15
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-beta-gal (beta-galactosidase) Mod 1
      antisense sequence

<400> SEQUENCE: 15
uugaugcguu uagucgcuau u                                             21

<210> SEQ ID NO 16
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-beta-gal (beta-galactosidase) Mod 2
      target sequence

<400> SEQUENCE: 16
aauagcgacu aagcgcauca a                                             21

<210> SEQ ID NO 17
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-beta-gal (beta-galactosidase) Mod 2
      sense sequence

<400> SEQUENCE: 17
uagcgacuaa gcgcaucaau u                                             21

<210> SEQ ID NO 18
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-beta-gal (beta-galactosidase) Mod 2
      antisense sequence

<400> SEQUENCE: 18
uugaugcgcu uagucgcuau u                                             21

<210> SEQ ID NO 19
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-breast cancer associated BP1-23 target
      sequence
```

```
<400> SEQUENCE: 19
aacagcuuug gagccuggua u                                              21

<210> SEQ ID NO 20
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-breast cancer associated BP1-23 sense
      sequence

<400> SEQUENCE: 20
cagcuuugga gccugguauu u                                              21

<210> SEQ ID NO 21
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-breast cancer associated BP1-23
      antisense sequence
<221> NAME/KEY: modified_base
<222> LOCATION: (1)...(1)
<223> OTHER INFORMATION: n = a modified by 5'-phosphate

<400> SEQUENCE: 21
nuaccaggcu ccaaagcugu u                                              21

<210> SEQ ID NO 22
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-breast cancer associated BP1-23 control
      target sequence

<400> SEQUENCE: 22
aacagcuuug gcugagcgua u                                              21

<210> SEQ ID NO 23
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-breast cancer associated BP1-23 control
      sense sequence

<400> SEQUENCE: 23
cagcuuuggc ugagcguauu u                                              21

<210> SEQ ID NO 24
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-breast cancer associated BP1-23 control
      antisense sequence
<221> NAME/KEY: modified_base
<222> LOCATION: (1)...(1)
<223> OTHER INFORMATION: n = a modified by 5'-phosphate

<400> SEQUENCE: 24
nuacgcucag ccaaagcugu u                                              21
```

```
<210> SEQ ID NO 25
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-breast cancer associated BP1-23 Mod 1
      target sequence

<400> SEQUENCE: 25
aacagcuuug ucugagcgua u                                              21

<210> SEQ ID NO 26
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-breast cancer associated BP1-23 Mod 1
      sense sequence

<400> SEQUENCE: 26
cagcuuuguc ugagcguauu u                                              21

<210> SEQ ID NO 27
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-breast cancer associated BP1-23 Mod 1
      antisense sequence

<400> SEQUENCE: 27
auacgcucag acaaagcugu u                                              21

<210> SEQ ID NO 28
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-breast cancer associated BP1-23 Mod 2
      target sequence

<400> SEQUENCE: 28
aacagcuuug ugugagcgua u                                              21

<210> SEQ ID NO 29
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-breast cancer associated BP1-23 Mod 2
      sense sequence

<400> SEQUENCE: 29
cagcuuugug ugagcguauu u                                              21

<210> SEQ ID NO 30
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-breast cancer associated BP1-23 Mod 2
      antisense sequence
```

```
<400> SEQUENCE: 30
auacgcucac acaaagcugu u                                              21

<210> SEQ ID NO 31
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-TetR 57 (Tetracycline Resistance gene)
      target sequence

<400> SEQUENCE: 31
aaggucggaa ucgaagguuu a                                              21

<210> SEQ ID NO 32
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-TetR 57 (Tetracycline Resistance gene)
      sense sequence

<400> SEQUENCE: 32
ggucggaauc gaagguuuau u                                              21

<210> SEQ ID NO 33
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-TetR 57 (Tetracycline Resistance gene)
      antisense sequence
<221> NAME/KEY: modified_base
<222> LOCATION: (1)...(1)
<223> OTHER INFORMATION: n = u modified by 5'-phosphate

<400> SEQUENCE: 33
naaaccuucg auuccgaccu u                                              21

<210> SEQ ID NO 34
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-TetR 547 (Tetracycline Resistance gene)
      target sequence

<400> SEQUENCE: 34
aagagccagc cuucuuauuc g                                              21

<210> SEQ ID NO 35
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-TetR 547 (Tetracycline Resistance gene)
      sense sequence

<400> SEQUENCE: 35
gagccagccu ucuuauucgu u                                              21
```

```
<210> SEQ ID NO 36
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-TetR 547 (Tetracycline Resistance gene)
      antisense sequence
<221> NAME/KEY: modified_base
<222> LOCATION: (1)...(1)
<223> OTHER INFORMATION: n = c modified by 5'-phosphate

<400> SEQUENCE: 36
ngaauaagaa ggcuggcucu u                                              21

<210> SEQ ID NO 37
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-TetR 1 (Tetracycline Resistance gene)
      target sequence

<400> SEQUENCE: 37
aaugauagua ugccgccauu a                                              21

<210> SEQ ID NO 38
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-TetR 1 (Tetracycline Resistance gene)
      sense sequence

<400> SEQUENCE: 38
ugauaguaug ccgccauuau u                                              21

<210> SEQ ID NO 39
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-TetR 1 (Tetracycline Resistance gene)
      antisense sequence
<221> NAME/KEY: modified_base
<222> LOCATION: (1)...(1)
<223> OTHER INFORMATION: n = u modified by 5'-phosphate

<400> SEQUENCE: 39
naauggcggc auacuaucau u                                              21

<210> SEQ ID NO 40
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) control TetR (Tetracycline Resistance gene)
      target sequence

<400> SEQUENCE: 40
aaggucggag cuaaagguuu a                                              21
```

```
<210> SEQ ID NO 41
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) control TetR (Tetracycline Resistance gene)
      sense sequence

<400> SEQUENCE: 41
ggucggagcu aaagguuuau u                                              21

<210> SEQ ID NO 42
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) control TetR (Tetracycline Resistance gene)
      antisense sequence
<221> NAME/KEY: modified_base
<222> LOCATION: (1)...(1)
<223> OTHER INFORMATION: n = u modified by 5'-phosphate

<400> SEQUENCE: 42
naaaccuuua gcuccgaccu u                                              21

<210> SEQ ID NO 43
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-TetR 50 (Tetracycline Resistance gene)
      target sequence

<400> SEQUENCE: 43
aauuaaugag gucggaaucg a                                              21

<210> SEQ ID NO 44
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-TetR 50 (Tetracycline Resistance gene)
      sense sequence

<400> SEQUENCE: 44
uuaaugaggu cggaaucgau u                                              21

<210> SEQ ID NO 45
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-TetR 50 (Tetracycline Resistance gene)
      antisense sequence
<221> NAME/KEY: modified_base
<222> LOCATION: (1)...(1)
<223> OTHER INFORMATION: n = u modified by 5'-phosphate

<400> SEQUENCE: 45
ncgauuccga ccucauuaau u                                              21
```

```
<210> SEQ ID NO 46
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-TetR 324 (Tetracycline Resistance gene)
      target sequence

<400> SEQUENCE: 46
aaacaguaug aaacucucga a                                            21

<210> SEQ ID NO 47
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-TetR 324 (Tetracycline Resistance gene)
      sense sequence

<400> SEQUENCE: 47
acaguaugaa acucucgaau u                                            21

<210> SEQ ID NO 48
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-TetR 324 (Tetracycline Resistance gene)
      antisense sequence
<221> NAME/KEY: modified_base
<222> LOCATION: (1)...(1)
<223> OTHER INFORMATION: n = u modified by 5'-phosphate

<400> SEQUENCE: 48
nucgagaguu ucauacuguu u                                            21

<210> SEQ ID NO 49
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-TetR 425 (Tetracycline Resistance gene)
      target sequence

<400> SEQUENCE: 49
aauagguugc guauuggaag a                                            21

<210> SEQ ID NO 50
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) Anti-TetR 425 (Tetracycline Resistance gene)
      sense sequence

<400> SEQUENCE: 50
uagguugcgu auuggaagau u                                            21

<210> SEQ ID NO 51
<211> LENGTH: 21
<212> TYPE: RNA
<213> ORGANISM: Artificial Sequence
```

```
<220> FEATURE:
<223> OTHER INFORMATION: siRNA (small interfering RNA, short interfering
      RNA) Anti-TetR 425 (Tetracycline Resistance gene)
      antisense sequence
<221> NAME/KEY: modified_base
<222> LOCATION: (1)...(1)
<223> OTHER INFORMATION: n = u modified by 5'-phosphate

<400> SEQUENCE: 51
ncuuccaaua cgcaaccuau u                                              21

<210> SEQ ID NO 52
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) ALB1#5 target sequence

<400> SEQUENCE: 52
aaugaaguug ccagaagaca u                                              21

<210> SEQ ID NO 53
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) ALB1#5 sense sequence

<400> SEQUENCE: 53
ugaaguugcc agaagacauu u                                              21

<210> SEQ ID NO 54
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) ALB1#5 antisense sequence

<400> SEQUENCE: 54
augucuucug gcaacuucau u                                              21

<210> SEQ ID NO 55
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) ALB1#6 target sequence

<400> SEQUENCE: 55
aaugacacca ugccugcuga u                                              21

<210> SEQ ID NO 56
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) ALB1#6 sense sequence

<400> SEQUENCE: 56
ugacaccaug ccugcugauu u                                              21
```

<210> SEQ ID NO 57
<211> LENGTH: 21
<212> TYPE: RNA
<213> ORGANISM: Artificial Sequence
<220> FEATURE:
<223> OTHER INFORMATION: siRNA (small interfering RNA, short interfering RNA) ALB1#6 antisense sequence

<400> SEQUENCE: 57
aucagcaggc auggugucau u    21

<210> SEQ ID NO 58
<211> LENGTH: 21
<212> TYPE: RNA
<213> ORGANISM: Artificial Sequence
<220> FEATURE:
<223> OTHER INFORMATION: siRNA (small interfering RNA, short interfering RNA) ALB1#7 target sequence

<400> SEQUENCE: 58
aaagugugca agaacuaugc u    21

<210> SEQ ID NO 59
<211> LENGTH: 21
<212> TYPE: RNA
<213> ORGANISM: Artificial Sequence
<220> FEATURE:
<223> OTHER INFORMATION: siRNA (small interfering RNA, short interfering RNA) ALB1#7 sense sequence

<400> SEQUENCE: 59
agugugcaag aacuaugcuu u    21

<210> SEQ ID NO 60
<211> LENGTH: 21
<212> TYPE: RNA
<213> ORGANISM: Artificial Sequence
<220> FEATURE:
<223> OTHER INFORMATION: siRNA (small interfering RNA, short interfering RNA) ALB1#7 antisense sequence

<400> SEQUENCE: 60
agcauaguuc uugcacacuu u    21

<210> SEQ ID NO 61
<211> LENGTH: 21
<212> TYPE: RNA
<213> ORGANISM: Artificial Sequence
<220> FEATURE:
<223> OTHER INFORMATION: siRNA (small interfering RNA, short interfering RNA) F4/80#1 target sequence

<400> SEQUENCE: 61
aagccaagug cagcugucuu a    21

<210> SEQ ID NO 62
<211> LENGTH: 21
<212> TYPE: RNA
<213> ORGANISM: Artificial Sequence
<220> FEATURE:
<223> OTHER INFORMATION: siRNA (small interfering RNA, short interfering RNA) F4/80#1 sense sequence

<400> SEQUENCE: 62
gccaagugca gcugucuuau u    21

<210> SEQ ID NO 63
<211> LENGTH: 21
<212> TYPE: RNA
<213> ORGANISM: Artificial Sequence
<220> FEATURE:
<223> OTHER INFORMATION: siRNA (small interfering RNA, short interfering RNA) F4/80#1 antisense sequence

<400> SEQUENCE: 63
uaagacagcu gcacuuggcu u                                              21

<210> SEQ ID NO 64
<211> LENGTH: 21
<212> TYPE: RNA
<213> ORGANISM: Artificial Sequence
<220> FEATURE:
<223> OTHER INFORMATION: siRNA (small interfering RNA, short interfering RNA) F4/80#2 target sequence

<400> SEQUENCE: 64
aacagcugua ccugucaacc a                                              21

<210> SEQ ID NO 65
<211> LENGTH: 21
<212> TYPE: RNA
<213> ORGANISM: Artificial Sequence
<220> FEATURE:
<223> OTHER INFORMATION: siRNA (small interfering RNA, short interfering RNA) F4/80#2 sense sequence

<400> SEQUENCE: 65
cagcuguacc ugucaaccau u                                              21

<210> SEQ ID NO 66
<211> LENGTH: 21
<212> TYPE: RNA
<213> ORGANISM: Artificial Sequence
<220> FEATURE:
<223> OTHER INFORMATION: siRNA (small interfering RNA, short interfering RNA) F4/80#2 antisense sequence

<400> SEQUENCE: 66
ugguugacag guacagcugu u                                              21

<210> SEQ ID NO 67
<211> LENGTH: 21
<212> TYPE: RNA
<213> ORGANISM: Artificial Sequence
<220> FEATURE:
<223> OTHER INFORMATION: siRNA (small interfering RNA, short interfering RNA) F4/80#6 target sequence

<400> SEQUENCE: 67
aagaagucug agaggccuau c                                              21

<210> SEQ ID NO 68
<211> LENGTH: 21
<212> TYPE: RNA
<213> ORGANISM: Artificial Sequence
<220> FEATURE:
<223> OTHER INFORMATION: siRNA (small interfering RNA, short interfering RNA) F4/80#6 sense sequence

<400> SEQUENCE: 68
gaagucugag aggccuaucu u                                              21

```
<210> SEQ ID NO 69
<211> LENGTH: 21
<212> TYPE: RNA
<213> ORGANISM: Artificial Sequence
<220> FEATURE:
<223> OTHER INFORMATION: siRNA (small interfering RNA, short interfering
      RNA) F4/80#6 antisense sequence

<400> SEQUENCE: 69
gauaggccuc ucagacuucu u                                             21

<210> SEQ ID NO 70
<211> LENGTH: 19
<212> TYPE: RNA
<213> ORGANISM: Artificial Sequence
<220> FEATURE:
<223> OTHER INFORMATION: beta-gal (beta-galactosidase) control siRNA
      (small interfering RNA, short interfering RNA)

<400> SEQUENCE: 70
uugauguguu uagucgcua                                                19

<210> SEQ ID NO 71
<211> LENGTH: 19
<212> TYPE: RNA
<213> ORGANISM: Artificial Sequence
<220> FEATURE:
<223> OTHER INFORMATION: beta-gal (beta-galactosidase) control siRNA
      (small interfering RNA, short interfering RNA)

<400> SEQUENCE: 71
uagcgacuaa acacaucaa                                                19

<210> SEQ ID NO 72
<211> LENGTH: 19
<212> TYPE: RNA
<213> ORGANISM: Artificial Sequence
<220> FEATURE:
<223> OTHER INFORMATION: beta-gal (beta-galactosidase) Mod 1 siRNA
      (small interfering RNA, short interfering RNA)

<400> SEQUENCE: 72
uugaugcguu uagucgcua                                                19

<210> SEQ ID NO 73
<211> LENGTH: 19
<212> TYPE: RNA
<213> ORGANISM: Artificial Sequence
<220> FEATURE:
<223> OTHER INFORMATION: beta-gal (beta-galactosidase) Mod 1 siRNA
      (small interfering RNA, short interfering RNA)

<400> SEQUENCE: 73
uagcgacuaa acgcaucaa                                                19

<210> SEQ ID NO 74
<211> LENGTH: 19
<212> TYPE: RNA
<213> ORGANISM: Artificial Sequence
<220> FEATURE:
<223> OTHER INFORMATION: beta-gal (beta-galactosidase) Mod 2 siRNA
      (small interfering RNA, short interfering RNA)

<400> SEQUENCE: 74
uugaugcgcu uagucgcua                                                19
```

```
<210> SEQ ID NO 75
<211> LENGTH: 19
<212> TYPE: RNA
<213> ORGANISM: Artificial Sequence
<220> FEATURE:
<223> OTHER INFORMATION: beta-gal (beta-galactosidase) Mod 2 siRNA
      (small interfering RNA, short interfering RNA)

<400> SEQUENCE: 75
uagcgacuaa gcgcaucaa                                                 19

<210> SEQ ID NO 76
<211> LENGTH: 19
<212> TYPE: RNA
<213> ORGANISM: Artificial Sequence
<220> FEATURE:
<223> OTHER INFORMATION: breast cancer associated BP1 control siRNA
      (small interfering RNA, short interfering RNA)

<400> SEQUENCE: 76
cagcuuuggc ugagcguau                                                 19

<210> SEQ ID NO 77
<211> LENGTH: 19
<212> TYPE: RNA
<213> ORGANISM: Artificial Sequence
<220> FEATURE:
<223> OTHER INFORMATION: breast cancer associated BP1 control siRNA
      (small interfering RNA, short interfering RNA)

<400> SEQUENCE: 77
auacgcucag ccaaagcug                                                 19

<210> SEQ ID NO 78
<211> LENGTH: 19
<212> TYPE: RNA
<213> ORGANISM: Artificial Sequence
<220> FEATURE:
<223> OTHER INFORMATION: breast cancer associated BP1 Mod 1 siRNA
      (small interfering RNA, short interfering RNA)

<400> SEQUENCE: 78
cagcuuuguc ugagcguau                                                 19

<210> SEQ ID NO 79
<211> LENGTH: 19
<212> TYPE: RNA
<213> ORGANISM: Artificial Sequence
<220> FEATURE:
<223> OTHER INFORMATION: breast cancer associated BP1 Mod 1 siRNA
      (small interfering RNA, short interfering RNA)

<400> SEQUENCE: 79
auacgcucag acaaagcug                                                 19

<210> SEQ ID NO 80
<211> LENGTH: 19
<212> TYPE: RNA
<213> ORGANISM: Artificial Sequence
<220> FEATURE:
<223> OTHER INFORMATION: breast cancer associated BP1 Mod 2 siRNA
      (small interfering RNA, short interfering RNA)

<400> SEQUENCE: 80
cagcuuugug ugagcguau                                                 19
```

<210> SEQ ID NO 81
<211> LENGTH: 19
<212> TYPE: RNA
<213> ORGANISM: Artificial Sequence
<220> FEATURE:
<223> OTHER INFORMATION: breast cancer associated BP1 Mod 2 siRNA
      (small interfering RNA, short interfering RNA)

<400> SEQUENCE: 81
auacgcucac acaaagcug                                              19

<210> SEQ ID NO 82
<211> LENGTH: 19
<212> TYPE: RNA
<213> ORGANISM: Artificial Sequence
<220> FEATURE:
<223> OTHER INFORMATION: luciferase siRNA (small interfering RNA,
      short interfering RNA)

<400> SEQUENCE: 82
gauuaugucc gguuaugua                                              19

<210> SEQ ID NO 83
<211> LENGTH: 19
<212> TYPE: RNA
<213> ORGANISM: Artificial Sequence
<220> FEATURE:
<223> OTHER INFORMATION: luciferase siRNA (small interfering RNA, short
      interfering RNA)

<400> SEQUENCE: 83
uacauaaccg gacauaauc                                              19

<210> SEQ ID NO 84
<211> LENGTH: 19
<212> TYPE: RNA
<213> ORGANISM: Artificial Sequence
<220> FEATURE:
<223> OTHER INFORMATION: luciferase control siRNA (small interfering
      RNA, short interfering RNA)

<400> SEQUENCE: 84
auguauuggc cuguauuag                                              19

<210> SEQ ID NO 85
<211> LENGTH: 19
<212> TYPE: RNA
<213> ORGANISM: Artificial Sequence
<220> FEATURE:
<223> OTHER INFORMATION: luciferase control siRNA (small interfering
      RNA, short interfering RNA)

<400> SEQUENCE: 85
cuaauacagg ccaauacau                                              19

<210> SEQ ID NO 86
<211> LENGTH: 19
<212> TYPE: RNA
<213> ORGANISM: Artificial Sequence
<220> FEATURE:
<223> OTHER INFORMATION: beta-gal (beta-galactosidase) siRNA (small
      interfering RNA, short interfering RNA)

<400> SEQUENCE: 86
cuacacaaau cagcgauuu                                              19

```
<210> SEQ ID NO 87
<211> LENGTH: 19
<212> TYPE: RNA
<213> ORGANISM: Artificial Sequence
<220> FEATURE:
<223> OTHER INFORMATION: beta-gal (beta-galactosidase) siRNA (small
      interfering RNA, short interfering RNA)

<400> SEQUENCE: 87
aaaucgcuga uuuguguag                                                19

<210> SEQ ID NO 88
<211> LENGTH: 19
<212> TYPE: RNA
<213> ORGANISM: Artificial Sequence
<220> FEATURE:
<223> OTHER INFORMATION: beta-gal (beta-galactosidase) control siRNA
      (small interfering RNA, short interfering RNA)

<400> SEQUENCE: 88
uagcgacuaa acacaucaa                                                19

<210> SEQ ID NO 89
<211> LENGTH: 19
<212> TYPE: RNA
<213> ORGANISM: Artificial Sequence
<220> FEATURE:
<223> OTHER INFORMATION: beta-gal (beta-galactosidase) control siRNA
      (small interfering RNA, short interfering RNA)

<400> SEQUENCE: 89
uugauguguu uagucgcua                                                19

<210> SEQ ID NO 90
<211> LENGTH: 19
<212> TYPE: RNA
<213> ORGANISM: Artificial Sequence
<220> FEATURE:
<223> OTHER INFORMATION: breast cancer associated BP1-23 siRNA (small
      interfering RNA, short interfering RNA)

<400> SEQUENCE: 90
cagcuuugga gccugguau                                                19

<210> SEQ ID NO 91
<211> LENGTH: 19
<212> TYPE: RNA
<213> ORGANISM: Artificial Sequence
<220> FEATURE:
<223> OTHER INFORMATION: breast cancer associated BP1-23 siRNA (small
      interfering RNA, short interfering RNA)

<400> SEQUENCE: 91
auaccaggcu ccaaagcug                                                19

<210> SEQ ID NO 92
<211> LENGTH: 19
<212> TYPE: RNA
<213> ORGANISM: Artificial Sequence
<220> FEATURE:
<223> OTHER INFORMATION: breast cancer associated BP1-23 control siRNA
      (small interfering RNA, short interfering RNA)

<400> SEQUENCE: 92
cagcuuuggc ugagcguau                                                19
```

<210> SEQ ID NO 93
<211> LENGTH: 19
<212> TYPE: RNA
<213> ORGANISM: Artificial Sequence
<220> FEATURE:
<223> OTHER INFORMATION: breast cancer associated BP1-23 control siRNA
      (small interfering RNA, short interfering RNA)

<400> SEQUENCE: 93
auacgcucag ccaaagcug                                              19

<210> SEQ ID NO 94
<211> LENGTH: 19
<212> TYPE: RNA
<213> ORGANISM: Artificial Sequence
<220> FEATURE:
<223> OTHER INFORMATION: beta-gal (beta-galactosidase) 728 siRNA (small
      interfering RNA, short interfering RNA)

<400> SEQUENCE: 94
cuacacaaau cagcgauuu                                              19

<210> SEQ ID NO 95
<211> LENGTH: 19
<212> TYPE: RNA
<213> ORGANISM: Artificial Sequence
<220> FEATURE:
<223> OTHER INFORMATION: beta-gal (beta-galactosidase) 728 siRNA (small
      interfering RNA, short interfering RNA)

<400> SEQUENCE: 95
aaaucgcuga uuuguguag                                              19

<210> SEQ ID NO 96
<211> LENGTH: 19
<212> TYPE: RNA
<213> ORGANISM: Artificial Sequence
<220> FEATURE:
<223> OTHER INFORMATION: beta-gal (beta-galactosidase) 478 siRNA (small
      interfering RNA, short interfering RNA)

<400> SEQUENCE: 96
gaaggccaga cgcgaauua                                              19

<210> SEQ ID NO 97
<211> LENGTH: 19
<212> TYPE: RNA
<213> ORGANISM: Artificial Sequence
<220> FEATURE:
<223> OTHER INFORMATION: beta-gal (beta-galactosidase) 478 siRNA (small
      interfering RNA, short interfering RNA)

<400> SEQUENCE: 97
uaauucgcgu cuggccuuc                                              19

<210> SEQ ID NO 98
<211> LENGTH: 19
<212> TYPE: RNA
<213> ORGANISM: Artificial Sequence
<220> FEATURE:
<223> OTHER INFORMATION: beta-gal (beta-galactosidase) 924 siRNA (small
      interfering RNA, short interfering RNA)

<400> SEQUENCE: 98
uuaugccgau cgcgucaca                                              19

```
<210> SEQ ID NO 99
<211> LENGTH: 19
<212> TYPE: RNA
<213> ORGANISM: Artificial Sequence
<220> FEATURE:
<223> OTHER INFORMATION: beta-gal (beta-galactosidase) 924 siRNA (small
      interfering RNA, short interfering RNA)

<400> SEQUENCE: 99
ugugacgcga ucggcauaa                                                    19

<210> SEQ ID NO 100
<211> LENGTH: 19
<212> TYPE: RNA
<213> ORGANISM: Artificial Sequence
<220> FEATURE:
<223> OTHER INFORMATION: beta-gal (beta-galactosidase) 2891 siRNA (small
      interfering RNA, short interfering RNA)

<400> SEQUENCE: 100
ggacgcgcga auugaauua                                                    19

<210> SEQ ID NO 101
<211> LENGTH: 19
<212> TYPE: RNA
<213> ORGANISM: Artificial Sequence
<220> FEATURE:
<223> OTHER INFORMATION: beta-gal (beta-galactosidase) 2891 siRNA (small
      interfering RNA, short interfering RNA)

<400> SEQUENCE: 101
uaauucaauu cgcgcgucc                                                    19

<210> SEQ ID NO 102
<211> LENGTH: 21
<212> TYPE: RNA
<213> ORGANISM: Artificial Sequence
<220> FEATURE:
<223> OTHER INFORMATION: beta-gal (beta-galactosidase) mismatch motif
      siRNA (small interfering RNA, short interfering RNA)

<400> SEQUENCE: 102
uugauguguu uagucgcuau u                                                 21

<210> SEQ ID NO 103
<211> LENGTH: 21
<212> TYPE: RNA
<213> ORGANISM: Artificial Sequence
<220> FEATURE:
<223> OTHER INFORMATION: beta-gal (beta-galactosidase) mismatch motif
      siRNA (small interfering RNA, short interfering RNA)

<400> SEQUENCE: 103
uagcgacuaa acacaucaau u                                                 21

<210> SEQ ID NO 104
<211> LENGTH: 21
<212> TYPE: RNA
<213> ORGANISM: Artificial Sequence
<220> FEATURE:
<223> OTHER INFORMATION: beta-gal (beta-galactosidase) Mod 1 mismatch
      motif siRNA (small interfering RNA, short interfering RNA)

<400> SEQUENCE: 104
uugaugcguu uagucgcuau u                                                 21
```

<210> SEQ ID NO 105
<211> LENGTH: 21
<212> TYPE: RNA
<213> ORGANISM: Artificial Sequence
<220> FEATURE:
<223> OTHER INFORMATION: beta-gal (beta-galactosidase) Mod 1 mismatch
      motif siRNA (small interfering RNA, short interfering RNA)

<400> SEQUENCE: 105
uagcgacuaa acgcaucaau u                                              21

<210> SEQ ID NO 106
<211> LENGTH: 21
<212> TYPE: RNA
<213> ORGANISM: Artificial Sequence
<220> FEATURE:
<223> OTHER INFORMATION: beta-gal (beta-galactosidase) Mod 2 mismatch
      motif siRNA (small interfering RNA, short interfering RNA)

<400> SEQUENCE: 106
uugaugcgcu uagucgcuau u                                              21

<210> SEQ ID NO 107
<211> LENGTH: 21
<212> TYPE: RNA
<213> ORGANISM: Artificial Sequence
<220> FEATURE:
<223> OTHER INFORMATION: beta-gal (beta-galactosidase) Mod 2 mismatch
      motif siRNA (small interfering RNA, short interfering RNA)

<400> SEQUENCE: 107
uagcgacuaa gcgcaucaau u                                              21

<210> SEQ ID NO 108
<211> LENGTH: 21
<212> TYPE: RNA
<213> ORGANISM: Artificial Sequence
<220> FEATURE:
<223> OTHER INFORMATION: breast cancer associated BP1 mismatch motif
      siRNA (small interfering RNA, short interfering RNA)

<400> SEQUENCE: 108
cagcuuuggc ugagcguauu u                                              21

<210> SEQ ID NO 109
<211> LENGTH: 21
<212> TYPE: RNA
<213> ORGANISM: Artificial Sequence
<220> FEATURE:
<223> OTHER INFORMATION: breast cancer associated BP1 mismatch motif
      siRNA (small interfering RNA, short interfering RNA)

<400> SEQUENCE: 109
auacgcucag ccaaagcugu u                                              21

<210> SEQ ID NO 110
<211> LENGTH: 21
<212> TYPE: RNA
<213> ORGANISM: Artificial Sequence
<220> FEATURE:
<223> OTHER INFORMATION: breast cancer associated BP1 Mod 1 mismatch
      motif siRNA (small interfering RNA, short interfering RNA)

<400> SEQUENCE: 110
cagcuuuguc ugagcguauu u                                              21

```
<210> SEQ ID NO 111
<211> LENGTH: 21
<212> TYPE: RNA
<213> ORGANISM: Artificial Sequence
<220> FEATURE:
<223> OTHER INFORMATION: breast cancer associated BP1 Mod 1 mismatch
      motif siRNA (small interfering RNA, short interfering RNA)

<400> SEQUENCE: 111
auacgcucag acaaagcugu u                                                 21

<210> SEQ ID NO 112
<211> LENGTH: 21
<212> TYPE: RNA
<213> ORGANISM: Artificial Sequence
<220> FEATURE:
<223> OTHER INFORMATION: breast cancer associated BP1 Mod 2 mismatch
      motif siRNA (small interfering RNA, short interfering RNA)

<400> SEQUENCE: 112
cagcuuugug ugagcguauu u                                                 21

<210> SEQ ID NO 113
<211> LENGTH: 21
<212> TYPE: RNA
<213> ORGANISM: Artificial Sequence
<220> FEATURE:
<223> OTHER INFORMATION: breast cancer associated BP1 Mod 2 mismatch
      motif siRNA (small interfering RNA, short interfering RNA)

<400> SEQUENCE: 113
auacgcucac acaaagcugu u                                                 21
```

COMPOSITIONS COMPRISING IMMUNOSTIMULATORY SIRNA MOLECULES AND DLINDMA OR DLENDMA

CROSS-REFERENCES TO RELATED APPLICATIONS

This application claims the benefit of U.S. Provisional Application Nos. 60/665,297, filed Mar. 25, 2005; 60/627, 326, filed Nov. 12, 2004; 60/589,363, filed Jul. 19, 2004; and 60/585,301, filed Jul. 2, 2004, the disclosures of which are hereby incorporated by reference in their entirety for all purposes.

BACKGROUND OF THE INVENTION

RNA interference (RNAi) is an evolutionarily conserved, sequence specific mechanism triggered by double stranded RNA (dsRNA) that induces degradation of complementary target single stranded mRNA and "silencing" of the corresponding translated sequences (McManus and Sharp, *Nature Rev. Genet.* 3:737 (2002)). RNAi functions by enzymatic cleavage of longer dsRNA strands into biologically active "short-interfering RNA" (siRNA) sequences of about 21-23 nucleotides in length (Elbashir, et al., *Genes Dev.* 15:188 (2001)). siRNA can be used to downregulate or silence the transcription and translation of a gene product of interest, i.e., a target sequence.

Nucleic acids, like other macromolecules, can act as biological response modifiers, i.e., can induce immune responses in mammals upon in vivo administration. For example, poly (I:C)-LC has been identified as a potent inducer of interferon (IFN) as well as a macrophage activator and inducer of natural killer (NK) activity (Talmadge et al., *Cancer Res.* 45:1058 (1985); Wiltrout et al., *J. Biol. Resp. Mod.* 4:512 (1985); Krown, *Sem. Oncol.* 13:207 (1986); and Ewel et al., *Canc. Res.* 52:3005 (1992)). Unfortunately, toxic side effects have thus far prevented poly(I:C)-LC and other nucleic acids from becoming a useful therapeutic agent.

Several phosphorothioate modified oligodeoxynucleotides (ODN) have been reported to induce in vitro and in vivo B cell stimulation (Tanaka et al., *J. Exp. Med.* 175:597 (1992); Branda et al., *Biochem. Pharmacol.* 45:2037 (1993); McIntyre et al., *Antisense Res. Develop.* 3:309 (1993); and Pisetsky and Reich, *Life Sciences* 54:101 (1993)). However, none of these reports suggest a common structural motif or sequence element in these ODN that might explain their effects.

Recent reports have indicated that phosphorothioate-protected single-stranded RNA sequences comprising a GU-rich sequence derived from the U5 region of HIV-1 RNA complexed to the cationic lipid 1,2-dioleoyl-3-(trimethyammonium) (DOTAP) can induce expression of the cytokines IL-6, IL-12p40, TNF-α and IFN-α (see, e.g., Heil et al., *Science* 303:1526-1529 (2004)). In addition, U.S. Patent Publication No. 20030232074 and WO 03/086280 describe immunostimulatory RNA molecules, i.e., rRNA, tRNA, mRNA, and vRNA, comprising at least one guanine and at least one uracil. However, these reports do mention or suggest that siRNA has any immunostimulatory properties or that siRNA can be used to modulate an immune response.

Thus, there is a need for nucleic acid compositions that can be modified to modulate (i.e., increase or decrease) their immunostimulatory properties. The present invention addresses these and other needs.

SUMMARY OF THE INVENTION

The present invention provides siRNA molecules and methods of using such siRNA molecules to silence target gene expression and/or to modulate (i.e., enhance or decrease) an immune response associated with the siRNA molecules.

One embodiment of the invention provides a modified siRNA that is capable of silencing expression of a target sequence, comprising a double stranded region of about 15 to about 30 nucleotides in length and a non-immunostimulatory mismatch motif consisting of a 5'-XX'-3' dinucleotide corresponding to a 5'-GU-3' dinucleotide in an unmodified siRNA sequence that is capable of silencing expression of the target sequence, wherein X and X' are independently selected from the group consisting of A, U, C, and G, with the proviso that if X is G, X' is not U and if X' is U, X is not GU. The modified siRNA is less immunogenic than an siRNA that does not comprise the non-immunostimulatory mismatch motif. In some embodiments, the siRNA comprises one, two, three, or more additional immunostimulatory mismatch motifs relative to the target sequence. The immunostimulatory mismatch motifs may be adjacent to each other or, alternatively, they may be separated by 1, 2, 4, 6, 8, 10, or 12 or more nucleotides.

Another embodiment of the invention provides a modified siRNA that is capable of silencing expression of a target sequence comprising a double stranded sequence of about 15 to about 30 nucleotides in length and an immunostimulatory mismatch motif consisting of a 5'-GU-3' dinucleotide corresponding to a 5'-XX'-3' dinucleotide motif in an unmodified siRNA that is capable of silencing expression of a target sequence, wherein X and X' are independently selected from the group consisting of A, U, C, and G, with the proviso that if X is G, X' is not U and if X' is U, X is not GU. The modified siRNA is more immunogenic than an siRNA that does not comprise the immunostimulatory mismatch motif. In some embodiments, the siRNA comprises one, two, three, or more additional immunostimulatory mismatch motifs relative to the target sequence. The immunostimulatory mismatch motifs may be adjacent to each other or, alternatively, they may be separated by 1, 2, 4, 6, 8, 10, or 12 or more nucleotides.

In some embodiments, the siRNA described herein are used in methods of silencing expression of a target sequence and/or in methods of modulating (i.e., enhancing or reducing) immune responses associated with the siRNA. An effective amount of the siRNA is administered to a mammalian subject, thereby silencing expression of a target sequence or modulating an immune response associated with the siRNA.

The invention also provides pharmaceutical compositions comprising the siRNA molecules described herein.

Another embodiment of the invention provides nucleic acid-lipid particles comprising: the siRNA molecules described herein; a cationic lipid; a non-cationic lipid; and a conjugated lipid that inhibits aggregation of particles. The cationic lipid may be, e.g., N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), and N,N-dimethyl-2,3-dioleyloxy)propylamine (DODMA), 1,2-DiLinoleyloxy-N,N-dimethylaminopropane (DLinDMA), and 1,2-Dilinolenyloxy-N,N-dimethylaminopropane (DLendMA), or mixtures thereof. The cationic lipid may comprise from about 2% to about 60%, about 5% to about 45%, about 5% to about 15%, or about 40% to about 50% of the total lipid present in the particle.

The non-cationic lipid may be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or mixtures thereof. The non-cationic lipid comprises from about 5% to about 90% or about 20% to about 85% of the total lipid present in the particle.

The conjugated lipid that inhibits aggregation of particles may be a polyethyleneglycol (PEG)-lipid conjugate, a polyamide (ATTA)-lipid conjugate, a cationic-polymer-lipid conjugates (CPLs), or mixtures thereof. In one preferred embodiment, the nucleic acid-lipid particules comprise either a PEG-lipid conjugate or an ATTA-lipid conjugate together with a CPL. The conjugated lipid that inhibits aggregation of particles may comprise a polyethyleneglycol-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-dilauryloxypropyl (C12), a PEG-dimyristyloxypropyl (C14), a PEG-dipalmityloxypropyl (C16), and a PEG-distearyloxypropyl (C18). In some embodiments, the conjugated lipid that inhibits aggregation of particles has the formula: A-W-Y, wherein: A is a lipid moiety; W is a hydrophilic polymer; and Y is a polycationic moiety. W may be a polymer selected from the group consisting of polyethyleneglycol (PEG), polyamide, polylactic acid, polyglycolic acid, polylactic acid/polyglycolic acid copolymers or combinations thereof, said polymer having a molecular weight of about 250 to about 7000 daltons. In some embodiments, Y has at least 4 positive charges at a selected pH. In some embodiments, Y may be lysine, arginine, asparagine, glutamine, derivatives thereof and combinations thereof. The conjugated lipid that prevents aggregation of particles may be about 0% to about 20%, about 1% to about 15%, about 4% to about 10%, or about 2% of the total lipid present in said particle.

In some embodiments, the nucleic acid-lipid particle further comprises cholesterol at, e.g., about 10% to about 60% or about 20% to about 45% of the total lipid present in said particle.

In some embodiments, the siRNA in the nucleic acid-lipid particle is not substantially degraded after exposure of the particle to a nuclease at 37° C. for at least 20, 30, 45, or 60 minutes; or after incubation of the particle in serum at 37° C. for at least 30, 45, or 60 minutes.

In some embodiments, the siRNA is fully encapsulated in the nucleic acid-lipid particle. In some embodiments, the siRNA is complexed to the lipid portion of the particle.

The present invention further provides pharmaceutical compositions comprising the nucleic acid-lipid particles described herein and a pharmaceutically acceptable carrier.

Yet another embodiment of the invention provides a method of modifying a siRNA having immunostimulatory properties. The method comprises (a) providing an unmodified siRNA sequence comprising at least one GU-rich motif (e.g., a 5'-GU-3' motif) and capable of silencing expression of a target sequence; and (b) modifying the siRNA to substitute the at least one GU-rich motif, with a non-immunostimulatory mismatch motif relative to the target sequence, wherein the non-immunostimulatory mismatch motif consists of a 5'-XX'-3' motif corresponding to the at least one GU-rich motif in the unmodified siRNA sequence, wherein X and X' are independently selected from the group consisting of A, U, C, and G, with the proviso that if X is G, X' is not U and if X' is U, X is not G; thereby generating a modified siRNA that is less immunogenic than the unmodified siRNA sequence and is capable of silencing expression of the target sequence.

Another embodiment of the invention provides a method of modifying an siRNA having non-immunostimulatory properties. The method comprises (a) providing an unmodified siRNA lacking a GU-rich motif (e.g., a 5'-GU-3' motif) and capable of silencing expression of a target sequence; and (b) modifying the siRNA to introduce at least one immunostimulatory mismatch motif relative to the target sequence, wherein the at least one immunostimulatory mismatch motif consists of a GU-rich motif (e.g., a 5'-GU-3' dinucleotide motif) corresponding to a 5'-XX'-3' motif in the unmodified siRNA, wherein X and X' are independently selected from the group consisting of A, U, C, and G, with the proviso that if X is G, X' is not U and if X' is U, X is not G; thereby generating a modified siRNA that is more immunogenic than the unmodified siRNA and is capable of silencing expression of the target sequence.

A further embodiment of the invention provides a method of identifying and/or modifying an siRNA having immunostimulatory properties. The method comprises (a) providing a target nucleic acid sequence; (b) identifying a siRNA sequence that is complementary to the target sequence and comprises at least one GU-rich motif (e.g., a 5'-GU-3' motif), wherein the presence of the at least one GU-rich motif identifies an immunostimulatory siRNA; and (c) contacting the modified siRNA sequence with a mammalian responder cell under conditions suitable for said responder cell to produce a detectable immune response. In some embodiments, the siRNA is modified substituting the at least one GU-rich motif with a non-immunostimulatory mismatch motif relative to the target sequence, wherein the non-immunostimulatory mismatch motif consists of a 5'-XX'-3' motif corresponding to the at least one GU-rich motif in the unmodified siRNA sequence, wherein X and X' are independently selected from the group consisting of A, U, C, and G, with the proviso that if X is G, X' is not U and if X' is U, X is not G, thereby generating a modified siRNA that is less immunogenic than the unmodified siRNA sequence. In some embodiments, the method further comprises contacting the unmodified siRNA sequence with a mammalian responder cell (e.g., a peripheral blood mononuclear cell) under conditions suitable for the responder cell to produce a detectable immune response; and comparing the immune response(e.g., production of a cytokine or growth factor such as, e.g., TNF-α, IFN-α, IL-6, IL-12, and combinations thereof) produced by the modified siRNA with the immune response produced by the unmodified siRNA. The mammalian responder cell may be from a naive mammal (i.e., a mammal that has not previously been in contact with the gene product of the target nucleic acid sequence).

Even another embodiment of the invention provides a method of identifying and/or modifying an siRNA having non-immunostimulatory properties. The method comprises (a) providing a target nucleic acid sequence; (b) identifying a siRNA sequence that is complementary to the target sequence and lacks a 5'-GU-3' motif, wherein the absence of the 5'-GU-3' motif identifies a non-immunostimulatory siRNA; and (c) contacting the modified siRNA sequence with a mammalian responder cell under conditions suitable for the responder cell to produce a detectable immune response. In some embodiments, the method further comprises modifying the siRNA to introduce at least one immunostimulatory mismatch motif relative to the target sequence, wherein the at least one immunostimulatory mismatch motif consists of a 5'-GU-3' dinucleotide corresponding to a 5'-XX'-3' dinucleotide motif in the unmodified siRNA, wherein X and X' are independently selected from the group consisting of A, U, C, and G, with the proviso that if X is G, X' is not U and if X' is U, X is not G, thereby generating a modified siRNA that is more immunogenic than the unmodified siRNA. In some embodiments, the method further comprises contacting the unmodified siRNA sequence with a mammalian responder cell under conditions suitable for the responder cell to produce a detectable immune response; and comparing the immune response (e.g., production of a cytokine or growth factor such as, e.g., TNF-α, IFN-α, IL-6, IL-12, and combinations thereof) produced by the modified siRNA with the immune response produced by the unmodified siRNA.

Even another embodiment of the invention provides isolated nucleic acid molecules comprising a sequence set forth in Table 1, 2, 3, or 4.

BRIEF DESCRIPTION OF THE DRAWINGS

FIG. 2A illustrates data demonstrating targeting of SNALP to liver and FIG. 2B illustrates data demonstrating targeting of SNALP to tumors.

FIG. 3 illustrates data demonstrating that siRNA duplexes stimulate production of type I interferons and inflammatory cytokines in vitro and in vivo. FIG. 3A illustrates data demonstrating that lipid-encapsulated siRNA induces IFN-α production in human PBMC and lipid-complexed siRNA induces IL-6 and TNF-α production in human PBMC. FIG. 3B illustrates data demonstrating that lipid-encapsulated siRNA induces IFN-α production in mice. FIG. 3C illustrates data demonstrating that lipid-encapsulated siRNA induces IL-6 and TNF-α production in mice. FIG. 3D illustrates data demonstrating that IFN-α production in mice is dose dependent. FIG. 3E illustrates data demonstrating that IFN-α production in human PBMC is dose dependent.

FIG. 4A illustrates data demonstrating that the IFN-α response to lipid-encapsulated siRNA is inhibited by chloroquine. FIG. 4B illustrates data demonstrating that the IL-6 response to lipid-encapsulated siRNA is inhibited by chloroquine.

FIG. 9 illustrates data demonstrating that plasma derived factors enhance the immunostimulatory effects of siRNA in vitro and that stimulation of human PBMC by siRNA was also dependent on nucleotide sequence. FIG. 9A shows the immunostimulatory effects of βgal siRNA duplexes. FIG. 9B shows the immunostimulatory effects of BP1 siRNA duplexes.

FIG. 11 illustrates data demonstrating sequence dependent induction of cytokines by systemically administered siRNA.

FIG. 12 illustrates data demonstrating that the immune stimulatory activity of siRNA is regulated by GU-rich motifs. FIG. 12A is Table 2 which sets forth the modified siRNA sequences (SEQ ID NOS:70-81) used in this series of experiments. Series 1; β-gal control (highly stimulatory), β-gal Mod1 (single base substitution) and β-gal Mod2 (double base substitution). Series 2; BP1 control (low stimulatory), BP1 Mod1 (single base substitution) and BP1 Mod2 (double base substitution). Base substitutions are underlined. FIG. 12E illustrates data demonstrating that there is a drop in peripheral white blood cell and platelet counts associated with administration of immunostimulatory siRNA and this is ameliorated by RNA sequence modifications.

FIG. 14 illustrates data demonstrating that freshly isolated monocytes can be stimulated with lipid-complexed siRNA or polycation-complexed siRNA to produce inflammatory cytokines.

FIG. 15 illustrates data demonstrating that the immunostimulatory activity of siRNA is not caused by contaminants such as ssRNA.

FIG. 16 is Table 3 which sets forth certain siRNA sequences (SEQ ID NOS: 82-93) used in the experiments described herein.

FIG. 17 illustrates data demonstrating that siRNA can be designed that are active in mediating RNAi and have minimal capacity to activate innate immune responses. FIG. 17A is Table 4 which sets forth siRNA sequences (SEQ ID NOS: 94-101) designed to target β-gal (codon start sites 478, 924, and 2891) that lack putative immunostimulatory motifs.

DETAILED DESCRIPTION OF THE INVENTION

I. Introduction

Figure 1:
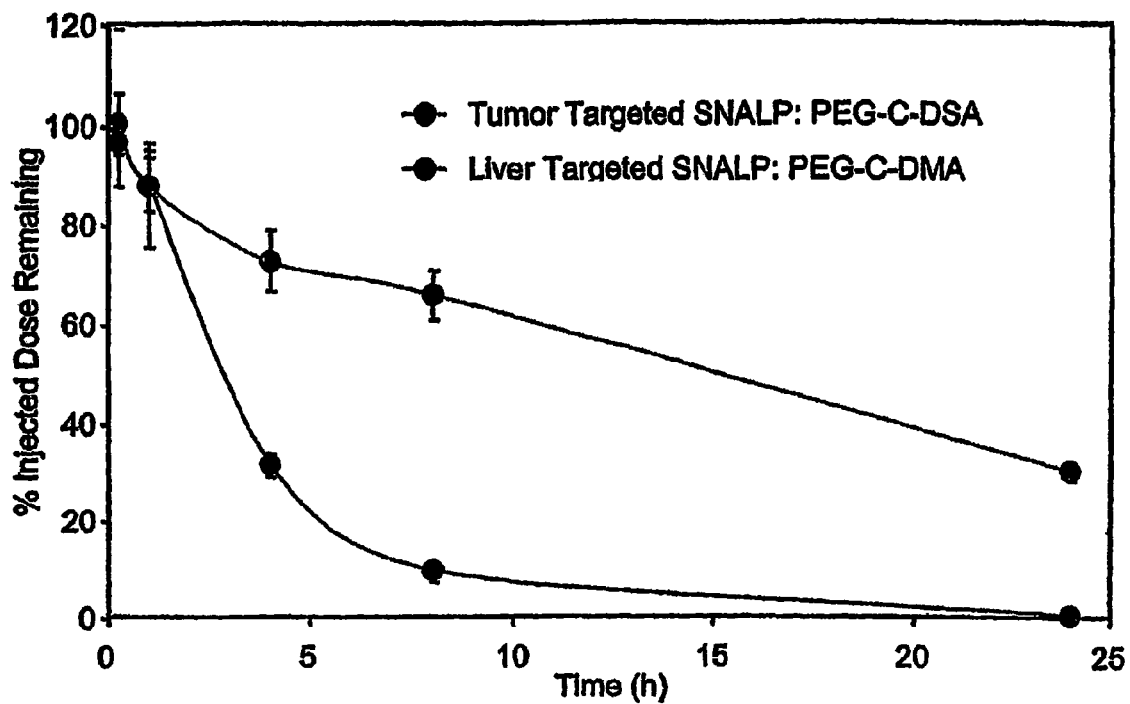
FIG. 1 illustrates data demonstrating that SNALP encapsulating siRNA exhibit extended blood circulation times.

The present invention is based, in part, on the surprising discovery that siRNA molecules have immunostimulatory effects that can be modulated. In particular, the invention is based on the discovery that siRNA molecules comprising GU-rich motifs (e.g., siRNA molecules comprising, a 5'-GU-3' motif, a 5'-UG-3' motif, a 5'-UGU-3' motif, a 5'-GUGU-3' motif, or a 5'-UGUGU-3' motif) have immunostimulatory properties. Based on this discovery, the invention provides methods and compositions for enhancing or decreasing the immune response associated with siRNA molecules as well as methods for identifying siRNA molecules with immunostimulatory properties or non-immunostimulatory properties.

For example the immunostimulatory properties of an siRNA molecule comprising a GU-rich motif can be decreased by substituting one more of the G's or one or more of the U's with another nucleotide. Likewise, the immunostimulatory properties of an siRNA molecule can be increased by a substitution or substitutions that introduce a GU-rich motif into the siRNA sequence. In addition, the immunostimulatory properties of an siRNA molecule comprising a GU-rich motif can be increased by a substitution or substitutions that introduce further GU-rich motifs into the sequence. Alternatively, an siRNA that is not immunostimulatory may be modified so that it is immunostimulatory by a substitution that introduces a GU-rich motif into the siRNA sequence.

Without being bound by theory, it is postulated that the siRNA molecules' immunostimulatory activity is mediated by Toll-Like Receptor mediated signaling. These findings have significant implications for the clinical development of RNAi as a novel therapeutic approach and in the interpretation of specific gene silencing effects using siRNA. For example, immunostimulatory siRNAs can be modified to disrupt a GU-rich motif, thus reducing their immunostimulatory properties while retaining their ability to silence a target gene. Alternatively, the immunostimulatory siRNAs can be used to generate controlled, transient cytokine production, activated T cell and NK cell proliferation, tumor-specific CTL responses, non-gene specific tumor regression, and B cell activation (i.e., antibody production). In addition, non-immunostimulatory siRNAs can be modified to comprise a GU-rich motif, thus enhancing their immunostimulatory properties while retaining their ability to silence a target gene.

II. Definitions

The term "interfering RNA" or "RNAi" or "interfering RNA sequence" refers to double-stranded RNA (i.e., duplex RNA) that is capable of reducing or inhibiting expression of a target gene (i.e., by mediating the degradation of mRNAs which are complementary to the sequence of the interfering RNA) when the interfering RNA is in the same cell as the target gene. Interfering RNA thus refers to the double stranded RNA formed by two complementary strands or by a single, self-complementary strand. Interfering RNA may have has substantial or complete identity to the target gene or may comprise a region of mismatch (i.e., a mismatch motif). The sequence of the interfering RNA can correspond to the full length target gene, or a subsequence thereof. Interfering RNA includes small-interfering RNA" or "siRNA," i.e., interfering RNA of about 15-60, 15-50, 15-50, or 15-40 (duplex) nucleotides in length, more typically about, 15-30, 15-25 or 19-25 (duplex) nucleotides in length, and is preferably about 19-25 (duplex) nucleotides in length, and is preferably about 20-24 or about 21-22 or 21-23 (duplex) nucleotides in length (e.g., each complementary sequence of the double stranded siRNA is 15-60, 15-50, 15-50, 15-40, 15-30, 15-25 or 19-25 nucleotides in length, preferably about 20-24 or about 21-22 or 21-23 nucleotides in length, and the double stranded siRNA is about 15-60, 15-50, 15-50, 15-40, 15-30, 15-25 or 19-25 preferably about 20-24 or about 21-22 or 21-23 base pairs in length). siRNA duplexes may comprise 3' overhangs of about 1 to about 4 nucleotides, preferably of about 2 to about 3 nucleotides and 5' phosphate termini. The siRNA can be chemically synthesized or may be encoded by a plasmid (e.g., transcribed as sequences that automatically fold into duplexes with hairpin loops). siRNA can also be generated by cleavage of longer dsRNA (e.g., dsRNA greater than about 25 nucleotides in length) with the *E coli* RNase III or Dicer. These enzymes process the dsRNA into biologically active siRNA (see, e.g., Yang et al., *PNAS USA* 99: 9942-7 (2002); Calegari et al., *PNAS USA* 99: 14236 (2002); Byrom et al., *Ambion TechNotes* 10(1): 4-6 (2003); Kawasaki et al., *Nucleic Acids Res.* 31: 981-7 (2003); Knight and Bass, *Science* 293: 2269-71 (2001); and Robertson et al., *J. Biol. Chem.* 243: 82 (1968)). Preferably, dsRNA are at least 50 nucleotides to about 100, 200, 300, 400 or 500 nucleotides in length. A dsRNA may be as long as 1000, 1500, 2000, 5000 nucleotides in length, or longer. The dsRNA can encode for an entire gene transcript or a partial gene transcript.

As used herein, the term "mismatch motif" or "mismatch region" refers to a portion of an siRNA sequence that does not have 100% complementarity to its target sequence. An siRNA may have at least one, two, three, four, five, six, or more mismatch regions. The mismatch regions may be contiguous or may be separated by 1, 2, 3, 4, 5, 6, 7, 8, 9, 10, 11, 12 or more nucleotides. The mismatch motifs or regions may comprise a single nucleotide or may comprise two, three, four, five, or more nucleotides. The mismatch motifs or regions may be immunostimulatory or non-immunostimulatory. An immunostimulatory mismatch motif or region is a GU-rich motif (e.g., 5'-GU-3' motif, a 5'-UG-3' motif, a 5'-UGU-3' motif, a 5'-GUGU-3' motif, or a 5'-UGUGU-3' motif). A non-immunostimulatory mismatch motif or region lacks a GU-rich motif.

An "effective amount" or "therapeutically effective amount" of an siRNA is an amount sufficient to produce the desired effect, e.g., a inhibition of expression of a target sequence in comparison to the normal expression level detected in the absence of the siRNA, or e.g., an increase or decrease in the immune response in comparison to the normal level detected in the absence of the siRNA. Inhibition of expression of a target gene or target sequence is achieved when the value obtained with the construct relative to the control is about 90%, 80%, 70%, 60%, 50%, 40%, 30%, 25%, 20%, 15%, 10%, 5%, or 0%. Suitable assays for measuring expression of a target gene or target sequence include, e.g., examination of protein or mRNA levels using techniques known to those of skill in the art such as dot blots, northern blots, in situ hybridization, ELISA, immunoprecipitation, enzyme function, as well as phenotypic assays known to those of skill in the art.

By "increase" or "increasing" of an immune response by an siRNA is intended to mean a detectable increase of an immune response to the siRNA (e.g., a modified or unmodified siRNA comprising a GU-rich motif). The amount of increase of an immune response by of a modified or unmodified siRNA comprising a GU-rich motif may be determined relative to the level of an immune response that is detected in the absence of the siRNA. The amount of increase of an immune response by a modified siRNA comprising a GU-rich motif may also be determined relative to the level of an immune response in the presence of an unmodified siRNA (e.g., an unmodified siRNA lacking a GU-rich motif). A detectable increase can be about 5%, 10%, 20%, 30%, 40%, 50%, 60%, 70%, 80%, 90%, 100%, or more higher than the immune response detected in the absence of the siRNA (e.g., a modified or unmodified siRNA comprising a GU-rich motif). An increase in the immune response to siRNA is typically measured by an increase in cytokine production (e.g., IFNγ, IFNα, TNFα, IL-6, or IL-12) by a responder cell in vitro or an increase in cytokine production in the sera of a mammalian subject after administration of the siRNA.

By "decrease" or "decreasing" of an immune response by an siRNA is intended to mean a detectable decrease of an immune response to siRNA (e.g., a modified siRNA lacking a GU-rich motif). The amount of decrease of an immune response by a modified siRNA lacking a GU-rich motif may be determined relative to the level of an immune response in the presence of an unmodified siRNA (e.g., an unmodified siRNA comprising a GU-rich motif). A detectable decrease can be about 5%, 10%, 20%, 30%, 40%, 50%, 60%, 70%, 80%, 90%, 100% or more lower than the immune response detected in the absence of the unmodified siRNA (e.g., an unmodified siRNA comprising a GU-rich motif). An increase in the immune response to siRNA is typically measured by an increase in cytokine production (e.g., IFNγ, IFNα, TNFα, IL-6, or IL-12) by a responder cell in vitro or an increase in cytokine production in the sera of a mammalian subject after administration of the siRNA.

As used herein, the term "responder cell" refers to a cell, preferable a mammalian cell, that produces a detectable immune response when contacted with an immunostimulatory double stranded RNA. Exemplary responder cells include, e.g., dendritic cells, macrophages, peripheral blood mononuclear cells, splenocytes, and the like. Detectable immune responses include, e.g., production of cytokines such as IFN-α, IFN-γ, TNF-α, IL-1, IL-2, IL-3, 11-4, IL-5, IL-6, IL-10, IL-12, IL-13, and TGF.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which an siRNA will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. New York).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

The terms "substantially identical" or "substantial identity," in the context of two or more nucleic acids, refer to two or more sequences or subsequences that are the same or have a specified percentage of nucleotides that are the same (i.e., at least about 60%, preferably 65%, 70%, 75%, preferably 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 75, or 100 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "nucleic acid" or "polynucleotide" refers to a polymer containing at least two deoxyribonucleotides or ribonucleotides in either single- or double-stranded form and include DNA and RNA. DNA may be in the form of, e.g., antisense oligonucleotides, plasmid DNA, pre-condensed DNA, a PCR product, vectors (P1, PAC, BAC, YAC, artificial chromosomes), expression cassettes, chimeric sequences, chromosomal DNA, or derivatives and combinations of these groups. RNA may be in the form of siRNA, mRNA, tRNA, rRNA, tRNA, vRNA, and combinations thereof. Unless specifically limited, the terms encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are characterized by being insoluble in water, but soluble in many organic solvents. They are usually divided into at least three classes: (1) "simple lipids which include fats and oils as well as waxes; (2) "compound lipids" which include phospholipids and glycolipids; (3) "derived lipids" such as steroids.

"Lipid vesicle" refers to any lipid composition that can be used to deliver a compound including, but not limited to, liposomes, wherein an aqueous volume is encapsulated by an amphipathic lipid bilayer; or wherein the lipids coat an interior comprising a large molecular component, such as a plasmid comprising an interfering RNA sequence, with a reduced aqueous interior; or lipid aggregates or micelles, wherein the encapsulated component is contained within a relatively disordered lipid mixture.

As used herein, "lipid encapsulated" can refer to a lipid formulation that provides a compound, such as siRNA, with full encapsulation, partial encapsulation, or both. In a preferred embodiment, the nucleic acid is fully encapsulated in the lipid formulation (e.g., to form an SPLP, pSPLP, SNALP, or other nucleic acid-lipid particle).

The nucleic acid-lipid particles of the present invention typically have a mean diameter of about 50 nm to about 150 nm, more typically about 100 nm to about 130 nm, most typically about 110 nm to about 115 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in U.S. Pat. Nos. 5,976,567; 5,981,501; 6,534,484; 6,586,410; 6,815,432; and WO 96/40964.

Various suitable cationic lipids may be used in the present invention, either alone or in combination with one or more other cationic lipid species or non-cationic lipid species.

The cationic lipids described herein typically carry a net positive charge at a selected pH, such as physiological pH. It has been surprisingly found that cationic lipids comprising alkyl chains with multiple sites of unsaturation, e.g., at least two or three sites of unsaturation, are particularly useful for forming nucleic acid-lipid particles with increased membrane fluidity. A number of cationic lipids and related analogs, which are also useful in the present invention, have been described in U.S. Patent Application Nos. 60/578,075 and 60/610,746; U.S. Pat. Nos. 5,753,613; 5,208,036, 5,264,618, 5,279,833 and 5,283,185, and WO 96/10390.

The non-cationic lipids used in the present invention can be any of a variety of neutral uncharged, zwitterionic or anionic lipids capable of producing a stable complex. They are preferably neutral, although they can alternatively be positively or negatively charged. Examples of non-cationic lipids useful in the present invention include: phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE). Non-cationic lipids or sterols such as cholesterol may be present. Additional nonphosphorous containing lipids are, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide and the like, diacylphosphatidylcholine, diacylphosphatidylethanolamine, ceramide, sphingomyelin, cephalin, and cerebrosides. Other lipids such as lysophosphatidylcholine and lysophosphatidylethanolamine may be present. Non-cationic lipids also include polyethylene glycol-based polymers such as PEG 2000, PEG 5000 and polyethylene glycol conjugated to phospholipids or to ceramides (referred to as PEG-Cer), as described in U.S. Pat. No. 5,820,873.

In preferred embodiments, the non-cationic lipids are diacylphosphatidylcholine (e.g., distearoylphosphatidylcholine, dioleoylphosphatidylcholine, dipalmitoylphosphatidylcholine and dilinoleoylphosphatidylcholine), diacylphosphatidylethanolamine (e.g., dioleoylphosphatidylethanolamine and palmitoyloleoylphosphatidylethanolamine), ceramide or sphingomyelin. The acyl groups in these lipids are preferably acyl groups derived from fatty acids having $C_{10}$-$C_{24}$ carbon chains. More preferably the acyl groups are lauroyl, myristoyl, palmitoyl, stearoyl or oleoyl. In particularly preferred embodiments, the non-cationic lipid will be cholesterol, 1,2-sn-dioleoylphosphatidylethanolamine, or egg sphingomyelin (ESM).

In addition to cationic and non-cationic lipids, the SPLPs of the present invention comprise bilayer stabilizing component (BSC) such as an ATTA-lipid or a PEG-lipid, such as PEG coupled to dialkyloxypropyls (PEG-DAA) (see, copending U.S. patent application Ser. No. 10/942,379), PEG coupled to diacylglycerol (PEG-DAG) (see, copending U.S. patent application Ser. No. 10/136,707), PEG coupled to phosphatidylethanolamine (PE) (PEG-PE) or some other phospholipid, or PEG conjugated to ceramides (PEG-Cer), or a mixture thereof (see, U.S. Pat. No. 5,885,613). In one preferred embodiment, the BSC is a conjugated lipid that inhibits aggregation of the SPLPs. Suitable conjugated lipids include, but are not limited to, PEG-lipid conjugates, ATTA-lipid conjugates, cationic-polymer-lipid conjugates (CPLs) or mixtures thereof. In one preferred embodiment, the SPLPs comprise either a PEG-lipid conjugate or an ATTA-lipid conjugate together with a CPL.

PEG is a polyethylene glycol, a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. as well as other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S—NHS), monomethoxypolyethylene glycol-amine (MePEG-NH$_2$), monomethoxypolyethylene glycol-tresylate (MePEG-TRES), and monomethoxypolyethylene glycol-imidazolyl-carbonyl (MePEG-IM). In addition, monomethoxypolyethyleneglycol-acetic acid (MePEG-CH$_2$COOH), is particularly useful for preparing the PEG-lipid conjugates including, e.g., PEG-DAA conjugates.

In a preferred embodiment, the PEG has an average molecular weight of from about 1000 to about 5000 daltons, more preferably, from about 1,000 to about 3,000 daltons and, even more preferably, of about 2,000 daltons. The PEG can be optionally substituted by an alkyl, alkoxy, acyl or aryl group. PEG can be conjugated directly to the lipid or may be linked to the lipid via a linker moiety. Any linker moiety suitable for coupling the PEG to a lipid can be used including, e.g., non-ester containing linker moieties and ester-containing linker moieties.

As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, etc. as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

As used herein, the term "SNALP" refers to a stable nucleic acid-lipid particle, including SPLP. A SNALP represents a lipid vesicle oencapsulating a nucleic acid (e.g., ssDNA, dsDNA, ssRNA, dsRNA, siRNA, or a plasmid, including plasmids from which an interfering RNA is transcribed). As used herein, the term "SPLP" refers to a nucleic acid-lipid particle comprising a nucleic acid (e.g., a plasmid) encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection, accumulate at distal sites (e.g., sites physically separated from the administration site) and can mediate expression of the transfected gene at these distal sites. SPLPs include "pSPLP" which comprise an encapsulated condensing agent-nucleic acid complex as set forth in WO 00/03683.

The term "vesicle-forming lipid" is intended to include any amphipathic lipid having a hydrophobic moiety and a polar head group, and which by itself can form spontaneously into bilayer vesicles in water, as exemplified by most phospholipids.

The term "vesicle-adopting lipid" is intended to include any amphipathic lipid that is stably incorporated into lipid bilayers in combination with other amphipathic lipids, with its hydrophobic moiety in contact with the interior, hydrophobic region of the bilayer membrane, and its polar head group moiety oriented toward the exterior, polar surface of the membrane. Vesicle-adopting lipids include lipids that on their own tend to adopt a nonlamellar phase, yet which are capable of assuming a bilayer structure in the presence of a bilayer-stabilizing component. A typical example is DOPE (dioleoylphosphatidylethanolamine). Bilayer stabilizing components include, but are not limited to, conjugated lipids that inhibit aggregation of nucleic acid-lipid particles, polyamide oligomers (e.g., ATTA-lipid derivatives), peptides, proteins, detergents, lipid-derivatives, PEG-lipid derivatives such as PEG coupled to dialkyloxypropyls, PEG coupled to diacylglycerols, PEG coupled to phosphatidyl-ethanolamines, PEG conjugated to ceramides (see, U.S. Pat. No. 5,885,613); cationic PEG lipids, and mixture thereof.

The term "amphipathic lipid" refers, in part, to any suitable material wherein the hydrophobic portion of the lipid material orients into a hydrophobic phase, while the hydrophilic portion orients toward the aqueous phase. Amphipathic lipids are usually the major component of a lipid vesicle. Hydrophilic characteristics derive from the presence of polar or charged groups such as carbohydrates, phosphate, carboxylic, sulfato, amino, sulfhydryl, nitro, hydroxy and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of amphipathic compounds include, but are not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Other compounds lacking in phosphorus, such as sphingolipid, glycosphingolipid families, diacylglycerols and .beta.-acyloxyacids, are also within the group designated as amphipathic lipids. Additionally, the amphipathic lipid described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides and diacylglycerols.

The term "non-cationic lipid" refers to any neutral lipid as described above as well as anionic lipids.

The term "anionic lipid" refers to any lipid that is negatively charged at physiological pH. These lipids include, but are not limited to, phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "cationic lipid" refers to any of a number of lipid species that carry a net positive charge at a selected pH, such as physiological pH. Such lipids include, but are not limited to, N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleoyloxy) propyl)-N,N,N-trimethylammonium chloride ("DOTAP"); 3-(N-(N',N'-dimethylaminoethane)-carbamoyl)cholesterol ("DC-Chol"); N-(1,2-dimyristyloxyprop-3-yl)-N,N-dimethyl-N-hydroxyethyl ammonium bromide ("DMRIE"); 1,2-DiLinoleyloxy-N,N-dimethylaminopropane (DLinDMA); and 1,2-Dilinolenyloxy-N,N-dimethylaminopropane (DLenDMA). The following lipids are cationic and have a positive charge at below physiological pH: DODAP, DODMA, DMDMA and the like.

The term "hydrophobic lipid" refers to compounds having apolar groups that include, but are not limited to, long chain saturated and unsaturated aliphatic hydrocarbon groups and such groups optionally substituted by one or more aromatic, cycloaliphatic or heterocyclic group(s). Suitable examples include, but are not limited to, diacylglycerol, dialkylglycerol, N-N-dialkylamino, 1,2-diacyloxy-3-aminopropane and 1,2-dialkyl-3-aminopropane.

The term "fusogenic" refers to the ability of a liposome, an SNALP or other drug delivery system to fuse with membranes of a cell. The membranes can be either the plasma membrane or membranes surrounding organelles, e.g., endosome, nucleus, etc.

The term "diacylglycerol" refers to a compound having 2-fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Diacylglycerols have the following general formula:

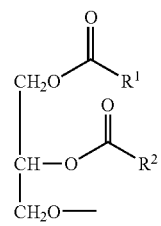

The term "dialkyloxypropyl" refers to a compound having 2-alkyl chains, $R^1$ and $R^2$, both of which have independently between 2 and 30 carbons. The alkyl groups can be saturated or have varying degrees of unsaturation. Dialkyloxypropyls have the following general formula:

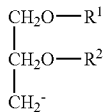

The term "ATTA" or "polyamide" refers to, but is not limited to, compounds disclosed in U.S. Pat. Nos. 6,320,017 and 6,586,559. These compounds include a compound having the formula

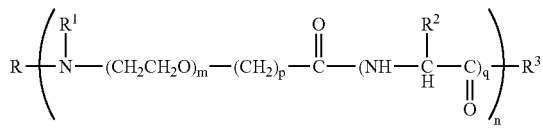

wherein: R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles means that the particle is not significantly degraded after exposure to a serum or nuclease assay that would significantly degrade free DNA. Suitable assays include, for example, a standard serum assay or a DNAse assay such as those described in the Examples below.

"Systemic delivery," as used herein, refers to delivery that leads to a broad biodistribution of a compound within an organism. Some techniques of administration can lead to the systemic delivery of certain compounds, but not others. Systemic delivery means that a useful, preferably therapeutic, amount of a compound is exposed to most parts of the body. To obtain broad biodistribution generally requires a blood lifetime such that the compound is not rapidly degraded or cleared (such as by first pass organs (liver, lung, etc.) or by rapid, nonspecific cell binding) before reaching a disease site distal to the site of administration. Systemic delivery of nucleic acid-lipid particles can be by any means known in the art including, for example, intravenous, subcutaneous, intraperitoneal, In a preferred embodiment, systemic delivery of nucleic acid-lipid particles is by intravenous delivery.

"Local delivery," as used herein, refers to delivery of a compound directly to a target site within an organism. For example, a compound can be locally delivered by direct injection into a disease site such as a tumor or other target site such as a site of inflammation or a target organ such as the liver, heart, pancreas, kidney, and the like.

III. siRNAs

The siRNA of the invention are capable of silencing expression of a target sequence, are about 15 to 30 nucleotides in length, and comprise at least one mismatch motif relative to a target nucleic acid sequence. The mismatch motif may be immunostimulatory (i.e., GU-rich) or may be non-immunostumulatory. The siRNAs that are immunostimulatory comprise one or more GU-rich motifs (e.g, a 5'-GU-3' motif, a 5'-UG-3' motif, a 5'-UGU-3' motif, a 5'-GUGU-3' motif, or a 5'-UGUGU-3' motif). The siRNA which are not immunostimulatory may comprise one or are less immunostimulatory may comprise one GU-rich motif, but will typically not comprise such motifs. The siRNA sequences may have overhangs (e.g., 3' or 5' overhangs as described in (Elbashir, et al., *Genes Dev.* 15:188 (2001); Nykänen, et al., *Cell* 107:309 (2001)) or may lack overhangs (i.e., have blunt ends).

According to the methods of the invention, siRNA which are immunostimulatory can be modified to decrease their immunostimulatory properties. For example, an immunostimulatory siRNA comprising a GU-rich motif can be modified to disrupt or eliminate the motif, i.e., by replacing one or more of the G's or one or more of the U's in the GU-rich motif with another nucleotide, thus generating an siRNA with reduced immunostimulatory properties. Alternatively, siRNA which are not immunostimulatory can be modified to add a GU-rich motif, i.e., by substitution of a nucleotide with a G or a U, thus generating an siRNA with enhanced immunostimulatory properties. In a preferred embodiment, siRNA which are immunostimulatory are modified to decrease their immunostimulatory properties, e.g., to disrupt a GU-rich motif.

The siRNA molecules described herein typically comprise at least one mismatch region (e.g., an immunostimulatory mismatch region or a non-immunostimulatory mismatch region) with its target sequence. An siRNA molecule is modified to either enhance its immunostimulatory properties or to decrease its immunostimulatory properties. For example, an siRNA molecule modified to reduce its immunostimulatory properties is typically modified to comprise at least one non-immunostimulatory mismatch region relative to its target sequence. In contrast, an siRNA modified to enhance its immunostimulatory properties is typically modified to comprise at least one immunostimulatory mismatch region relative to its target sequence.

A. Selection of siRNA sequences

Suitable siRNA sequences can be identified using any means known in the art. Typically, the methods described in Elbashir, et al., *Nature* 411:494-498 (2001) and Elbashir, et al., *EMBO J* 20: 6877-6888 (2001) are combined with rational design rules set forth in Reynolds et al., *Nature Biotech.* 22(3):326-330 (2004).

Typically, the sequence within about 50 to about 100 nucleotides 3' of the AUG start codon of a transcript from the target gene of interest is scanned for dinucleotide sequences (e.g., AA, CC, GG, or UU) (see, e.g., Elbashir, et al., *EMBO J* 20: 6877-6888 (2001)). The nucleotides immediately 3' to the dinucleotide sequences are identified as potential siRNA target sequences. Typically, the 19, 21, 23, 25, 27, 29, 31, 33, 35 or more nucleotides immediately 3' to the dinucleotide sequences are identified as potential siRNA target sites. In some embodiments, the dinucleotide sequence is an AA sequence and the 19 nucleotides immediately 3' to the AA dinucleotide are identified as a potential siRNA target site. Typically siRNA target sites are spaced at different postitions along the length of the target gene. To further enhance silencing efficiency of the siRNA sequences, potential siRNA target sites may be further analyzed to identify sites that do not contain regions of homology to other coding sequences. For example, a suitable siRNA target site of about 21 base pairs typically will not have more than 16-17 contiguous base pairs of homology to other coding sequences. If the siRNA sequences are to be expressed from an RNA Pol III promoter, siRNA target sequences lacking more than 4 contiguous A's or T's are selected.

Once the potential siRNA target site has been identified siRNA sequences complementary to the siRNA target sites may be designed. To enhance their silencing efficiency, the siRNA sequences may also be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features are useful for selection of siRNA.

Once a potential siRNA sequence has been identified, the sequence can be analyzed for the presence of GU-rich motifs (e.g., 5'-GU-3', 5'-UGU-3', 5'-GUGU-3', or 5'-UGUGU-3' motifs. Potential siRNA target sequences that contain GU-rich motifs are identified as immunustimulatory siRNAs. Potential siRNA target sequences that lack GU-rich motifs are identified as non-immunustimulatory siRNAs. In some embodiments, potential siRNA target sequences comprising GU-rich motifs are modified as described herein to eliminate the motifs and reduce the immunostimulatory properties of the sequences. In other embodiments, potential siRNA target sequences lacking GU-rich motifs are modified as described herein to introduce the motifs and increase the immunostimulatory properties of the sequences. The immunostimulatory properties of the potential siRNA target sequences can be confirmed using the assays described in detail below.

One embodiment of the invention provides methods of identifying siRNA molecules that are immunostimulatory or non-immunostimulatory. Once identified, the immunostimulatory siRNA molecules can be modified to increase or decrease their immunostimulatory properties and the non-immunostimulatory molecules can be modified so that they possess immunostimulatory properties In this embodiment, a target nucleic acid sequence is analyzed for the presence of an immunostimulatory motif, e.g., a GU-rich motif. If an immunostimulatory motif is present, a double stranded RNA (i.e., siRNA) sequence having immunostimulatory properties is identified. If no immunostimulatory motif is present, a double stranded RNA (i.e., siRNA) sequence having non-immunostimulatory properties is identified. The siRNA is then selected and contacted with a mammalian responder cell under conditions such that the cell produces a detectable immune response, thus confirming that the siRNA is an immunostimulatory or a non-immunostimulatory siRNA. The mammalian responder cell may be from a naive mammal (i.e., a mammal that has not previously been in contact with the gene product of the target nucleic acid sequence). The responder cell may be, e.g., a peripheral blood mononuclear cell, a macrophage, and the like. The detectable immune response may comprise production of a cytokine or growth factor such as, e.g., TNF-α, IFN-α, IL-6, IL-12, and combinations thereof.

Suitable assays to detect an immune response induced by immunostimulatory siRNA include the double monoclonal antibody sandwich immunoassay technique of David et al. U.S. Pat. No. 4,376,110); monoclonal-polyclonal antibody sandwich assays (Wide et al., in Kirkham and Hunter, eds., Radioimmunoassay Methods, E. and S. Livingstone, Edinburgh (1970)); the "western blot" method of Gordon et al. (U.S. Pat. No. 4,452,901); immunoprecipitation of labeled ligand (Brown et al. (1980) J. Biol. Chem. 255:4980-4983); enzyme-linked immunosorbent assays (ELISA) as described, for example, by Raines et al. (1982) J. Biol. Chem. 257:5154-5160; immunocytochemical techniques, including the use of fluorochromes (Brooks et al. (1980) Clin. Exp. Immunol. 39:477); and neutralization of activity (Bowen-Pope et al. (1984) Proc. Natl. Acad. Sci. USA 81:2396-2400). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876.

Monoclonal antibodies that specifically bind cytokines and growth factors (e.g., Il-6, IL-12, TNF-A, IFN-α, and IFN-α are commercially available from multiple sources and can be generated using methods known in the art (see, e.g., Kohler and Milstein, Nature 256: 495-497 (1975) and Harlow and Lane, ANTIBODIES, A LABORATORY MANUAL, Cold Spring Harbor Publication, New York (1999)). Generation of monoclonal antibodies has been previously described and can be accomplished by any means known in the art. (Buhring et al. in Hybridoma 1991, Vol. 10, No. 1, pp. 77-78). In some methods, the monoclonal antibody is labeled (e.g., with any composition detectable by spectroscopic, photochemical, biochemical, electrical, optical or chemical means) to facilitate detection.

B. Generating siRNA siRNA can be provided in several forms including, e.g., as one or more isolated small-interfering RNA (siRNA) duplexes, longer double-stranded RNA (dsRNA) or as siRNA or dsRNA transcribed from a transcriptional cassette in a DNA plasmid. siRNA may also be chemically synthesized. Preferably, the synthesized or transcribed siRNA have 3' overhangs of about 1-4 nucleotides, preferably of about 2-3 nucleotides and 5' phosphate termini. The siRNA sequences may have overhangs (e.g., 3' or 5' overhangs as described in (Elbashir, et al., Genes Dev. 15:188 (2001); Nykanen, et al., Cell 107:309 (2001)) or may lack overhangs (i.e., to have blunt ends).

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned CDNA); or chemically synthesized.

To form a long dsRNA, for synthetic RNAs, the complement is also transcribed in vitro and hybridized to form a dsRNA. If a naturally occuring RNA population is used, the RNA complements are also provided (e.g., to form dsRNA for digestion by E. coli RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Alternatively, one or more DNA plasmids encoding one or more siRNA templates are used to provide siRNA. siRNA can be transcribed as sequences that automatically fold into duplexes with hairpin loops from DNA templates in plasmids having RNA polymerase III transcriptional units, for example, based on the naturally occurring transcription units for small nuclear RNA U6 or human RNase P RNA H1 (see, Brummelkamp, et al., *Science* 296:550 (2002); Donzé, et al., *Nucleic Acids Res.* 30:e46 (2002); Paddison, et al., *Genes Dev.* 16:948 (2002); Yu, et al., *Proc. Natl. Acad. Sci.* 99:6047 (2002); Lee, et al., *Nat. Biotech.* 20:500 (2002); Miyagishi, et al., *Nat. Biotech.* 20:497 (2002); Paul, et al., *Nat. Biotech.* 20:505 (2002); and Sui, et al., *Proc. Natl. Acad. Sci.* 99:5515 (2002)). Typically, a transcriptional unit or cassette will contain an RNA transcript promoter sequence, such as an H1-RNA or a U6 promoter, operably linked to a template for transcription of a desired siRNA sequence and a termination sequence, comprised of 2-3 uridine residues and a polythymidine (T5) sequence (polyadenylation signal) (Brummelkamp, *Science*, supra). The selected promoter can provide for constitutive or inducible transcription. Compositions and methods for DNA-directed transcription of RNA interference molecules is described in detail in U.S. Pat. No. 6,573,099. The transcriptional unit is incorporated into a plasmid or DNA vector from which the interfering RNA is transcribed. Plasmids suitable for in vivo delivery of genetic material for therapeutic purposes are described in detail in U.S. Pat. Nos. 5,962,428 and 5,910,488. The selected plasmid can provide for transient or stable delivery of a target cell. It will be apparent to those of skill in the art that plasmids originally designed to express desired gene sequences can be modified to contain a transcriptional unit cassette for transcription of siRNA.

Methods for isolating RNA, synthesizing RNA, hybridizing nucleic acids, making and screening cDNA libraries, and performing PCR are well known in the art (see, e.g., Gubler & Hoffman, *Gene* 25:263-269 (1983); Sambrook et al., supra; Ausubel et al., supra), as are PCR methods (see U.S. Pat. No. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

1. Target Genes

The siRNA described herein can be used to downregulate or silence the translation (i.e., expression) of a gene of interest. Genes of interest include, but are not limited to, genes associated with viral infection and survival, genes associated with metabolic diseases and disorders (e.g., liver diseases and disorders), genes associated with tumorigenesis and cell transformation, angiogenic genes, immunomodulator genes, such as those associated with inflammatory and autoimmune responses, ligand receptor genes, and genes associated with neurodegenerative disorders.

Genes associated with viral infection and survival include those expressed by a virus in order to bind, enter and replicate in a cell. Of particular interest are viral sequences associated with chronic viral diseases. Viral sequences of particular interest include sequences of Hepatitis viruses (Hamasaki, et al., *FEBS Lett.* 543:51 (2003); Yokota, et al., *EMBO Rep.* 4:602 (2003); Schlomai, et al., *Hepatology* 37:764 (2003); Wilson, et al., *Proc. Natl. Acad. Sci.* 100:2783 (2003); Kapadia, et al., *Proc. Natl. Acad. Sci.* 100:2014 (2003); and FIELDS VIROLOGY (Knipe et al. eds. 2001)), Human Immunodeficiency Virus (HIV) (Banerjea, et al., *Mol. Ther.* 8:62 (2003); Song, et al., *J. Virol.* 77:7174 (2003); Stephenson *JAMA* 289: 1494 (2003); Qin, et al., *Proc. Natl. Acad. Sci.* 100:183 (2003)), Herpes viruses (Jia, et al., *J. Virol.* 77:3301 (2003)), and Human Papilloma Viruses (HPV) (Hall, et al., *J. Virol.* 77:6066 (2003); Jiang, et al., *Oncogene* 21:6041 (2002)). Examplary hepatitis viral nucleic acid sequences that can be silenced include, but are not limited to: nucleic acid sequences involved in transcription and translation (e.g., En1, En2, X, P), nucleic acid sequences encoding structural proteins (e.g., core proteins including C and C-related proteins; capsid and envelope proteins including S, M, and/or L proteins, or fragments thereof) (see, e.g., FIELDS VIROLOGY, 2001, supra). Exemplary Hepatits C nucleic acid sequences that can be silenced include, but are not limited to: serine proteases (e.g., NS3/NS4), helicases (e.g. NS3), polymerases (e.g., NS5B), and envelope proteins (e.g., E1, E2, and p7). Hepatitis A nucleic acid sequences are set forth in e.g., Genbank Accession No. NC_001489; Hepatitis B nucleic acid sequences are set forth in, e.g., Genbank Accession No. NC_003977; Hepatitis C nucleic acid sequences are set forth in, e.g., Genbank Accession No. NC_004102; Hepatitis D nucleic acid sequence are set forth in, e.g., Genbank Accession No. NC_001653; Hepatitis E nucleic acid sequences are set forth in e.g., Genbank Accession No. NC_001434; and Hepatitis G nucleic acid sequences are set forth in e.g., Genbank Accession No. NC_001710. Silencing of sequences that encode genes associated with viral infection and survival can conveniently be used in combination with the administration of conventional agents used to treat the viral condition.

Genes associated with metabolic diseases and disorders (e.g., disorders in which the liver is the target and liver diseases and disorders) include, for example genes expressed in, for example, dyslipidemia (e.g., liver X receptors (e.g., LXRα and LXRβ Genback Accession No. NM_007121), famesoid X receptors (FXR) (Genbank Accession No. NM_005123), sterol-regulatory element binding protein (SREBP), Site-1 protease (SIP), 3-hydroxy-3-methylglutaryl coenzyme-A reductase (HMG coenzyme-A reductase), Apolipoprotein (ApoB), and Apolipoprotein (ApoE)) and diabetes (e.g., Glucose 6-phosphatase) (see, e.g., Forman et al., *Cell* 81:687 (1995); Seol et al., *Mol. Endocrinol.* 9:72 (1995), Zavacki et al., *PNAS USA* 94:7909 (1997); Sakai, et al., *Cell* 85:1037-1046 (1996); Duncan, et al., *J. Biol. Chem.* 272: 12778-12785 (1997); , Willy, et al., *Genes Dev.* 9(9):1033-45 (1995); Lehmann, et al., *J. Biol. Chem.* 272(6):3137-3140 (1997); Janowski, et al., Nature 383:728-731 (1996); Peet, et al., *Cell* 93:693-704 (1998)). One of skill in the art will appreciate that genes associated with metabolic diseases and disorders (e.g., diseases and disorders in which the liver is a target and liver diseases and disorders) include genes that are expressed in the liver itself as well as and genes expressed in other organs and tissues. Silencing of sequences that encode genes associated with metabolic diseases and disorders can conveniently be used in combination with the administration of conventional agents used to treat the disease or disorder.

Examples of gene sequences associated with tumorigenesis and cell transformation include translocation sequences such as MLL fusion genes, BCR-ABL (Wilda, et al., *Oncogene,* 21:5716 (2002); Scherr, et al., *Blood* 101:1566), TEL-AML1, EWS-FLI1, TLS-FUS, PAX3-FKHR, BCL-2, AML1-ETO and AML1-MTG8 (Heidenreich, et al., *Blood*

101:3157 (2003)); overexpressed sequences such as multidrug resistance genes (Nieth, et al., *FEBS Lett.* 545:144 (2003); Wu, et al, *Cancer Res.* 63:1515 (2003)), cyclins (Li, et al., *Cancer Res.* 63:3593 (2003); Zou, et al., *Genes Dev.* 16:2923 (2002)), beta-Catenin (Verma, et al., *Clin Cancer Res.* 9:1291 (2003)), telomerase genes (Kosciolek, et al., *Mol Cancer Ther.* 2:209 (2003)), c-MYC, N-MYC, BCL-2, ERBB1 and ERBB2 (Nagy, et al. *Exp. Cell Res.* 285:39 (2003)); and mutated sequences such as RAS (reviewed in Tuschl and Borkhardt, *Mol. Interventions,* 2:158 (2002)). Silencing of sequences that encode DNA repair enzymes find use in combination with the administration of chemotherapeutic agents (Collis, et al., *Cancer Res.* 63:1550 (2003)). Genes encoding proteins associated with tumor migration are also target sequences of interest, for example, integrins, selectins and metalloproteinases. The foregoing examples are not exclusive. Any whole or partial gene sequence that facilitates or promotes tumorigenesis or cell transformation, tumor growth or tumor migration can be included as a template sequence Angiogenic genes are able to promote the formation of new vessels. Of particular interest is Vascular Endothelial Growth Factor (VEGF) (Reich, et al., *Mol. Vis.* 9:210 (2003)) or VEGFr. siRNA sequences that target VEGFr are set forth in, e.g., GB 2396864; U.S. Patent Publication No. 20040142895; and CA2456444.

Immunomodulator genes are genes that modulate one or more immune responses. Examples of immunomodulator genes include cytokines such as growth factors (e.g., TGF-α, TGF-β, EGF, FGF, IGF, NGF, PDGF, CGF, GM-CSF, SCF, etc.), interleukins (e.g., IL-2, IL-4, IL-12 (Hill, et al., *J. Immunol.* 171:691 (2003)), IL-15, IL-18, IL-20, etc.), interferons (e.g., IFN-α, IFN-β, IFN-γ, etc.) and TNF. Fas and Fas Ligand genes are also immunomodulator target sequences of interest (Song, et al., *Nat. Med.* 9:347 (2003)). Genes encoding secondary signaling molecules in hematopoietic and lymphoid cells are also included in the present invention, for example, Tec family kinases, such as Bruton's tyrosine kinase (Btk) (Heinonen, et al., *FEBS Lett.* 527:274 (2002)).

Cell receptor ligands include ligands that are able to bind to cell surface receptors (e.g., insulin receptor, EPO receptor, G-protein coupled receptors, receptors with tyrosine kinase activity, cytokine receptors, growth factor receptors, etc.), to modulate (e.g., inhibit, activate, etc.) the physiological pathway that the receptor is involved in (e.g., glucose level modulation, blood cell development, mitogenesis, etc.). Examples of cell receptor ligands include cytokines, growth factors, interleukins, interferons, erythropoietin (EPO), insulin, glucagon, G-protein coupled receptor ligands, etc.). Templates coding for an expansion of trinucleotide repeats (e.g., CAG repeats), find use in silencing pathogenic sequences in neurodegenerative disorders caused by the expansion of trinucleotide repeats, such as spinobulbular muscular atrophy and Huntington's Disease (Caplen, et al., *Hum. Mol. Genet.* 11:175 (2002)).

IV. SPLP Containing siRNA

In one embodiment, the present invention provides stabilized nucleic acid-lipid particles (SPLPs or SNALPS) and other lipid-based carrier systems containing the siRNA described herein. As used herein, the term "SNALP" refers to a stable nucleic acid-lipid particle, including SPLP. A SNALP represents a vesicle of lipids coating a reduced aqueous interior comprising a nucleic acid (e.g., ssDNA, dsDNA, ssRNA, dsRNA, siRNA, or a plasmid, including plasmids from which an interfering RNA is transcribed). As used herein, the term "SPLP" refers to a nucleic acid-lipid particle comprising a nucleic acid (e.g., a plasmid) encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs have systemic application as they exhibit extended circulation lifetimes following intravenous (i.v.) injection, accumulate at distal sites (e.g., sites physically separated from the administration site and can mediate expression of the transfected gene at these distal sites. SPLPs include "pSPLP" which comprise an encapsulated condensing agent-nucleic acid complex as set forth in WO 00/03683.

The nucleic acid-lipid particles typically comprise cationic lipid and nucleic acids. The nucleic acid-lipid particles also preferably comprise non-cationic lipid and a bilayer stabilizing component or, more preferably, a conjugated lipid that inhibits aggregation of the nucleic acid-lipid particles. The nucleic acid-lipid particles of the present invention have a mean diameter of 50 nm to about 150 nm, more typically about 100 nm to about 130 nm, most typically about 110 nm to about 115 nm, and are substantially nontoxic. In addition, the nucleic acids when present in the nucleic acid-lipid particles of the present invention are resistant in aqueous solution to degradation with a nuclease. Such nucleic acid-lipid particles are disclosed in great detail in U.S. Pat. Nos. 5,705,385; 5,976,567; 5,981,501; 6,534,484; 6,586,410; 6,815,432; and WO 96/40964.

A. Cationic Lipids

Various suitable cationic lipids may be used in the present invention, either alone or in combination with one or more other cationic lipid species or neutral lipid species.

Cationic lipids which are useful in the present invention can be any of a number of lipid species which carry a net positive charge at physiological pH, for example: DODAC, DOTMA, DDAB, DOTAP, DOSPA, DOGS, DC-Chol and DMRIE, or combinations thereof. A number of these lipids and related analogs, which are also useful in the present invention, have been described in U.S. Pat. Nos. 5,208,036, 5,264,618, 5,279,833, 5,283,185, 5,753,613 and 5,785,992. Additionally, a number of commercial preparations of cationic lipids are available and can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA). In addition, cationic lipids of Formula I and Formula II and having the following structures and as described in U.S. Patent Application No. 60/578,075, filed Jun. 7, 2004:

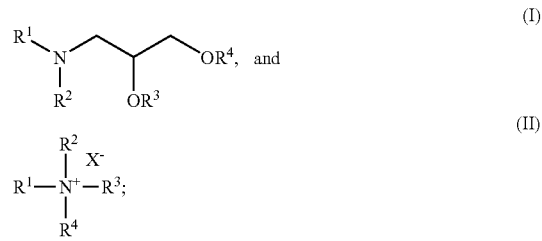

and mixtures thereof can be used in the present invention. $R^1$ and $R^2$ are independently selected and are $C_1$-$C_3$ alkyls. $R^3$ and $R^4$ are independently selected and are alkyl groups having from about 10 to about 20 carbon atoms; at least one of $R^3$ and $R^4$ comprises at least two sites of unsaturation. In one embodiment, $R^3$ and $R^4$ are both the same, i.e., $R^3$ and $R^4$ are both linoleyl (C18), etc. In another embodiment, $R^3$ and $R^4$ are different, i.e., $R^3$ is myristyl (C14) and $R^4$ is linoleyl (C18). In a preferred embodiment, the cationic lipids of the present invention are symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl.

The cationic lipid typically comprises from about 2% to about 60% of the total lipid present in the particle, preferably from about 5% to about 45% of the total lipid present in the particle. In certain preferred embodiments, the cationic lipid comprises from about 5% to about 15% of the total lipid present in the particle. In other preferred embodiments, the cationic lipid comprises from about 40% to about 50% of the total lipid present in the particle. Depending on the intended use of the nucleic acid-lipid particles, the proportions of the components are varied and the delivery efficiency of a particular formulation can be measured using an endosomal release parameter (ERP) assay. For example, for systemic delivery, the cationic lipid may comprise from about 5% to about 15% of the total lipid present in said particle and for local or regional delivery, the cationic lipid comprises from about 40% to about 50% of the total lipid present in said particle.

B. Non-cationic Lipids

The non-cationic lipids used in the present invention can be any of a variety of neutral uncharged, zwitterionic or anionic lipids capable of producing a stable complex. They are preferably neutral, although they can alternatively be positively or negatively charged. Examples of non-cationic lipids useful in the present invention include: phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE). Non-cationic lipids or sterols such as cholesterol may be present. Additional nonphosphorous containing lipids are, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide and the like, diacylphosphatidylcholine, diacylphosphatidylethanolamine, ceramide, sphingomyelin, cephalin, and cerebrosides. Other lipids such as lysophosphatidylcholine and lysophosphatidylethanolamine may be present. Non-cationic lipids also include polyethylene glycol-based polymers such as PEG 2000, PEG 5000 and polyethylene glycol conjugated to phospholipids or to ceramides (referred to as PEG-Cer), as described in U.S. Pat. No. 5,820,873.

In preferred embodiments, the non-cationic lipids are diacylphosphatidylcholine (e.g., distearoylphosphatidylcholine, dioleoylphosphatidylcholine, dipalmitoylphosphatidylcholine and dilinoleoylphosphatidylcholine), diacylphosphatidylethanolamine (e.g., dioleoylphosphatidylethanolamine and palmitoyloleoylphosphatidylethanolamine), ceramide or sphingomyelin. The acyl groups in these lipids are preferably acyl groups derived from fatty acids having $C_{10}$-$C_{24}$ carbon chains. More preferably the acyl groups are lauroyl, myristoyl, palmitoyl, stearoyl or oleoyl. In particularly preferred embodiments, the non-cationic lipid will include one or more of cholesterol, 1,2-sn-dioleoylphosphatidylethanolamine, or egg sphingomyelin (ESM).

The non-cationic lipid typically comprises from about 5% to about 90% of the total lipid present in the particle, preferably from about 20% to about 85% of the total lipid present in tje particle. The nucleic acid-lipid particles of the present invention may further comprise a sterol (e.g., cholesterol). If present, the cholesterol typically comprises from about 10% to about 60% of the total lipid present in the particle, preferably the cholesterol comprises from about 20% to about 45% of the total lipid present in the particle.

C. Bilayer Stabilizing Components

In one embodiment, the nucleic acid-lipid particle (e.g., SPLP, or SNLAP) further comprises a bilayer stabilizing component (BSC) (i.e., a conjugated lipid that prevents aggregation of particles). Bilayer stabilizing Suitable BSCs include, but are not limited to, polyamide oligomers, peptides, proteins, detergents, lipid-derivatives, PEG-lipids, such as PEG coupled to dialkyloxypropyls (PEG-DAA), PEG coupled to diacylglycerol (PEG-DAG), PEG coupled to phosphatidylethanolamine (PE) (PEG-PE), or PEG conjugated to ceramides (PEG-Cer), or a mixture thereof (see, U.S. Pat. No. 5,885,613). In one embodiment, the bilayer stabilizing component is a PEG-lipid, or an ATTA-lipid. In one preferred embodiment, the BSC is a conjugated lipid that inhibits aggregation of the SNALPs. Suitable conjugated lipids include, but are not limited to PEG-lipid conjugates, ATTA-lipid conjugates, cationic-polymer-lipid conjugates (CPLs) or mixtures thereof. In one preferred embodiment, the SNALPs comprise either a PEG-lipid conjugate or an ATTA-lipid conjugate together with a CPL.

In one embodiment, the bilayer stabilizing component comprises a diacylglycerol-polyethyleneglycol conjugate, i.e., a DAG-PEG conjugate or a PEG-DAG conjugate. In a preferred embodiment, the DAG-PEG conjugate is a dilaurylglycerol ($C_{12}$)-PEG conjugate, dimyristylglycerol ($C_{14}$)-PEG conjugate (DMG), a dipalmitoylglycerol ($C_{16}$)-PEG conjugate or a distearylglycerol ($C_{18}$)-PEG conjugate (DSG). Those of skill in the art will readily appreciate that other diacylglycerols can be used in the DAG-PEG conjugates of the present invention. Suitable DAG-PEG conjugates for use in the present invention, and methods of making and using them, are disclosed in U.S. Patent Publication No. 2003/0077829, and PCT Patent Application No. CA 02/00669.

In another embodiment, the bilayer stabilizing component comprises a dialkyloxypropyl conjugate, i.e., a PEG-DAA conjugate as described in, e.g., U.S. Patent Application Nos.

60/503,329, filed Sep. 15, 2003 and Ser. No. 10/942,379, filed Sep. 15, 2004. In one preferred embodiment, the PEG-DAA conjugate has the following formula:

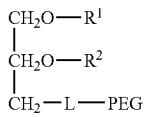
    III

In Formula III above, "$R^1$ and $R^2$" are independently selected and are saturated or unsaturated alkyl groups having from about 10 to about 20 carbon atoms; PEG is a polyethyleneglycol; and L is a non-ester-containing linker moiety as described above. Suitable alkyl groups include, but are not limited to, lauryl (C12), myristyl (C14), palmityl (C16), stearyl (C18) and icosyl (C20). In a preferred embodiment; $R^1$ and $R^2$ are the same, i.e., they are both myristyl (C14) or both palmityl (C16) or both stearyl (C18). In a preferred embodiment, the alkyl groups are saturated.

In Formula III above, "PEG" is a polyethylene glycol having an average molecular weight ranging of about 550 daltons to about 10,000 daltons, more preferably of about 750 daltons to about 5,000 daltons, more preferably of about 1,000 daltons to about 5,000 daltons, more preferably of about 1,500 daltons to about 3,000 daltons and, even more preferably, of about 2,000 daltons, or about 750 daltons. The PEG can be optionally substituted with alkyl, alkoxy, acyl or aryl. In a preferred embodiment, the terminal hydroxyl group is substituted with a methoxy or methyl group.

In Formula III, above, "L" is a non-ester containing linker moiety or an ester containing linker moiety. In a preferred embodiment, L is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In a preferred embodiment, the non-ester containing linker moiety is a succinamidyl linker moiety (i.e., a PEG-S-DAA conjugate).

Phosphatidylethanolamines having a variety of acyl chain groups of varying chain lengths and degrees of saturation can be conjugated to polyethyleneglycol to form the bilayer stabilizing component. Such phosphatidylethanolamines are commercially available, or can be isolated or synthesized using conventional techniques known to those of skill in the art. Phosphatidylethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, the following: dimyristoylphosphatidylethanolamine (DMPE), dipalmitoylphosphatidylethanolamine (DPPE), dioleoylphosphatidylethanolamine (DOPE) and distearoylphosphatidylethanolamine (DSPE).

As with the phosphatidylethanolamines, ceramides having a variety of acyl chain groups of varying chain lengths and degrees of saturation can be coupled to polyethyleneglycol to form the bilayer stabilizing component. It will be apparent to those of skill in the art that in contrast to the phosphatidylethanolamines, ceramides have only one acyl group which can be readily varied in terms of its chain length and degree of saturation. Ceramides suitable for use in accordance with the present invention are commercially available. In addition, ceramides can be isolated, for example, from egg or brain using well-known isolation techniques or, alternatively, they can be synthesized using the methods and techniques disclosed in U.S. Pat. No. 5,820,873. Using the synthetic routes set forth in the foregoing application, ceramides having saturated or unsaturated fatty acids with carbon chain lengths in the range of $C_2$ to $C_{31}$ can be prepared.

Cationic polymer lipids (CPLs) useful in the present invention have the following architectural features: (1) a lipid anchor, such as a hydrophobic lipid, for incorporating the CPLs into the lipid bilayer; (2) a hydrophilic spacer, such as a polyethylene glycol, for linking the lipid anchor to a cationic head group; and (3) a polycationic moiety, such as a naturally occurring amino acid, to produce a protonizable cationic head group. Suitable CPLs for use in the present invention, and methods of making and using nucleic acid-lipid particles comprising the CPLs, are disclosed, e.g., in U.S. Pat. No. 6,852,334; U.S. Patent Publication No. 20020072121; and WO 00/62813).

Briefly, CPL's suitable for use in the present invention include compounds of Formula IV:

    (IV)

wherein A, W and Y are as follows.

With reference to Formula IV, "A" is a lipid moiety such as an amphipathic lipid, a neutral lipid or a hydrophobic lipid that acts as a lipid anchor. Suitable lipid examples include vesicle-forming lipids or vesicle adopting lipids and include, but are not limited to, diacylglycerolyls, dialkylglycerolyls, N-N-dialkylaminos, 1,2-diacyloxy-3-aminopropanes and 1,2-dialkyl-3-aminopropanes.

"W" is a polymer or an oligomer, such as a hydrophilic polymer or oligomer. Preferably, the hydrophilic polymer is a biocompatable polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers and combinations thereof. In a preferred embodiment, the polymer has a molecular weight of about 250 to about 7000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of liposome application which is desired.

The charges on the polycationic moieties can be either distributed around the entire liposome moiety or, alternatively, they can be a discrete concentration of charge density in one particular area of the liposome moiety e.g., a charge spike. If the charge density is distributed on the liposome, the charge density can be equally distributed or unequally distributed. All variations of charge distribution of the polycationic moiety are encompassed by the present invention.

The lipid "A," and the nonimmunogenic polymer "W," can be attached by various methods and preferably, by covalent attachment. Methods known to those of skill in the art can be used for the covalent attachment of "A" and "W." Suitable linkages include, but are not limited to, amide, amine, carboxyl, carbonate, carbamate, ester and hydrazone linkages. It will be apparent to those skilled in the art that "A" and "'W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, U.S. Pat. Nos. 6,320,017 and 6,586,559), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

Typically, the bilayer stabilizing component is present ranging from about 0.5% to about 50% of the total lipid present in the particle. In a preferred embodiment, the bilayer stabilizing component is present from about 0.5% to about 25% of the total lipid in the particle. In other preferred embodiments, the bilayer stabilizing component is present from about 1% to about 20%, or about 3% to about 15% or about 4% to about 10% of the total lipid in the particle. One of ordinary skill in the art will appreciate that the concentration of the bilayer stabilizing component can be varied depending on the bilayer stabilizing component employed and the rate at which the liposome is to become fusogenic.

By controlling the composition and concentration of the bilayer stabilizing component, one can control the rate at which the bilayer stabilizing component exchanges out of the liposome and, in turn, the rate at which the liposome becomes fusogenic. For instance, when a polyethyleneglycol-phosphatidylethanolamine conjugate or a polyethyleneglycol-ceramide conjugate is used as the bilayer stabilizing component, the rate at which the liposome becomes fusogenic can be varied, for example, by varying the concentration of the bilayer stabilizing component, by varying the molecular weight of the polyethyleneglycol, or by varying the chain length and degree of saturation of the acyl chain groups on the phosphatidylethanolamine or the ceramide. In addition, other variables including, for example, pH, temperature, ionic strength, etc. can be used to vary and/or control the rate at which the liposome becomes fusogenic. Other methods which can be used to control the rate at which the liposome becomes fusogenic will become apparent to those of skill in the art upon reading this disclosure.

V. Preparation of Nucleic Acid-Lipid Particles

The present invention provides a method of preparing serum-stable nucleic acid-lipid particles in which the plasmid or other nucleic acid is encapsulated in a lipid bilayer and is protected from degradation. The particles made by the methods of this invention typically have a size of about 50 nm to about 150 nm, more typically about 100 nm to about 130 nm, most typically about 110 nm to about 115 nm. The particles can be formed by any method known in the art including, but not limited to: a continuous mixing method, a detergent dialysis method, or a modification of a reverse-phase method which utilizes organic solvents to provide a single phase during mixing of the components.

In a particularly preferred embodiment, the present invention provides for nucleic acid-lipid particles produced via a continuous mixing method, e.g., process that includes providing an aqueous solution comprising a nucleic acid such as an siRNA or a plasmid, in a first reservoir, and providing an organic lipid solution in a second reservoir, and mixing the aqueous solution with the organic lipid solution such that the organic lipid solution mixes with the aqueous solution so as to substantially instantaneously produce a liposome encapsulating the nucleic acid (e.g., siRNA). This process and the apparatus for carrying this process is described in detail in U.S. Patent Publication No. 20040142025.

The action of continuously introducing lipid and buffer solutions into a mixing environment, such as in a mixing chamber, causes a continuous dilution of the lipid solution with the buffer solution, thereby producing a liposome substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

In some embodiments, the particles are formed using detergent dialysis. Without intending to be bound by any particular mechanism of formation, a plasmid or other nucleic acid (e.g., siRNA) is contacted with a detergent solution of cationic lipids to form a coated nucleic acid complex. These coated nucleic acids can aggregate and precipitate. However, the presence of a detergent reduces this aggregation and allows the coated nucleic acids to react with excess lipids (typically, non-cationic lipids) to form particles in which the plasmid or other nucleic acid is encapsulated in a lipid bilayer. Thus, the present invention provides a method for the preparation of serum-stable nucleic acid-lipid particles, comprising:

(a) combining a nucleic acid with cationic lipids in a detergent solution to form a coated nucleic acid-lipid complex;
  (b) contacting non-cationic lipids with the coated nucleic acid-lipid complex to form a detergent solution comprising a nucleic acid-lipid complex and non-cationic lipids; and
  (c) dialyzing the detergent solution of step (b) to provide a solution of serum-stable nucleic acid-lipid particles, wherein the nucleic acid is encapsulated in a lipid bilayer and the particles are serum-stable and have a size of from about 50 to about 150 nm.

An initial solution of coated nucleic acid-lipid complexes is formed by combining the nucleic acid with the cationic lipids in a detergent solution.

In these embodiments, the detergent solution is preferably an aqueous solution of a neutral detergent having a critical micelle concentration of 15-300 mM, more preferably 20-50 mM. Examples of suitable detergents include, for example, N,N'-((octanoylimino)-bis-(trimethylene))-bis-(D-gluconamide) (BIGCHAP); BRIJ 35; Deoxy-BIGCHAP; dodecylpoly(ethylene glycol) ether; Tween 20; Tween 40; Tween 60; Tween 80; Tween 85; Mega 8; Mega 9; Zwittergent® 3-08; Zwittergent® 3-10; Triton X-405; hexyl-, heptyl-,octyl- and nonyl-β-D-glucopyranoside; and heptylthioglucopyranoside; with octyl β-D-glucopyranoside and Tween-20 being the most preferred. The concentration of detergent in the detergent solution is typically about 100 mM to about 2 M, preferably from about 200 mM to about 1.5 M.

The cationic lipids and nucleic acids will typically be combined to produce a charge ratio (+/−) of about 1:1 to about 20:1, preferably in a ratio of about 1:1 to about 12:1, and more preferably in a ratio of about 2:1 to about 6:1. Additionally, the overall concentration of nucleic acid in solution will typically be from about 25 µg/mL to about 1 mg/mL, preferably from about 25 µg/mL to about 200 µg/mL, and more preferably from about 50 µg/mL to about 100 µg/mL. The combination of nucleic acids and cationic lipids in detergent solution is kept, typically at room temperature, for a period of time which is sufficient for the coated complexes to form. Alternatively, the nucleic acids and cationic lipids can be combined in the detergent solution and warmed to temperatures of up to about 37° C. For nucleic acids which are particularly sensitive to temperature, the coated complexes can be formed at lower temperatures, typically down to about 4° C.

In a preferred embodiment, the nucleic acid to lipid ratios (mass/mass ratios) in a formed nucleic acid-lipid particle will range from about 0.01 to about 0.08. The ratio of the starting materials also falls within this range because the purification step typically removes the unencapsulated nucleic acid as well as the empty liposomes. In another preferred embodiment, the nucleic acid-lipid particle preparation uses about 400 µg nucleic acid per 10 mg total lipid or a nucleic acid to lipid ratio of about 0.01 to about 0.08 and, more preferably, about 0.04, which corresponds to 1.25 mg of total lipid per 50 µg of nucleic acid.

The detergent solution of the coated nucleic acid-lipid complexes is then contacted with non-cationic lipids to provide a detergent solution of nucleic acid-lipid complexes and non-cationic lipids. The non-cationic lipids which are useful in this step include, diacylphosphatidylcholine, diacylphosphatidylethanolamine, ceramide, sphingomyelin, cephalin, cardiolipin, and cerebrosides. In preferred embodiments, the non-cationic lipids are diacylphosphatidylcholine, diacylphosphatidylethanolamine, ceramide or sphingomyelin. The acyl groups in these lipids are preferably acyl groups derived from fatty acids having $C_{10}$-$C_{24}$ carbon chains. More preferably the acyl groups are lauroyl, myristoyl, palmitoyl, stearoyl or oleoyl. In particularly preferred embodiments, the non-cationic lipid will be 1,2-sn-dioleoylphosphatidylethanolamine (DOPE), palmitoyl oleoyl phosphatidylcholine (POPC), egg phosphatidylcholine (EPC), distearoylphosphatidylcholine (DSPC), cholesterol, or a mixture thereof. In the most preferred embodiments, the nucleic acid-lipid particles will be fusogenic particles with enhanced properties in vivo and the non-cationic lipid will be DSPC or DOPE. In addition, the nucleic acid-lipid particles of the present invention may further comprise cholesterol. In other preferred embodiments, the non-cationic lipids will further comprise polyethylene glycol-based polymers such as PEG 2000, PEG 5000 and polyethylene glycol conjugated to a diacylglycerol, a ceramide or a phospholipid, as described in U.S. Pat. No. 5,820,873 and U.S. Patent Publication No. 20030077829. In further preferred embodiments, the non-cationic lipids will further comprise polyethylene glycol-based polymers such as PEG 2000, PEG 5000 and polyethylene glycol conjugated to a dialkyloxypropyl.

The amount of non-cationic lipid which is used in the present methods is typically about 2 to about 20 mg of total lipids to 50 µg of nucleic acid. Preferably the amount of total lipid is from about 5 to about 10 mg per 50 µg of nucleic acid.

Following formation of the detergent solution of nucleic acid-lipid complexes and non-cationic lipids, the detergent is removed, preferably by dialysis. The removal of the detergent results in the formation of a lipid-bilayer which surrounds the nucleic acid providing serum-stable nucleic acid-lipid particles which have a size of from about 50 nm to about 150 nm, more typically about 100 nm to about 130 nm, most typically about 110 nm to about 115 nm. The particles thus formed do not aggregate and are optionally sized to achieve a uniform particle size.

The serum-stable nucleic acid-lipid particles can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles is described in U.S. Pat. No. 4,737,323. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In another group of embodiments, the present invention provides a method for the preparation of serum-stable nucleic acid-lipid particles, comprising:
  (a) preparing a mixture comprising cationic lipids and non-cationic lipids in an organic solvent;
  (b) contacting an aqueous solution of nucleic acid with said mixture in step (a) to provide a clear single phase; and
  (c) removing said organic solvent to provide a suspension of nucleic acid-lipid particles, wherein said nucleic acid is encapsulated in a lipid bilayer, and said particles are stable in serum and have a size of from about 50 to about 150 nm.

The nucleic acids (or plasmids), cationic lipids and non-cationic lipids which are useful in this group of embodiments are as described for the detergent dialysis methods above.

The selection of an organic solvent will typically involve consideration of solvent polarity and the ease with which the solvent can be removed at the later stages of particle formation. The organic solvent, which is also used as a solubilizing agent, is in an amount sufficient to provide a clear single phase mixture of nucleic acid and lipids. Suitable solvents include, but are not limited to, chloroform, dichloromethane, diethylether, cyclohexane, cyclopentane, benzene, toluene, methanol, or other aliphatic alcohols such as propanol, isopropanol, butanol, tert-butanol, iso-butanol, pentanol and hexanol. Combinations of two or more solvents may also be used in the present invention.

Contacting the nucleic acid with the organic solution of cationic and non-cationic lipids is accomplished by mixing together a first solution of nucleic acid, which is typically an aqueous solution, and a second organic solution of the lipids. One of skill in the art will understand that this mixing can take place by any number of methods, for example by mechanical means such as by using vortex mixers.

After the nucleic acid has been contacted with the organic solution of lipids, the organic solvent is removed, thus forming an aqueous suspension of serum-stable nucleic acid-lipid particles. The methods used to remove the organic solvent will typically involve evaporation at reduced pressures or blowing a stream of inert gas (e.g., nitrogen or argon) across the mixture.

The serum-stable nucleic acid-lipid particles thus formed will typically be sized from about 50 nm to about 150 nm, more typically about 100 nm to about 130 nm, most typically about 110 nm to about 115 nm. To achieve further size reduction or homogeneity of size in the particles, sizing can be conducted as described above.

In other embodiments, the methods will further comprise adding nonlipid polycations which are useful to effect the delivery to cells using the present compositions. Examples of suitable nonlipid polycations include, but are limited to, hexadimethrine bromide (sold under the brandname POLYBRENE®, from Aldrich Chemical Co., Milwaukee, Wis., USA) or other salts of heaxadimethrine. Other suitable polycations include, for example, salts of poly-L-ornithine, poly-L-arginine, poly-L-lysine, poly-D-lysine, polyallylamine and polyethyleneimine.

In certain embodiments, the formation of the nucleic acid-lipid particles can be carried out either in a mono-phase system (e.g., a Bligh and Dyer monophase or similar mixture of aqueous and organic solvents) or in a two-phase system with suitable mixing.

When formation of the complexes is carried out in a monophase system, the cationic lipids and nucleic acids are each dissolved in a volume of the mono-phase mixture. Combination of the two solutions provides a single mixture in which the complexes form. Alternatively, the complexes can form in two-phase mixtures in which the cationic lipids bind to the nucleic acid (which is present in the aqueous phase), and "pull" it into the organic phase.

In another embodiment, the present invention provides a method for the preparation of nucleic acid-lipid particles, comprising:
 (a) contacting nucleic acids with a solution comprising non-cationic lipids and a detergent to form a nucleic acid-lipid mixture;
 (b) contacting cationic lipids with the nucleic acid-lipid mixture to neutralize a portion of the negative charge of the nucleic acids and form a charge-neutralized mixture of nucleic acids and lipids; and
 (c) removing the detergent from the charge-neutralized mixture to provide the nucleic acid-lipid particles in which the nucleic acids are protected from degradation.

In one group of embodiments, the solution of non-cationic lipids and detergent is an aqueous solution. Contacting the nucleic acids with the solution of non-cationic lipids and detergent is typically accomplished by mixing together a first solution of nucleic acids and a second solution of the lipids and detergent. One of skill in the art will understand that this mixing can take place by any number of methods, for example, by mechanical means such as by using vortex mixers. Preferably, the nucleic acid solution is also a detergent solution. The amount of non-cationic lipid which is used in the present method is typically determined based on the amount of cationic lipid used, and is typically of from about 0.2 to 5 times the amount of cationic lipid, preferably from about 0.5 to about 2 times the amount of cationic lipid used.

In some embodiments, the nucleic acids are precondensed as described in, e.g., U.S. patent application Ser. No. 09/744,103.

The nucleic acid-lipid mixture thus formed is contacted with cationic lipids to neutralize a portion of the negative charge which is associated with the nucleic acids (or other polyanionic materials) present. The amount of cationic lipids used will typically be sufficient to neutralize at least 50% of the negative charge of the nucleic acid. Preferably, the negative charge will be at least 70% neutralized, more preferably at least 90% neutralized. Cationic lipids which are useful in the present invention, include, for example, DODAC, DOTMA, DDAB, DOTAP, DC-Chol and DMRIE. These lipids and related analogs have been described in U.S. Pat. Nos. 5,208,036, 5,264,618, 5,279,833, 5,283,185, 5,753,613 and 5,785,992.

Contacting the cationic lipids with the nucleic acid-lipid mixture can be accomplished by any of a number of techniques, preferably by mixing together a solution of the cationic lipid and a solution containing the nucleic acid-lipid mixture. Upon mixing the two solutions (or contacting in any other manner), a portion of the negative charge associated with the nucleic acid is neutralized. Nevertheless, the nucleic acid remains in an uncondensed state and acquires hydrophilic characteristics.

After the cationic lipids have been contacted with the nucleic acid-lipid mixture, the detergent (or combination of detergent and organic solvent) is removed, thus forming the nucleic acid-lipid particles. The methods used to remove the detergent will typically involve dialysis. When organic solvents are present, removal is typically accomplished by evaporation at reduced pressures or by blowing a stream of inert gas (e.g., nitrogen or argon) across the mixture.

The particles thus formed will typically be sized from about 50 nm to several microns, more typically about 50 nm to about 150 nm, even more typically about 100 nm to about 130 nm, most typically about 110 nm to about 115 nm. To achieve further size reduction or homogeneity of size in the particles, the nucleic acid-lipid particles can be sonicated, filtered or subjected to other sizing techniques which are used in liposomal formulations and are known to those of skill in the art.

In other embodiments, the methods will further comprise adding nonlipid polycations which are useful to effect the lipofection of cells using the present compositions. Examples of suitable nonlipid polycations include, hexadimethrine bromide (sold under the brandname POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine and polyethyleneimine. Addition of these salts is preferably after the particles have been formed.

In another aspect, the present invention provides methods for the preparation of nucleic acid-lipid particles, comprising:
 (a) contacting an amount of cationic lipids with nucleic acids in a solution; the solution comprising from about 15-35% water and about 65-85% organic solvent and the amount of cationic lipids being sufficient to produce a +/− charge ratio of from about 0.85 to about 2.0, to provide a hydrophobic nucleic acid-lipid complex;

(b) contacting the hydrophobic, nucleic acid-lipid complex in solution with non-cationic lipids, to provide a nucleic acid-lipid mixture; and (c) removing the organic solvents from the nucleic acid-lipid mixture to provide nucleic acid-lipid particles in which the nucleic acids are protected from degradation.

The nucleic acids, non-cationic lipids, cationic lipids and organic solvents which are useful in this aspect of the invention are the same as those described for the methods above which used detergents. In one group of embodiments, the solution of step (a) is a mono-phase. In another group of embodiments, the solution of step (a) is two-phase.

In preferred embodiments, the cationic lipids are DODAC, DDAB, DOTMA, DOSPA, DMRIE, DOGS or combinations thereof. In other preferred embodiments, the non-cationic lipids are ESM, DOPE, DOPC, DSPC, polyethylene glycol-based polymers (e.g., PEG 2000, PEG 5000, PEG-modified diacylglycerols, or PEG-modified dialkyloxypropyls), distearoylphosphatidylcholine (DSPC), cholesterol, or combinations thereof. In still other preferred embodiments, the organic solvents are methanol, chloroform, methylene chloride, ethanol, diethyl ether or combinations thereof.

In one embodiment, the nucleic acid is a plasmid from which an interfering RNA is transcribed; the cationic lipid is DODAC, DDAB, DOTMA, DOSPA, DMRIE, DOGS or combinations thereof; the non-cationic lipid is ESM, DOPE, DAG-PEGs, distearoylphosphatidylcholine (DSPC), cholesterol, or combinations thereof (e.g. DSPC and DAG-PEGs); and the organic solvent is methanol, chloroform, methylene chloride, ethanol, diethyl ether or combinations thereof.

As above, contacting the nucleic acids with the cationic lipids is typically accomplished by mixing together a first solution of nucleic acids and a second solution of the lipids, preferably by mechanical means such as by using vortex mixers. The resulting mixture contains complexes as described above. These complexes are then converted to particles by the addition of non-cationic lipids and the removal of the organic solvent. The addition of the non-cationic lipids is typically accomplished by simply adding a solution of the non-cationic lipids to the mixture containing the complexes. A reverse addition can also be used. Subsequent removal of organic solvents can be accomplished by methods known to those of skill in the art and also described above.

The amount of non-cationic lipids which is used in this aspect of the invention is typically an amount of from about 0.2 to about 15 times the amount (on a mole basis) of cationic lipids which was used to provide the charge-neutralized nucleic acid-lipid complex. Preferably, the amount is from about 0.5 to about 9 times the amount of cationic lipids used.

In yet another aspect, the present invention provides nucleic acid-lipid particles which are prepared by the methods described above. In these embodiments, the nucleic acid-lipid particles are either net charge neutral or carry an overall charge which provides the particles with greater gene lipofection activity. Preferably, the nucleic acid component of the particles is a nucleic acid which interferes with the production of an undesired protein. In a preferred embodiment, the nucleic acid comprises an interfering RNA, the non-cationic lipid is egg sphingomyelin and the cationic lipid is DODAC. In a preferred embodiment, the nucleic acid comprises an interfering RNA, the non-cationic lipid is a mixture of DSPC and cholesterol, and the cationic lipid is DOTMA. In other preferred embodiments, the non-cationic lipid may further comprise cholesterol.

A variety of general methods for making SNALP-CPLs (CPL-containing SNALPs) are discussed herein. Two general techniques include "post-insertion" technique, that is, insertion of a CPL into for example, a pre-formed SNALP, and the "standard" technique, wherein the CPL is included in the lipid mixture during for example, the SNALP formation steps. The post-insertion technique results in SNALPs having CPLs mainly in the external face of the SNALP bilayer membrane, whereas standard techniques provide SNALPs having CPLs on both internal and external faces. The method is especially useful for vesicles made from phospholipids (which can contain cholesterol) and also for vesicles containing PEG-lipids (such as PEG-DAGs). Methods of making SNALP-CPL, are taught, for example, in U.S. Pat. Nos. 5,705,385, 6,586,410, 5,981,501 6,534,484; 6,852,334; U.S. Patent Publication No. 20020072121, as well as in WO 00/62813.

VI. Kits

The present invention also provides nucleic acid-lipid particles in kit form. The kit may comprise a container which is compartmentalized for holding the various elements of the nucleic acid-lipid particles (e.g., the nucleic acids and the individual lipid components of the particles). In some embodiments, the kit contains the nucleic acid-lipid particles compositions of the present inventions, preferably in dehydrated form, with instructions for their rehydration and administration.

VII. Administration of Nucleic Acid-Lipid Particles

The serum-stable nucleic acid-lipid particles of the present invention are useful for the introduction of nucleic acids into cells. Accordingly, the present invention also provides methods for introducing a nucleic acids (e.g., an interfering RNA) into a cell. Depending on the desired effect, the immunostimulatory effects of the siRNA can be enhanced or diminished by introducing (i.e., enhance) or eliminating (i.e., diminish) the 5'-GU'3' dinucleotide motif. The methods are carried out in vitro or in vivo by first forming the particles as described above, then contacting the particles with the cells for a period of time sufficient for delivery of interfering RNA to occur.

The nucleic acid-lipid particles of the present invention can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid.

A. In vitro Delivery

For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

Contact between the cells and the nucleic acid-lipid particles, when carried out in vitro, takes place in a biologically compatible medium. The concentration of particles varies widely depending on the particular application, but is generally between about 1 μmol and about 10 mmol. Treatment of the cells with the nucleic acid-lipid particles is generally carried out at physiological temperatures (about 37° C.) for periods of time of from about 1 to 48 hours, preferably of from about 2 to 4 hours.

In one group of preferred embodiments, a nucleic acid-lipid particle suspension is added to 60-80% confluent plated cells having a cell density of from about $10^3$ to about $10^5$ cells/mL, more preferably about $2\times10^4$ cells/mL. The concentration of the suspension added to the cells is preferably of from about 0.01 to 0.2 µg/mL, more preferably about 0.1 µg/mL.

The nucleic acid-lipid particles of the present invention can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid.

Using an Endosomal Release Parameter (ERP) assay, the delivery efficiency of the SNALP or other lipid-based carrier system can be optimized. An ERP assay is described in detail in U.S. Patent Publication No. 20030077829. More particularly, the purpose of an ERP assay is to distinguish the effect of various cationic lipids and helper lipid components of SNALPs based on their relative effect on binding/uptake or fusion with/destabilization of the endosomal membrane. This assay allows one to determine quantitatively how each component of the SNALP or other lipid-based carrier system effects delivery efficiency, thereby optimizing the SNALPs or other lipid-based carrier systems. Usually, an ERP assay measures expression of a reporter protein (e.g., luciferase, β-galactosidase, green fluorescent protein, etc.), and in some instances, a SNALP formulation optimized for an expression plasmid will also be appropriate for encapsulating an interfering RNA. In other instances, an ERP assay can be adapted to measure downregulation of transcription or translation of a target sequence in the presence or absence of an interfering RNA. By comparing the ERPs for each of the various SNALPs or other lipid-based formulations, one can readily determine the optimized system, e.g., the SNALP or other lipid-based formulation that has the greatest uptake in the cell.

Suitable labels for carrying out the ERP assay of the present invention include, but are not limited to, spectral labels, such as fluorescent dyes (e.g., fluorescein and derivatives, such as fluorescein isothiocyanate (FITC) and Oregon Green™; rhodamine and derivatives, such Texas red, tetrarhodimine isothiocynate (TRITC), etc., digoxigenin, biotin, phycoerythrin, AMCA, CyDyes™, and the like; radiolabels, such as $^3$H, $^{125}$I, 35S, $^{14}$C, $^{32}$P, $^{33}$P, etc.; enzymes, such as horse radish peroxidase, alkaline phosphatase, etc.; spectral colorimetric labels, such as colloidal gold or colored glass or plastic beads, such as polystyrene, polypropylene, latex, etc. The label can be coupled directly or indirectly to a component of the SNALP or other lipid-based carrier system using methods well known in the art. As indicated above, a wide variety of labels can be used, with the choice of label depending on sensitivity required, ease of conjugation with the SNALP component, stability requirements, and available instrumentation and disposal provisions.

B. In vivo Delivery

The nucleic acid-lipid particles of the present invention can be administered via any route known in the art including, e.g., intravenously, intramuscularly, subcutaneously, intradermally, intraperitoneally, orally, intranasally, or topically either alone or in mixture with a physiologically-acceptable carrier (such as physiological saline or phosphate buffer) selected in accordance with the route of administration and standard pharmaceutical practice.

When preparing pharmaceutical preparations of the nucleic acid-lipid particles of the invention, it is preferable to use quantities of the nucleic acid-lipid particles which have been purified to reduce or eliminate empty lipid particles or particles with nucleic acid portion associated with the external surface. The pharmaceutical carrier is generally added following particle formation. Thus, after the particle is formed, the particle can be diluted into pharmaceutically acceptable carriers.

The concentration of particles in the pharmaceutical formulations can vary widely, i.e., from less than about 0.05%, usually at or at least about 2.5% to as much as 10 to 30% by weight and will be selected primarily by fluid volumes, viscosities, etc., in accordance with the particular mode of administration selected.

1. Injectable Delivery

In certain circumstances it will be desirable to deliver the pharmaceutical compositions disclosed herein parenterally, intravenously, intramuscularly, subcutaneously, intradermally, or intraperitoneally as described in U.S. Pat. Nos. 5,543,158; 5,641,515 and 5,399,363. Solutions of the nucleic acid-lipid particles may be prepared in water suitably mixed with a surfactant. Dispersions may also be prepared in glycerol, liquid polyethylene glycols, and mixtures thereof and in oils. Typically, these preparations contain a preservative to prevent the growth of microorganisms. Generally, when administered intravenously, the nucleic acid-lipid particles formulations are formulated with a suitable pharmaceutical carrier. Generally, normal buffered saline (135-150 mM NaCl) will be employed as the pharmaceutically acceptable carrier, but other suitable carriers will suffice. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

2. Oral Delivery

In certain applications, the nucleic acid-lipid particles disclosed herein may be delivered via oral administration to the individual. The active compounds may even be incorporated with excipients and used in the form of ingestible tablets, buccal tablets, troches, capsules, elixirs, mouthwash, suspensions, oral sprays, syrups, wafers, and the like (see, U.S. Pat. Nos. 5,641,515; 5,580,579 and 5,792,451). The tablets, troches, pills, capsules and the like may also contain the following: binders, gelatin; excipients, lubricants, or flavoring agents. When the dosage unit form is a capsule, it may contain, in addition to materials of the above type, a liquid carrier. Various other materials may be present as coatings or to otherwise modify the physical form of the dosage unit. Of course, any material used in preparing any dosage unit form should be pharmaceutically pure and substantially non-toxic in the amounts employed.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

3. Nasal Delivery

In certain embodiments, the pharmaceutical compositions may be delivered by intranasal sprays, inhalation, and/or other aerosol delivery vehicles. Methods for delivering nucleic acid compositions directly to the lungs via nasal aerosol sprays has been described e.g., in U. S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Likewise, transmucosal drug delivery in the form of a polytetrafluoroetheylene support matrix is described in U.S. Pat. No. No. 5,780,045.

4. Topical Delivery

In another example of their use, nucleic acid-lipid particles can be incorporated into a broad range of topical dosage forms including, but not limited to, gels, oils, emulsions and the like. For instance, the suspension containing the nucleic acid-lipid particles can be formulated and administered as topical creams, pastes, ointments, gels, lotions and the like.

EXAMPLES

The following examples are provided to illustrate, but not to limit the claimed invention.

Example 1

Materials and Methods

Background: Specific gene silencing via RNA interference (RNAi) has become a widely used tool in biological research and is rapidly being developed for clinical application. RNAi utilises short double-stranded RNA (siRNA), 18-22 bp in length, that are widely regarded as being non-inflammatory and unable to activate the interferon response in mammalian cells due to their small size. However, few studies in immunological systems have been reported to support these contentions. To address this directly, we have investigated the immunostimulatory properties of a panel of siRNA. More particularly, chemically synthesised siRNA, either liposome encapsulated, lipid complexed (Oligofectamine) or naked, were tested for their ability to stimulate a cytokine response from human blood cell subsets. Activation of the innate immune system by siRNA in vivo was also assessed in murine studies.

siRNA: All siRNA used in these studies were chemically synthesized by Dharmacon (Lafayette, Colo.) and received as desalted, pre-annealed duplexes in either standard or PAGE-purified formats. siRNA homologous to mRNA encoding β-galactosidase, firefly luciferase, BP120 and the bacterial Tetracycline Resistance gene (TetR) were generated together with corresponding non-targeting sequence control siRNAs. These nucleotide sequences are detailed in FIG. 16. β-gal control and BP1 control sequences were modified by selective base substitutions as described and detailed in FIG. 12A.

Mice: 6-8 week old CD I ICR mice were obtained from Harlan (Indianapolis Ind.) and subject to a three week quarantine and acclimation period prior to use. siRNA and lipid formulations were administered as a single intravenous injection in the lateral tail vein in 0.2 ml PBS. Injections were administered over a period of 3-5 seconds. Blood was collected by cardiac puncture and processed as plasma for cytokine analysis. Blood cell counts were performed at The Central Laboratory For Veterinarians (Langley, BC).

Lipid Encapsulation of siRNA: siRNAs were encapsulated into liposomes by an adaptation of the method developed by Wheeler et al., *Gene Ther.* 6, 271-281 (1999), whereby detergents are replaced by ethanol for the solublization and dialysis of the lipid components. Liposomes were composed of the following lipids; synthetic cholesterol (Sigma, St. Louis, Mo.), the phospholipid DSPC (1,2-distearoyl-sn-glycero-3-phosphocholine; Avanti Polar Lipids, Alabaster, Ala.), the PEG-lipid PEG-cDMA (3-N-[(-Methoxy poly(ethylene glycol)2000)carbamoyl]-1,2-dimyrestyloxy-propylamine), and the cationic lipid DODMA (1,2-Di-o-octadecenyl-3-(N,N-dimethyl)aminopropane) or DLinDMA (1,2-Dilinoleyloxy-3-(N,N-dimethyl)aminopropane) in the molar ratios 55:20:10:15, or 48:20:2:30 respectively. The lipids PEG-cDMA, DODMA, and DLinDMA were synthesized in house at Protiva Biotherapeutics. The resulting stabilized lipid particles were dialyzed in PBS prior to use. For vehicle controls, empty liposomes with identical lipid composition were formed in the absence of siRNA.

Formation of siRNA Complexes: In some experiments, siRNA were complexed with either oligofectamine or Lipofectamine (Invitrogen; Carlsbad, Calif.) according to the manufacturers instructions. siRNA were complexed with either 10 KDa PEI (Polysciences Inc. Warrington, Pa.) or poly-L-lysine (Sigma; Poole, UK) diluted in distilled water by dropwise addition of the nucleic acid to the polycation solution while vortexing. PEI Polyplexes were formed at an approximate N:P ratio of 10.5:1 and PLL polyplexes at a charge ratio of 3:1 (+:−). The resulting polyplexes were approximately 140 nm and >500 nm in diameter respectively.

Cell Isolation and Culture: Human PBMC were isolated from whole blood from healthy donors by a standard Ficoll-Hypaque density centrifugation technique. Isolation of $CD14^+$ monocytes and $BDCA4^+$ pDC from human PBMC was performed by positive selection with MACS magnetic beads using MiniMacs columns (Miltenyi; Auburn, Calif.) according to the manufacturers instructions. Yields of pDC enriched cells were typically 0.3 to 0.5% of the total PBMC population. For stimulation assays, $2 \times 10^5$ freshly isolated cells were seeded in triplicate in 96 well plates and cultured in RPMI 1640 medium with 10% FCS, 2 mM glutamine, 100 U/mL penicillin and 100 ug/mL streptomycin. siRNA were either liposome encapsulated or complexed with Oligofectamine (Invitrogen, Carlsbad, Calif.) then added to cells at the indicated final nucleic acid concentration. Empty liposomes or Oligofectamine alone were used as lipid vehicle controls. In some experiments, cultures were supplemented with 20% autologous human plasma or various concentrations of chloroquine (Sigma, St. Louis, Mo.) at the start of culture. Supernatants were collected after 16-20 h of culture and assayed for IFN-α, IL-6 and TNF-α by sandwich ELISA.

Cytokine ELISA: All cytokines were quantified using sandwich ELISA kits. These were mouse and human interferon-α (PBL Biomedical, Piscataway, N.J.), Human IL-6 and TNF-α (eBioscience, San Diego, Calif.) and mouse IL-6, TNF-α and IFN-α (BD Biosciences, San Diego, Calif.).

In Vitro RNA Interference Assay: Murine Neuro2a-LacZ cell lines that stably express μ-gal were generated by lipid transfection of neuro2a cells with a pcDNA5/LacZ construct (Invitrogen, Carlsbad Calif.). Stable transfectants were selected and maintained using Hygromycin. LacZ-Neuro2a cells were seeded into 24 well plates and after overnight culture, treated with lipid encapsulated siRNA targeting β-gal or the non-targeting sequence control duplex. Cells were then cultured for a further 48 h before being washed and lysed with 250 mM sodium phosphate containing 0.1% Triton-X100. β-galactosidase enzyme activity was quantitated in cell lysates using the CPRG assay (Gene Therapy Systems, San Diego, Calif.) according to the manufacturer's instructions. Results from the CPRG assay were confirmed in parallel experiments by Xgal staining of fixed cell monolayers and microscopic analysis.

Example 2

SNALP Encapsulating siRNA Exhibit Extended Blood Circulation Times that are Regulated by the PEG-lipid Male A/J mice bearing subcutaneous Neuro2a tumors on the hind flank were treated with a single intravenous injection of SNALP (100 μg siRNA) labeled with the non-exchangeable lipid marker $^3$H-cholesteryl hexadecyl ether and containing either PEG-c-DSA or PEG-c-DMA (C18 or C14 alkyl chain length respectively). Whole blood samples were monitored for the $^3$H-cholestryl hexadecyl ether for 24 hours following intravenous injection of the SNALP. Error bars represent standard errors of the mean (n=5). 50% of injected dose remains in the blood after 16 h and 3 h for SNALP containing PEG-c-DSA or PEG-c-DMA respectively. The results are shown in FIG. 1.

This example demonstrates that blood circulation times are influenced by the lipid alkyl chain length of the PEG-lipid, i.e., PEG-C-DMA formulations preferentially accumulate within the liver, whereas PEG-C-DSA formulations accumulate at distal tumor sites. This property could be used to target lipid encapsulated siRNA to different sites.

Example 3

Figure 2:
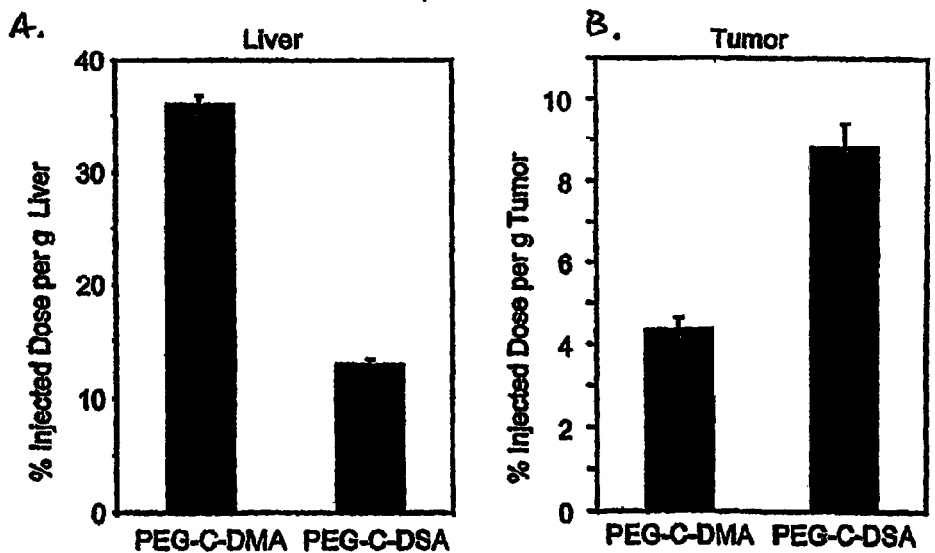
FIG. 2 illustrates data demonstrating that SNALP encapsulating siRNA can be programmed to target specific disease sites.

SNALP can be Programmed to Target Specific Disease Sites Including the Liver and Distal Tumour Biodistribution of radio-labeled SNALP was assessed after 24 h in the tumour bearing mice described in Example 2. PEG-c-DMA SNALP show preferential accumulation in the liver (35%) compared to PEG-c-DSA SNALP (13%). In contrast, PEG-c-DSA SNALP demonstrate enhanced targeting to the tumour site. The results are shown in FIG. 2.

Example 4 siRNA Duplexes Stimulate Production of Type I Interferons and Inflammatory Cytokines in Human Cells To determine if human immune cells are activated by synthetic siRNA, we cultured human peripheral blood mononuclear cells (PBMC) in the presence of siRNA either encapsulated in liposomes or complexed with the transfection reagent Oligofectamine.

Human PBMC isolated by Ficoll centrifugation were incubated overnight with either 3 μg/ml β-Gal siRNA (Dharmacon) encapsulated in SNALP, complexed with Oligofectamine (lipoplex) or naked siRNA. Levels of Interferon-alpha (IFNα), IL-6 and TNF-α in the culture supernatant were assayed by ELISA. Encapsulated siRNA stimulated predominant IFNα response whereas complexed siRNA primarily elicited inflammatory cytokines. Naked siRNA or the lipid components alone were non-stimulatory at this concentration. (mean+S.D. of triplicate cultures). siRNA duplexes that were immunostimulatory in the mouse also induced significant IFN-α and inflammatory cytokine release from human PBMC when intracellular delivery was facilitated by either transfection method. The results are shown in FIG. 3A.

SNALP encapsulating β-gal siRNA (2 mg/kg, ~40 mg) or equivalent doses of naked siRNA or lipids alone were intravenously administered to ICR mice. Plasma cytokines were assayed 6 h after administration. Significant induction of IFNα, IL-6 and TNFα was elicited by siRNA SNALP. (mean+SD, n=4). The results are shown in FIGS. 3B-3C.

IFNα responses to different doses of β-Gal siRNA were assessed in vivo in ICR mice or in vitro using human PBMC. (1 μg/ml siRNA=~75 nM). The results are shown in FIGS. 3D-3E.

Treatment with lipids alone or naked siRNA yielded no detectable cytokine release. Optimal stimulation of IFN-α was associated with encapsulated liposomal delivery of siRNA whereas lipid complexed siRNA induced a predominantly inflammatory cytokine response.

The stimulation of human PBMC by siRNA was also dependent on nucleotide sequence. βgal 728 siRNA duplexes were significantly more potent at inducing IFN-α (FIG. 9), IL-6 and TNF-α compared to the BPI duplex. >The relative potency of various siRNAs at inducing a cytokine response in human PBMC was similar to that seen in the mouse, suggesting that the mechanism of siRNA recognition may be broadly conserved. Initial experiments demonstrated that immune stimulation by siRNA was enhanced in whole blood cultures. This effect could be reconstituted in PBMC cultures by the addition of autologous plasma (FIG. 9). Even under these culture conditions, only high concentrations of BP1 siRNA was able to induce IFN-α release. The mechanism by which autologous plasma enhances the inflammatory response to siRNA in vitro but may reflect either the provision of growth factors for cytokine producing cells or the involvement of a soluble co-factor in the recognition of siRNA by its cognate receptor.

Example 5

Figure 4:
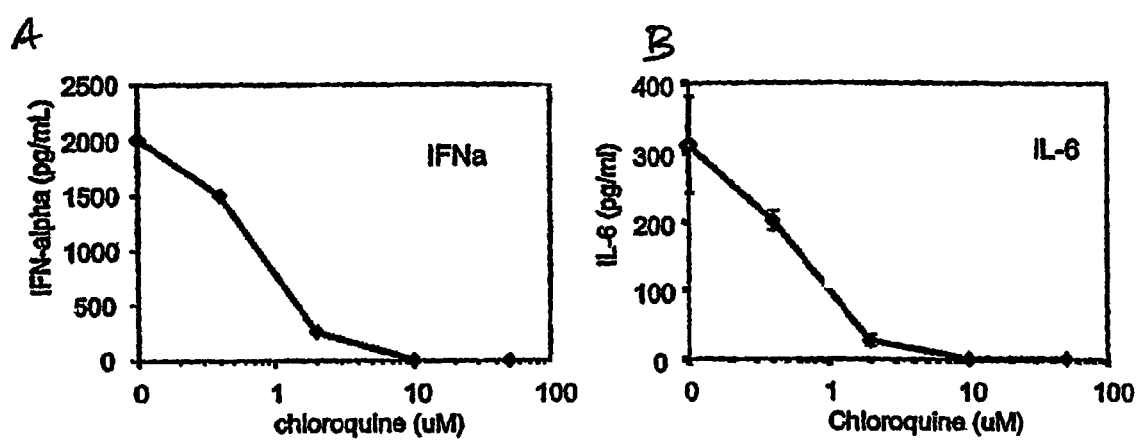
FIG. 4 illustrates data demonstrating that the immunostimulatory properties of siRNA are characteristic of a toll-like receptor mediated immune response and that dendritic cells are one cell type responsible for the IFN-α response to lipid-encapsulated siRNA.

Immunostimulatory Properties of siRNA Are Characteristic of A Toll-Like Receptor Mediated Immune Response Human PBMC were stimulated overnight with siRNA SNALP (3 μg/ml) in the presence of increasing concentrations of chloroquine. Levels of IFNα and IL-6 were assessed in culture supernatants by ELISA. siRNA induced cytokine release was inhibited by >90% at 2 µgM Chloroquine concentration. (mean+S.D. of triplicate cultures). The results are shown in FIGS. 4A-B. These results demonstrate that immune stimulation by siRNA SNALP is highly sensitive to inhibition by chloroquine, thus implying that the immune stimulation is mediated via a toll-like receptor.

Figure 4C:
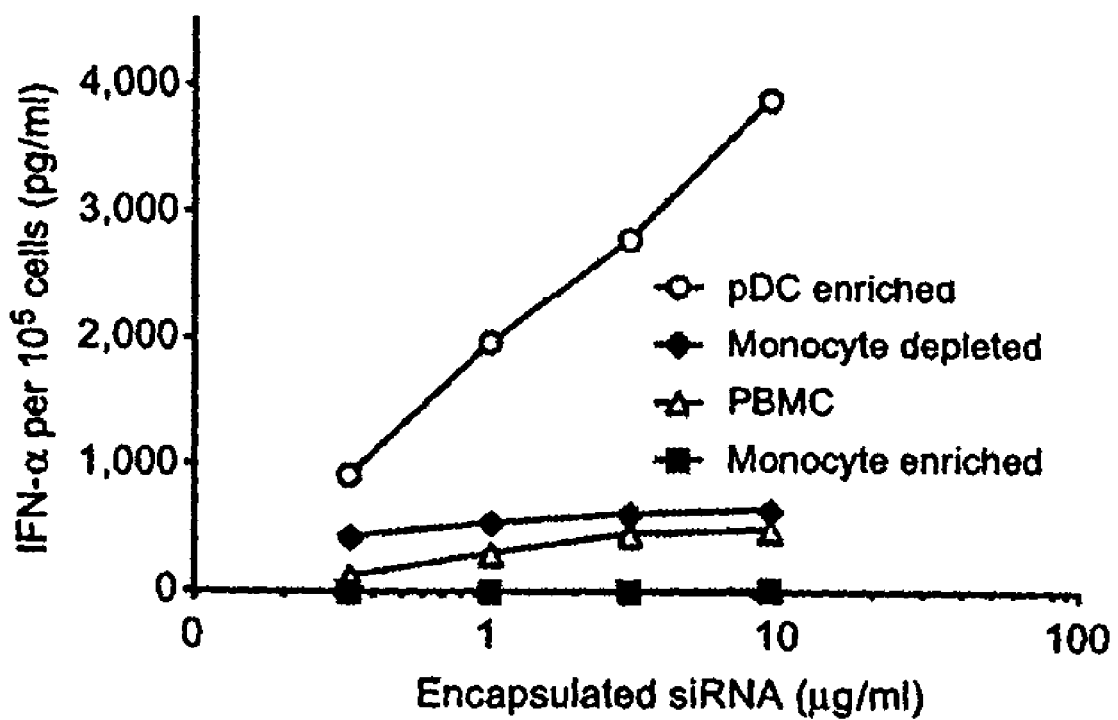
FIG. 4C illustrates data demonstrating that dendritic cells are the primary cell type responsible for the IFN-α response to lipid-encapsulated siRNA.

Human monocytes and plasmacytoid dendritic cells (pDC) were fractionated from PBMC by magnetic bead separation (Miltenyi). PBMC, monocyte depleted PBMC, monocyte enriched and pDC enriched fractions were stimulated with increasing doses of siRNA SNALP overnight. Treatment with lipids alone or naked siRNA yielded no detectable cytokine release. Induction of IFNa requires the presence of pDC. Optimal stimulation of IFN-α was associated with encapsulated liposomal delivery of siRNA whereas lipid complexed siRNA induced a predominantly inflammatory cytokine response. Cell fractionation studies using magnetic bead separation revealed BDCA4+plasmacytoid dendritic cells (pDC) to be the primary PBMC cell type responsible for the IFN-α response to lipid encapsulated siRNA. By contrast, purified $CD14^+$ monocytes produced little IFN-α when cultured with stimulatory siRNA whereas monocyte depleted PBMC retained full capacity to respond. IFNα levels represent mean of pooled triplicate cultures. Data is representative of 3 separate experiments. The results are shown in FIG. 4C. These results demonstrate that plasmacytoid dendritic cells are the principal PBMC cell type responsible for the interferon response to siRNA, further supporting the possibility that the immune stimulation is mediated via a toll-like receptor.

Example 6 siRNA-Cationic Lipid Complexes Induce an Immune Response

This example describes experiments demonstrating in vitro induction of immune responses by siRNA-cationic lipid complexes.

Mouse splenocyte cell suspensions were prepared from ICR mouse spleens and stimulated with either 1 µg/ml or 3 µg/ml siRNA complexed with Oligofectamine™. IFN-α levels were measured in the culture supernatants after overnight culture.

Figure 5:
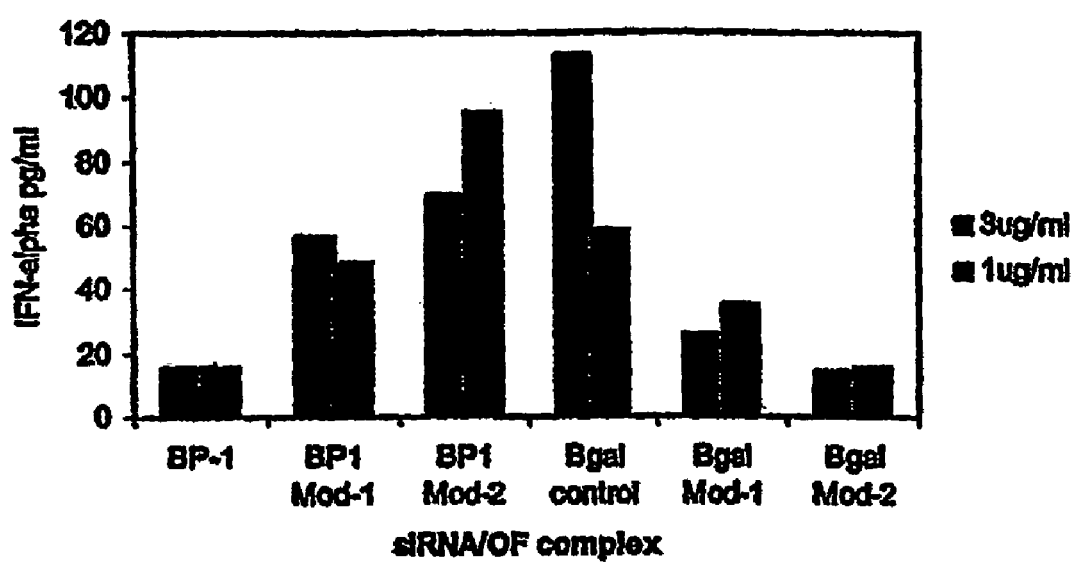
FIG. 5 illustrates data demonstrating that immune stimulation by siRNA duplexes is induced by a GU-rich motif (e.g., 5'-UGU-3' and 5'-UGUGU-3' motifs).

Specifically, the following siRNA molecules (SEQ ID NOS: 102-113) were used:

The results are shown in FIG. 5. These results provide support that GU-rich motifs (e.g., 5'-UGU-3' or 5'-UGUGU-3') are responsible for the immunostimulatory activity of an siRNA duplex.

Example 7 siRNA Encapsulated in Nucleic Acid-Lipid Particles Induces an Immune Response

This example describes experiments demonstrating in vivo induction of immune responses by siRNA encapsulated in nucleic acid-lipid particles comprising PEG-dimyristyloxypropyl conjugates.

Figure 6:
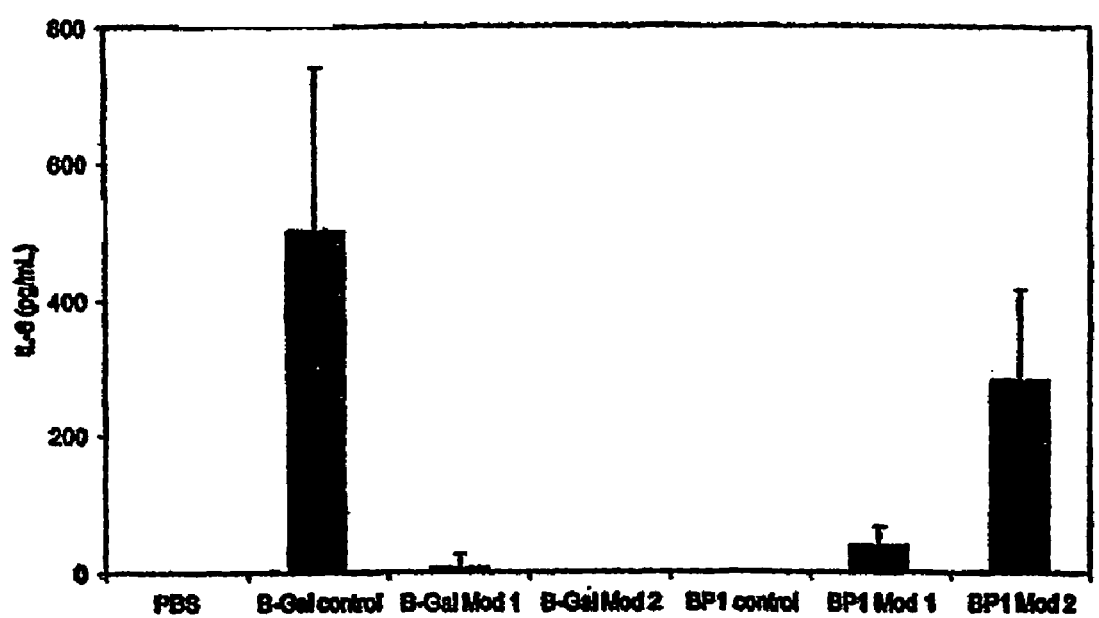
FIG. 6 illustrates data demonstrating that immune stimulation by siRNA duplexes is induced by a GU-rich motif (e.g., 5'-UGU-3' and 5'-UGUGU-3' motifs).
Figure 7:
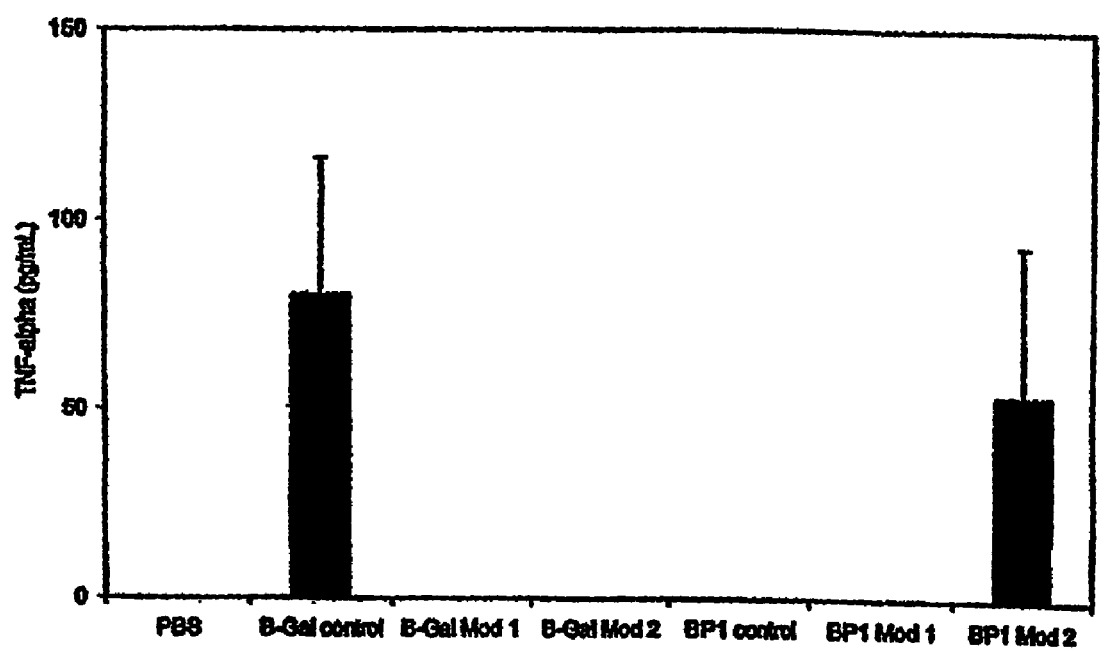
FIG. 7 illustrates data demonstrating that immune stimulation by siRNA duplexes is induced by a GU-rich motif (e.g., 5'-UGU-3' and 5'-UGUGU-3' motifs).
Figure 8:
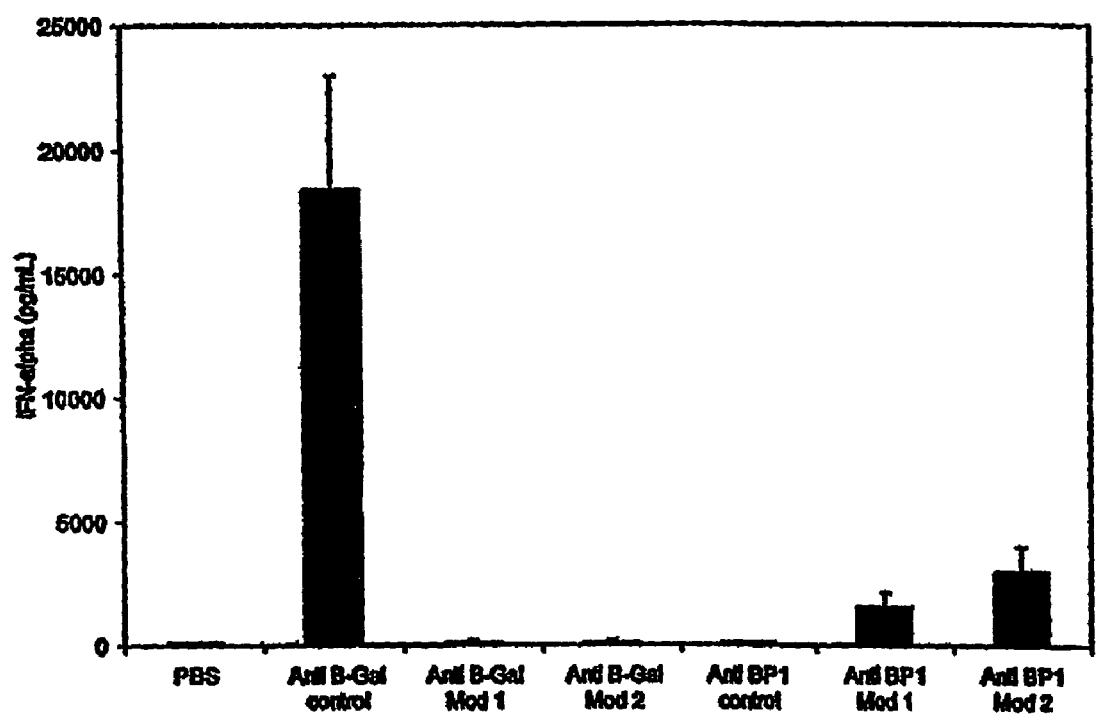
FIG. 8 illustrates data demonstrating that immune stimulation by siRNA duplexes is induced by a GU-rich motif (e.g., 5'-UGU-3' and 5'-UGUGU-3' motifs).

The siRNA molecules described in Example 7 above, were synthesized and encapsulated in nucleic acid-lipid particles using the methods described herein. The encapsulated siRNA (i.e., BP-1, BP-1 Mod-1, BP-1 Mod-2, βgal, βgal Mod-1, or βgal Mod-2) was administered to mice intravenously. Plasma IL-6, TFN-α, and IFN-α levels were measured 6 hours after administration of the siRNA. The results are shown in FIGS. 6-8.

| Group | # Mice | SNALP Formulation | treatment day | terminate | ASSAY |
|---|---|---|---|---|---|
| A | 3 | PBS | day 0 | 6 hr | Plasma for cytokine analysis |
| B | 4 | 10% PEG2000 cDMA βGal control | day 0 | 6 hr | |
| C | 4 | 10% PEG2000 cDMA βGal Mod 1 | day 0 | 6 hr | |
| D | 4 | 10% PEG2000 cDMA βGal Mod 2 | day 0 | 6 hr | |
| E | 4 | 10% PEG2000 cDMA BP1 control | day 0 | 6 hr | |
| F | 4 | 10% PEG2000 cDMA BP1 Mod 1 | day 0 | 6 hr | |
| G | 4 | 10% PEG2000 cDMA BP1 Mod 2 | day 0 | 6 hr | |

```
1.    βGal siRNA (Immunostimulatory sequence)
         5'-U U G A U G U G U U U A G U C G C U A U U-3'
         3'-U U A A C U A C A C A A A U C A G C G A U-5'

2.    βGal Mod-1 (U → C substitution)
         5'-U U G A U G C G U U U A G U C G C U A U U-3'
         3'-U U A A C U A C G C A A A U C A G C G A U-5'

3.    βGal Mod-2 (U → C; U → C substitutions)
         5'-U U G A U G C G C U U A G U C G C U A U U-3'
         3'-U U A A C U A C G C G A A U G A G C G A U-5'

4.    BP1 siRNA (less immunostimulatory)
         5'-C A G C U U U G G C U G A G C G U A U U-3'
         3'-U U G U C G A A A C C G A C U C G C A U A-5'

5.    BP1 Mod-1 (G → U substitution)
         5'-C A G C U U U G U C U G A G C G U A U U-3'
         3'-U U G U C G A A A C A G A C U C G C A U A-5'

6.    BP1 Mod-2 (G → U, C → G substitutions)
         5'-C A G C U U U G U G U G A G C G U A U U-3'
         3'-U U G U C G A A A C A C A C U C G C A U A-5'
```

A single base substitution to disrupt the 5'-UGUGU-3' motif in the B-Gal siRNA sequence significantly reduces the immunostimulatory activity of the resulting siRNA duplex (B-Gal Mod1). Conversely, stepwise introduction of a 5'-UGUGU-3' motif into the BP-1 control siRNA sequence generates duplexes with increasing immunostimulatory activity. (Data represent mean+SD, n=4). The results are shown in FIGS. 6-8. These results demonstrate that siRNA duplexes can be rendered more or less immunostimulatory by modifying 5'-UGU-3' motifs. These results also provide further support that the base sequence motif 5'-UGU-3' or 5'-UGUGU-3' is responsible for the immunostimulatory activity of an siRNA duplex.

Example 8

Plasma Derived Factors Enhance the Sequence Specific Immunostimulatory Effects of siRNA in vitro Human PBMC were cultured overnight with SNALP containing either the highly stimulatory B-Gal siRNA or the less stimulatory BP-1 control siRNA set forth in Example 6 above in the presence or absence of 10% autologous plasma. IFN-α levels are expressed as mean+/−SD of triplicate cultures. Human plasma enhances the stimulatory effects of Bgal siRNA and facilitates low level IFNα induction by BP-1 control siRNA at high doses.

The stimulation of human PBMC by siRNA was dependent on nucleotide sequence. βgal siRNA duplexes were significantly more potent at inducing IFN-α), IL-6 and TNF-α compared to the BP1 duplex. Initial experiments demonstrated that siRNA mediated immune stimulation was enhanced in whole blood cultures. This effect could be reconstituted in PBMC cultures by the addition of autologous plasma. Even under these culture conditions, BP1 siRNA was only able to induce low levels of IFN-α These results are shown in FIGS. 9A-9B.

The relative potency of the various siRNAs is similar to that seen in the mouse, suggesting that the mechanism of siRNA recognition in humans and mice may be based on broadly similar nucleotide sequence patterns.

Figure 10:
FIG. 10 is Table 1 which summarizes data from in vitro and in vivo experiments to measure the immunostimulatory effects of selected siRNA molecules (SEQ ID NO:1-69).

Example 9 siRNA-Cationic Lipid Complexes and siRNA Encapsulated in Nucleic Acid-Lipid Particles Induce Immune Responses Additional siRNA sequences were complexed with cationic lipids or encapsulated in the nuclec acid-lipid particles described herein. The complexes were contacted with murine splenocytes as in Example 6 and the encapsulated siRNA were administered to mice as in Example 7. The results from the in vitro and in vivo experiments are summarized in FIG. 10.

Example 10

Sequence Dependent Induction of Cytokines by Systemically Administered siRNA.

Figure 11A:
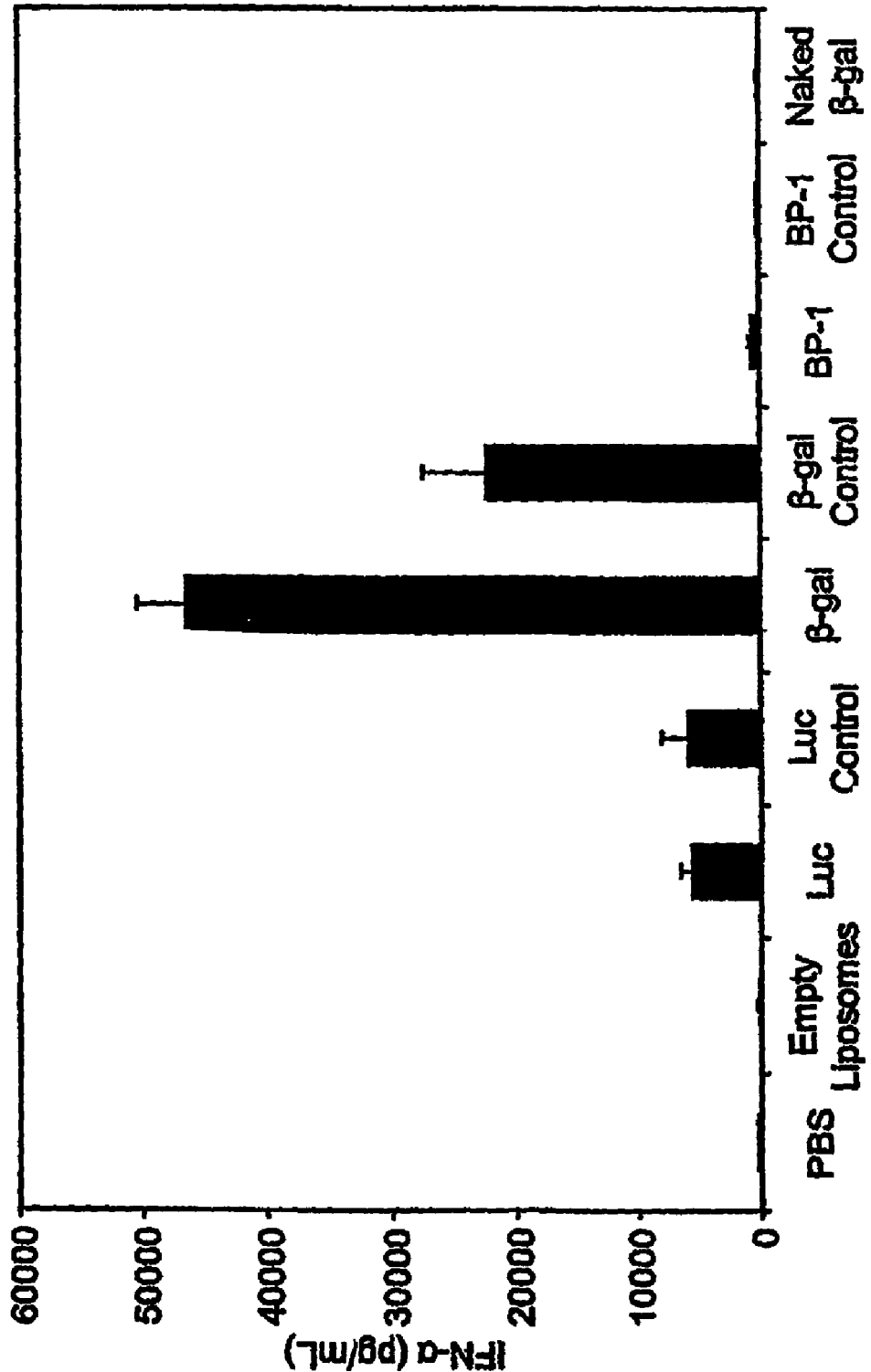
FIG. 11A illustrates serum IFN-α levels 6 h after intravenous administration of 50 μg (~2 mg/kg) encapsulated siRNA targeting luciferase (Luc), β-galactosidase (β-gal), BP1 or the respective non-targeting sequence control siRNA into ICR mice. Injection of empty liposomes or naked β-gal siRNA alone induced no detectable IFN-α.
Figure 11B:
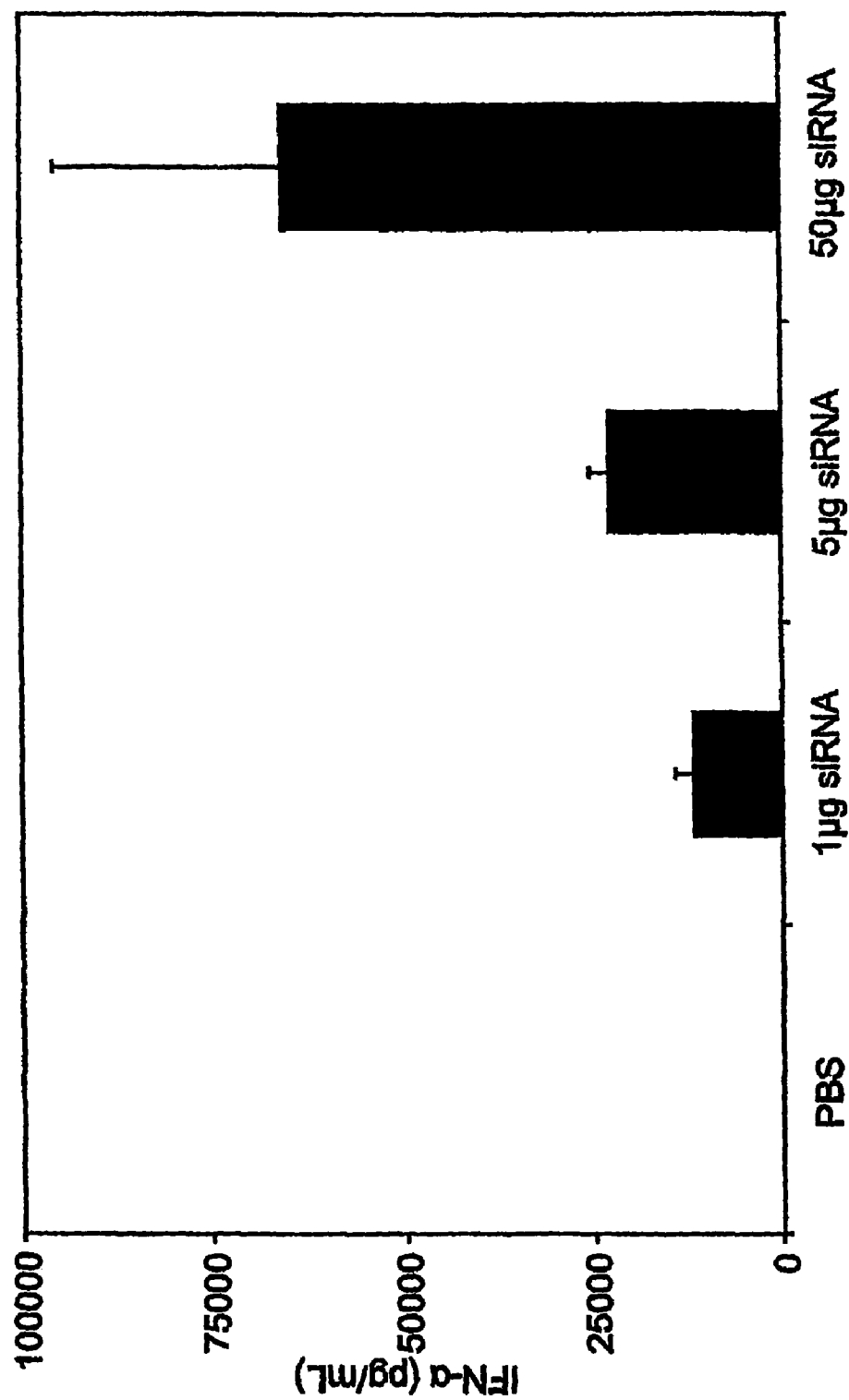
FIG. 11B illustrates a dose response to encapsulated β-gal 728 siRNA measuring serum IFN-α at 6 h.
Figure 13:
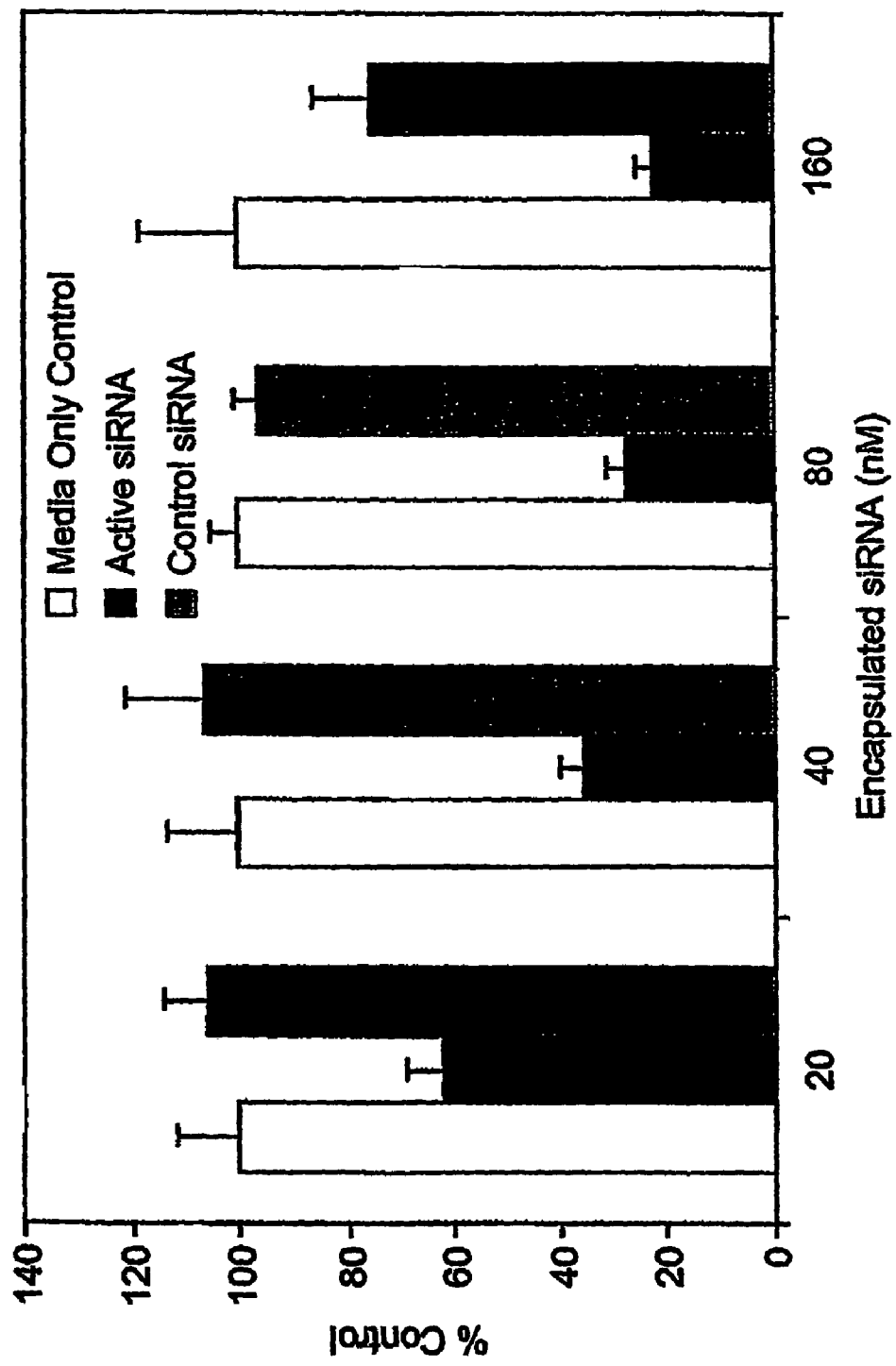
FIG. 13 illustrates data demonstrating that lipid encapsulated siRNA is effective at mediating RNAi in vitro.

To examine whether synthetic siRNA can activate an innate immune response, we tested a panel of siRNA duplexes for their ability to elicit a cytokine response in mice. To achieve effective systemic delivery of siRNA to target cells in vivo, we fully encapsulated synthetic siRNA within liposomes as described in Example 1. The resulting 100-120 nm diameter lipid particles protect the encapsulated siRNA from nuclease degradation, exhibit extended blood circulation times and are effective at mediating RNAi (FIGS. 1 and 13). Intravenous administration of lipid encapsulated siRNA targeting either β-galactosidase (β-gal 728), firefly Luciferase (Luc) or the respective non-targeting sequence control duplexes induced a significant, dose dependent IFN-α response in ICR mice (FIGS. 11A and 11B).

Figure 11C:
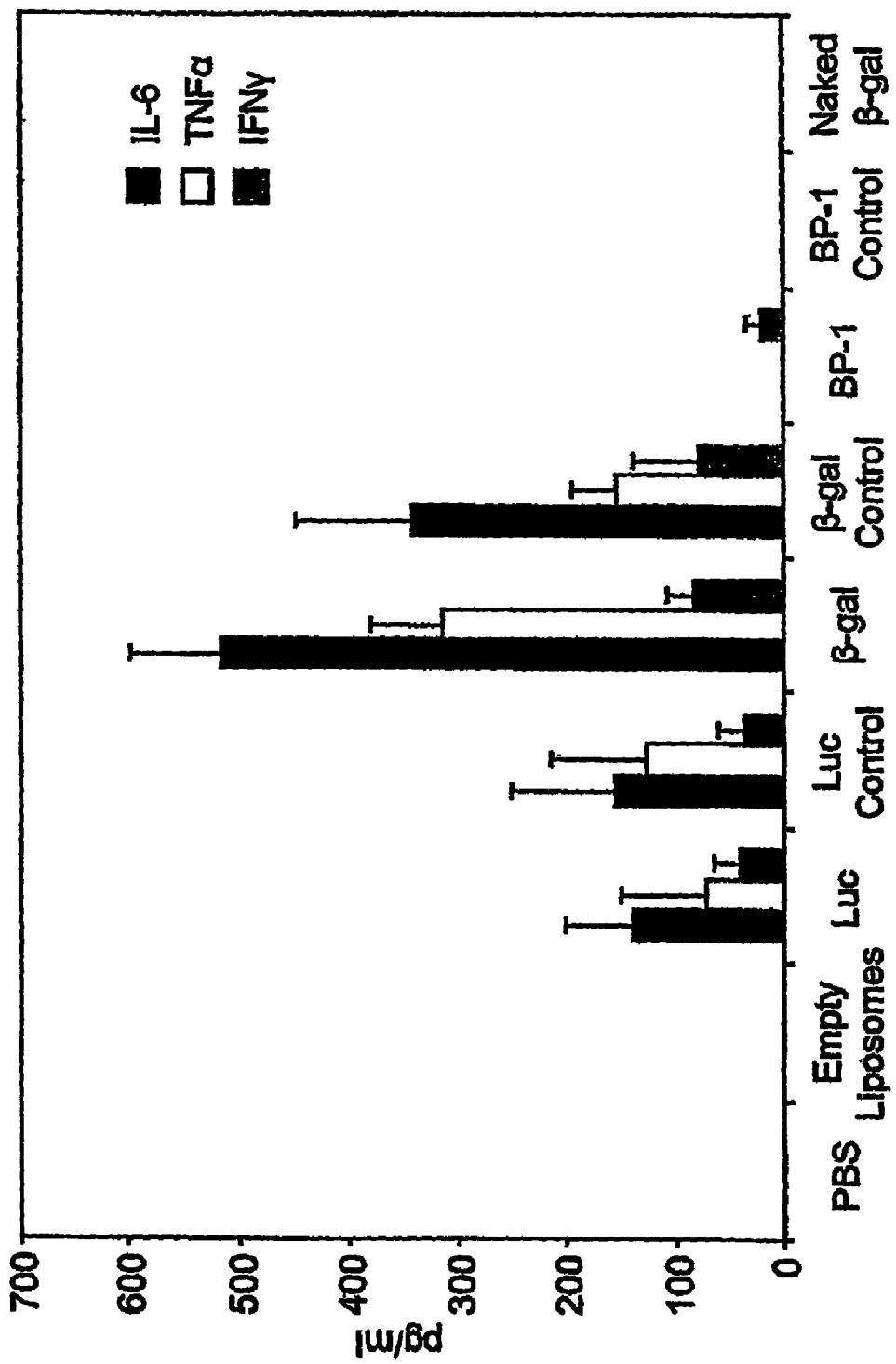
FIG. 11C illustrates data demonstrating serum IFN-α levels 6 h after intravenous administration of 50 μg β-gal 728, β-gal 481, TetR 57 or TetR control siRNA encapsulated in liposomes comprising DLinDMA in the lipid bilayer.
Figure 11D:
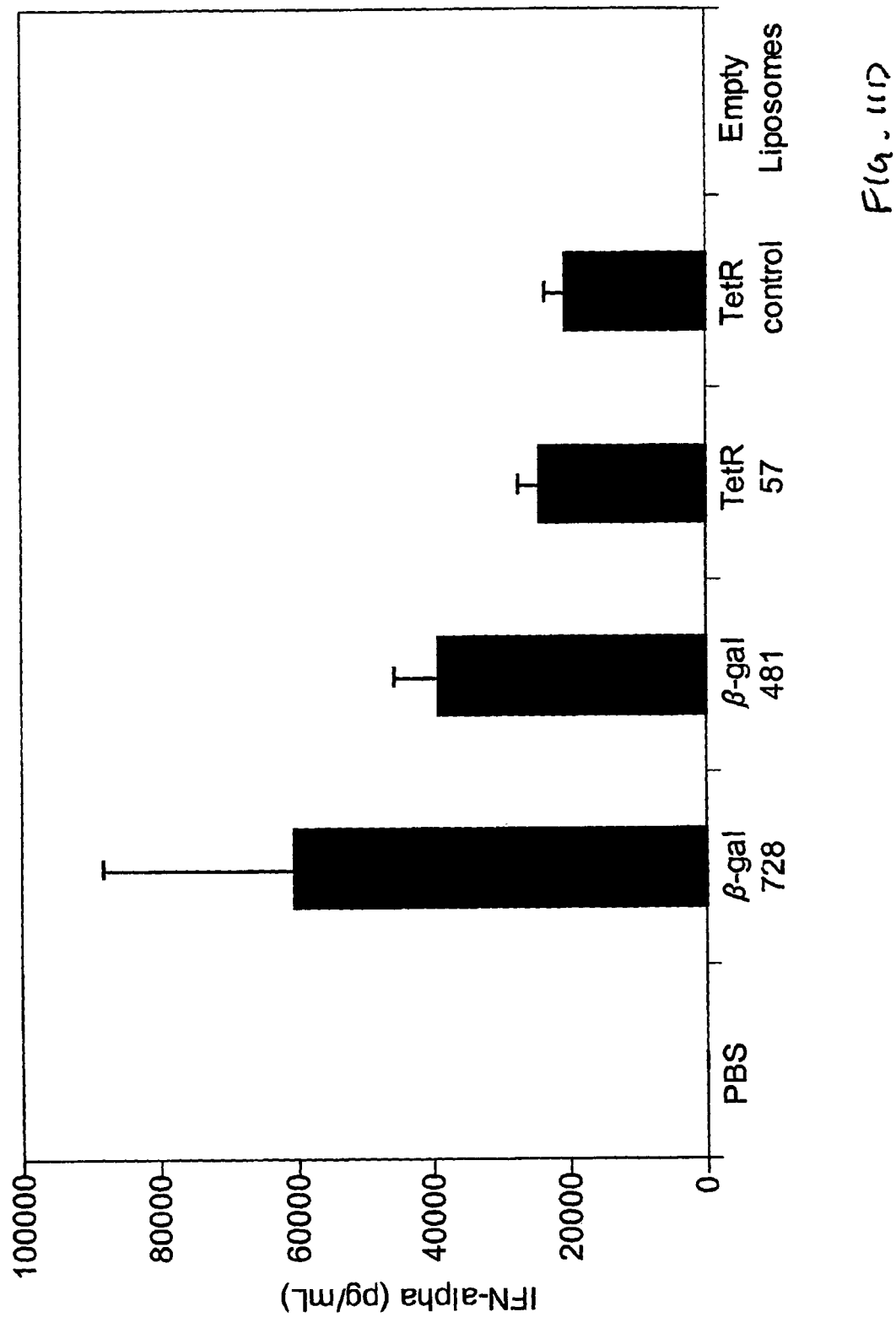
FIG. 11D illustrates data demonstrating that TNF-α, IL-6 and IFN-γ are also induced by stimulatory siRNA.

This general observation that synthetic siRNA could be potent stimulators of an innate cytokine response was confirmed in a second experiment in which mice were treated intravenously with siRNA duplexes targeting β-gal or TetR encapsulated in an alternate liposomal formulation (FIG. 11C). Qualitatively similar responses were also seen in A/J and C57BI/6 strains of mice. Treatment with siRNA was associated with the concurrent production of inflammatory cytokines including TNF-α and IL-6 (FIG. 11C). Maximum cytokine levels were achieved 6-10 h after siRNA administration and had fully resolved to background levels within 24 h. This cytokine response was dependent on the siRNA and required its effective intracellular delivery since neither lipid carriers or the naked siRNA duplexes at equivalent doses induced detectable cytokine elevations (FIGS. 11A, 11C, and 11D). Strikingly, treatment with certain siRNAs, for example duplexes designed to target the breast cancer associated BP1 protein (see, e.g., Fu et al., *Breast Cancer Res.* 5, 82-87 (2003) or its non-targeting sequence control, induced little or no cytokine response in mice even when administered in encapsulated form (FIGS. 11A and 11D). Since all of these synthetic siRNA duplexes have similar chemistries, this finding suggests that the immunostimulatory activity of an siRNA duplex is a function of its nucleotide sequence.

Example 11

The Immune Stimulatory Activity of Sima is Modulated By GU-rich Motifs

Although poorly defined, poly U or U and G rich sequences within ssRNA oligonucleotides have been identified as contributing to their immunostimulatory effects (see, e.g., Heil et al., *Science* 303, 1526-1529 (2004) and Diebold et al., *Science* 303, 1529-1531 (2004)). Our in vivo and in vitro studies demonstrate that immune stimulatory activity of siRNA is modulated by GU-rich motifs Analysis of the six siRNA sequences shown in FIG. 16 initially used in our studies reveals that the highly stimulatory βgal and non-targeting control duplexes contain a 5'-UGUGU-3' internal motif. Since this GU rich motif is not present in the poorly stimulatory BP-1 or BP-1 control duplexes, we hypothesized that this may contribute to the immunostimulatory activity of the siRNA. To test this hypothesis, we designed RNA duplexes containing a single or double base substitution that incrementally disrupt the 5'-UGUGU-3' motif in the βgal control sequence or introduces the same motif into the BP-1 control sequence (FIG. 12A). Series 1; β-gal control (highly stimulatory), β-gal Mod1 (single base substitution) and β-gal Mod2 (double base substitution). Series 2; BP1 control (low stimulatory), BP1 Mod1 (single base substitution) and BP1 Mod2 (double base substitution). Base substitutions are underlined.

In vivo

Figure 12B:
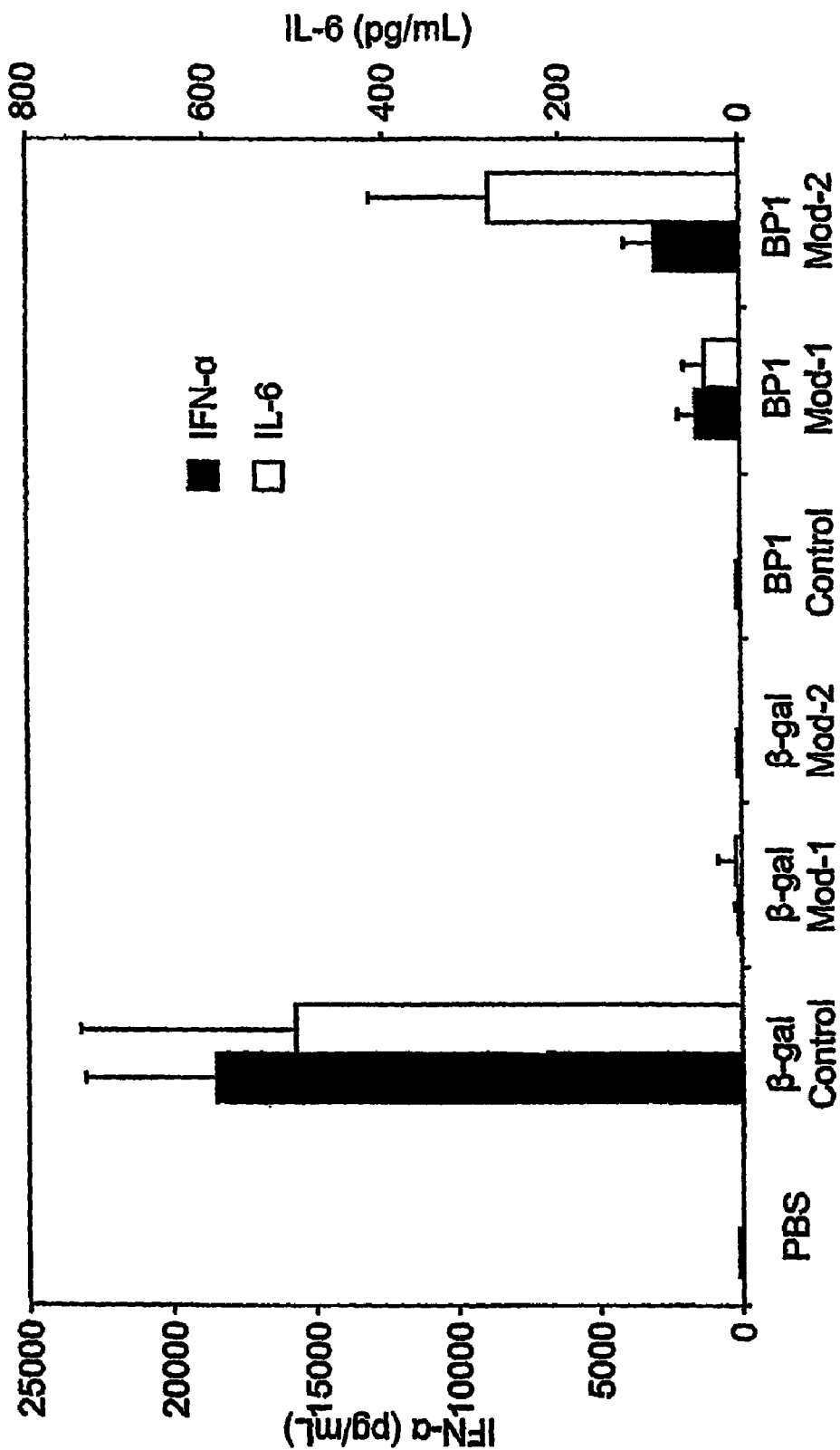
FIG. 12B illustrates data demonstrating that siRNA can be rendered more or less stimulatory by the introduction or disruption of a 5'-UGUGU-3' motif respectively.

Lipid-encapsulated sequence modified siRNA duplexes (50 μg) were intravenously administered to mice. IFN-α and IL-6 were assessed in mouse serum 6 h after administration. The single U to C base substitution in the β-gal siRNA sequence (β-gal Mod1) almost completely abolished both the IFN-α and inflammatory cytokine response when these duplexes were injected into mice (FIG. 12B). A second U to C base substitution (βgal Mod2) that further disrupted the original 5'-UGUGU-3' motif completely abrogated the systemic cytokine response (FIG. 12B). Conversely, a single G to U base substitution in the BP1 control sequence, creating a 5'-UGU-3' motif, rendered the modified RNA duplex immunostimulatory (BP1 Mod 1). This activity was further enhanced by a second base substitution (BP1 Mod2) that fully reconstituted the 5'-UGUGU-3' motif (FIG. 12B).

In vitro

Figure 12C:
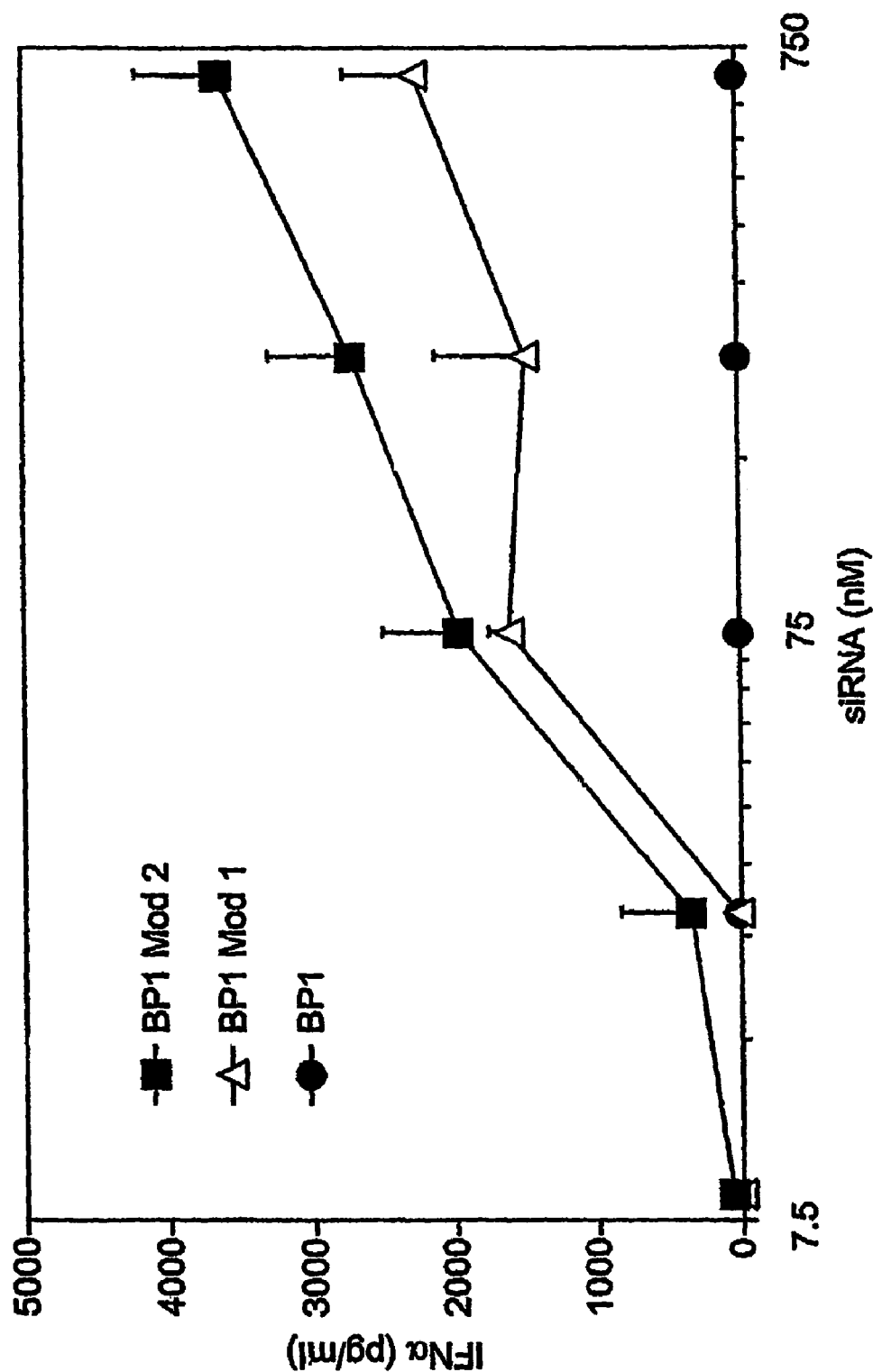
FIG. 12C illustrates data demonstrating that BP-1 siRNA modified to incorporate GU-rich motifs have enhanced immune stimulatory activity.
Figure 12D:
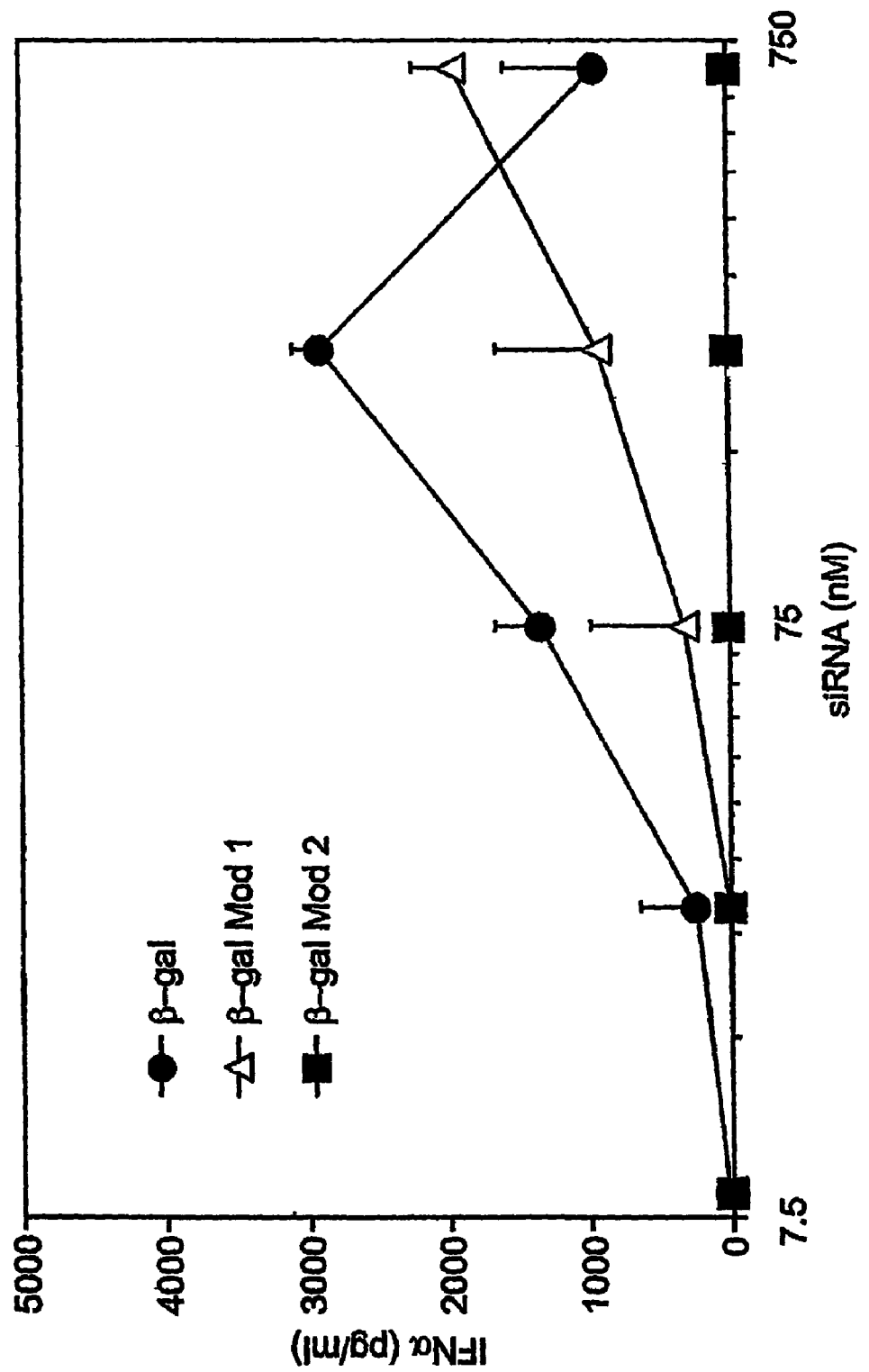
FIG. 12D illustrates data demonstrating that β-gal siRNA modified to delete GU-rich motifs have reduced immune stimulatory activity.

Treatment of human PBMC with the sequence modified BP1 and β-gal RNA duplexes demonstrated that the immunostimulatory activity of these siRNA on human immune cells was regulated by the presence of similar motifs in the siRNA sequence (FIGS. 12C and 12D). These findings support the contention that human and mouse immune cells can recognize broadly similar siRNA sequence motifs based on GU rich sequences. It also indicates that the specificities of this siRNA recognition mechanism are strict enough to allow its disruption by single base pair substitutions within putative immunostimulatory motifs.

Figure 12F:
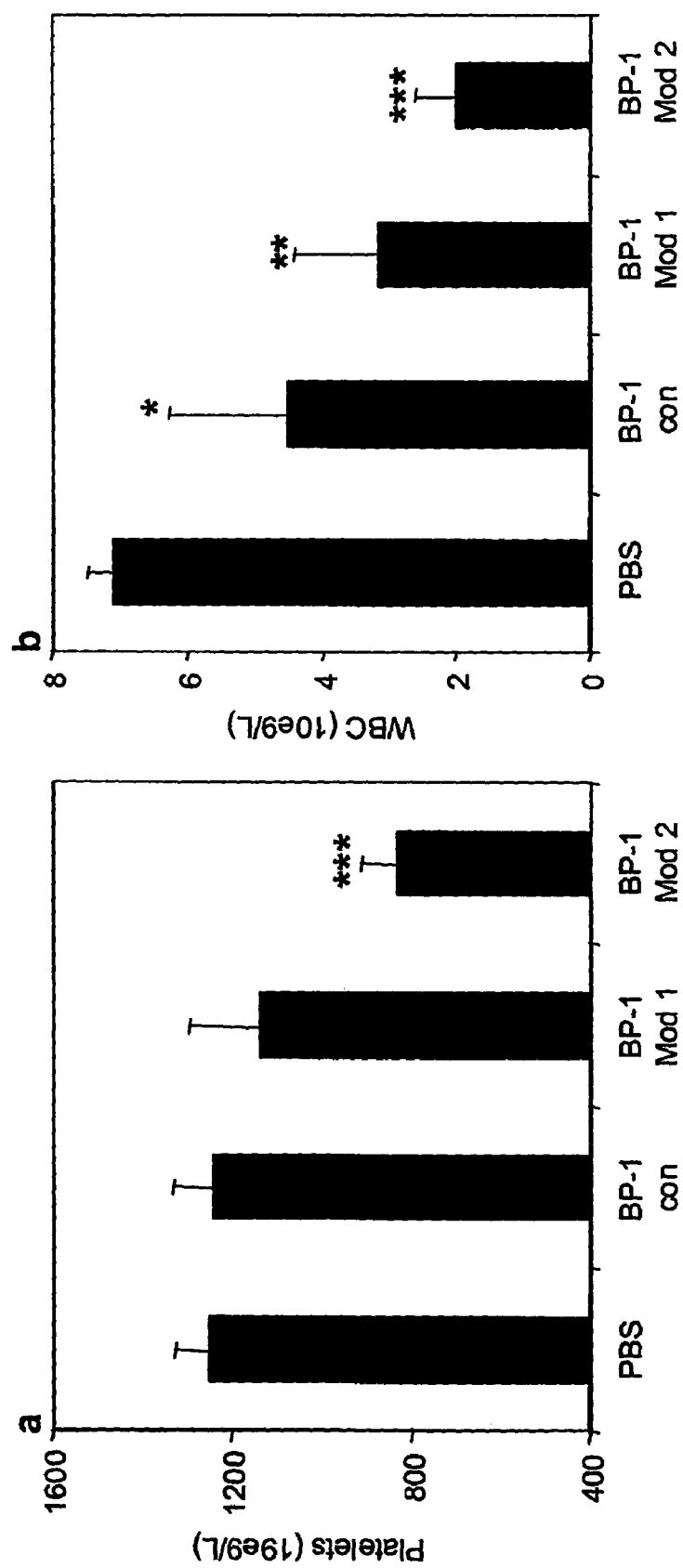
FIG. 12F illustrates data demonstrating that there is a drop in peripheral white blood cell and platelet counts associated with administration of immunostimulatory modified BP-1 siRNA.

Systemic inflammatory reactions are often accompanied by a perturbation of hematological parameters. These effects can include a transient reduction in leukocyte and platelet numbers due to the margination of these cells from the peripheral blood. Intravenous treatment of mice with β-gal and other immunostimulatory siRNAs resulted in a rapid reduction in platelets and white blood cells (FIG. 12E) that was attributable to the selective loss of lymphocytes from the peripheral blood. This reaction was transient; blood cell numbers returned to baseline levels within 72 h of siRNA administration. The extent of these toxicities correlated with the degree of cytokine release induced by each siRNA duplex. Treatment with sequence modified β-gal RNA duplexes that induced minimal cytokine release had little or no effect on platelet or white blood cell counts (FIGS. 12D and E). Qualitatively similar results were obtained with the BP-1 series of modified siRNA (FIGS. 12C and 12F). These findings demonstrate that the use of synthetic siRNA with non-stimulatory sequences may alleviate potential toxicities associated with their systemic administration.

FIGS. 12C and 12D illustrate data demonstrating that similar sequence motifs regulate the immune stimulatory activity of siRNA on human cells. IFN-α induction from human PBMC after overnight culture with (c) encapsulated sequence modified BP 1 or (d) β-gal siRNA. Values are mean+SD. of triplicate cultures and representative of 2 separate experiments. FIG. 12D illustrates data demonstrating that there is a drop in peripheral white blood cell and platelet counts associated with administration of immunostimulatory siRNA is ameliorated by RNA sequence modifications. Mice were treated with 50 μg encapsulated siRNA and their peripheral WBC and platelet counts recorded at 48 h after administration. Immunostimulatory β-gal siRNA caused a substantial drop in both platelet and WBC numbers. These effects were ameliorated by the selective base substitutions in β-gal Mod1 and Mod2 sequences.

Example 12

In vitro Properties of Lipid Encapsulated siRNA

Murine Neuro2a cells stably expressing firefly luciferase were treated with luciferase siRNA or the non-targeting control siRNA encapsulated in lipid vesicles. The siRNA sequences are provided in FIG. 16. All siRNA were synthesized with a 3'-UU overhang on each strand. Immunostimulatory GU-rich motifs (e.g., 5'-UGU-3' and 5'-UGUGU-3' motifs) are underlined. Liposome encapsulation of siRNA was performed as described in Example 1 above. Luciferase expression after 48 h culture is expressed as percent of media only control cultures. Values are mean+SD of triplicate cultures. The results are shown in FIG. 13 and demonstrate that lipid encapsulated siRNA is effective at mediating RNAi in vitro.

Example 13

Lipid-Complexed siRNA and Polycation-Complexed siRNA Induce Inflammatory Cytokine Responses In vitro experiments demonstrate that both lipid-complexed siRNA and polycation-complexed siRNA are immunostimulatory.

Lipid-complexed siRNA

Figure 14A:
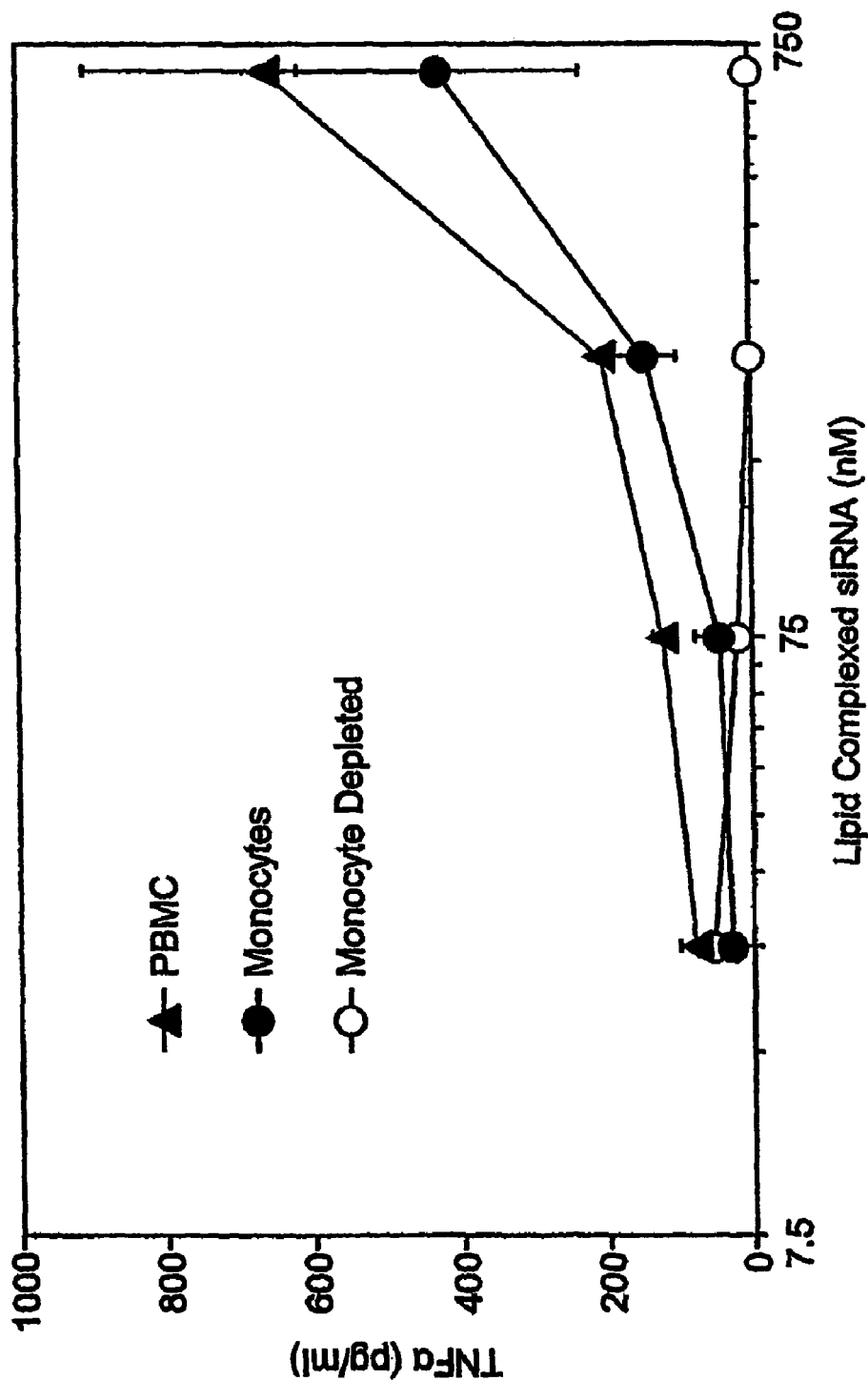
FIG. 14A illustrates data showing levels of TNF-α produced in response to lipid-siRNA complexes.
Figure 14B:
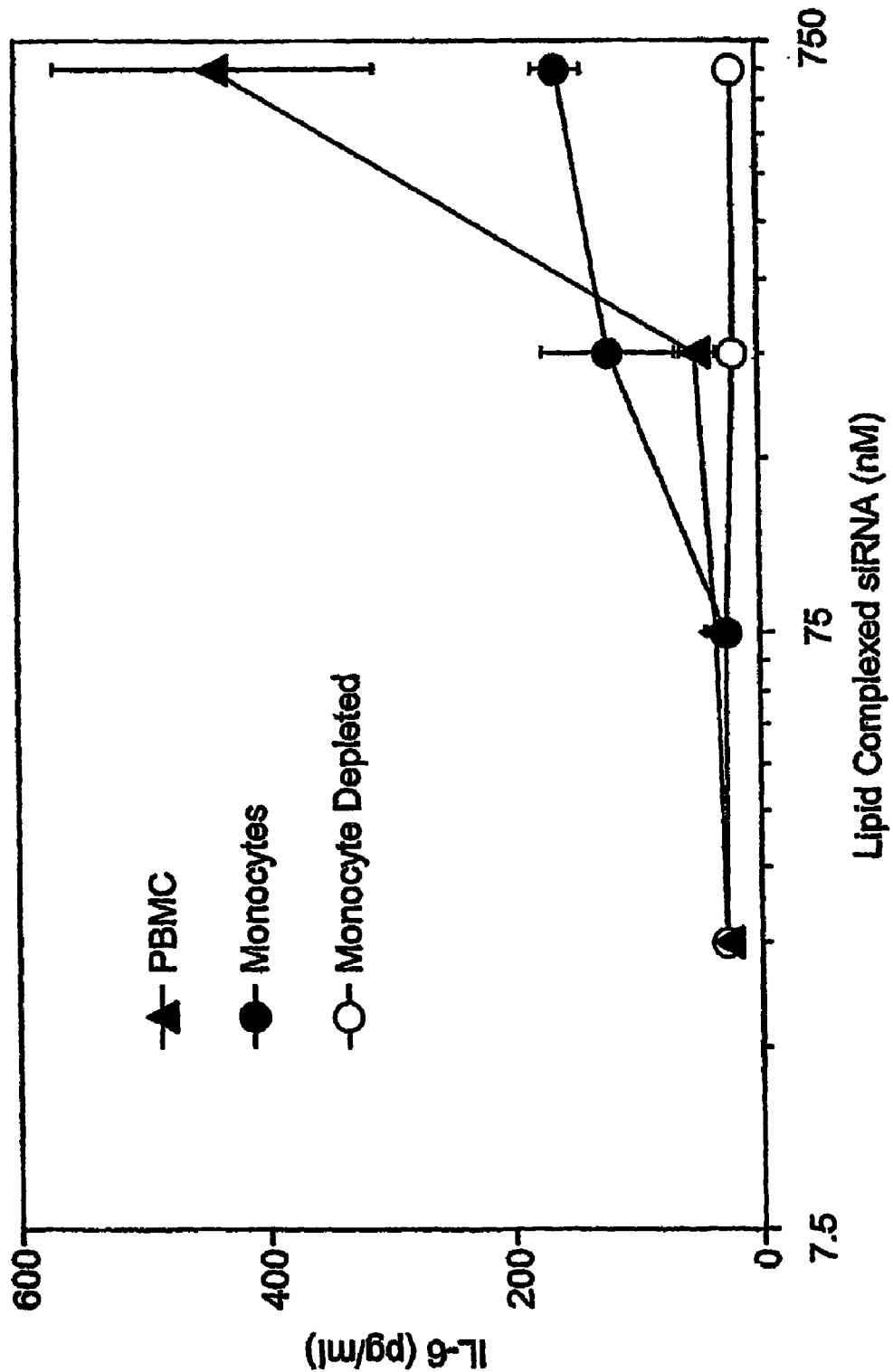
FIG. 14B illustrates data showing levels of IL-6 produced in response to lipid-siRNA complexes.

Human PBMC, monocytes or monocyte depleted PBMC fractions were cultured overnight with Oligofectamine complexed β-gal siRNA. The inflammatory cytokines, IL-6 and TNF-α, were measured in the culture supernatants. FIG. 14A illustrates data showing 15 TNF-α: levels. FIG. 14B illustrates data showing IL-6 levels. Values are mean of triplicate cultures+/−SD. In a separate experiment, relatively high doses of lipid complexed siRNA were able to induce IL-6 and TNF-α production from purified monocytes. FIGS. 14A and 14B illustrate data demonstrating that freshly isolated monocytes can be stimulated with high doses of lipid-complexed siRNA to produce inflammatory cytokines.

Figure 14C:
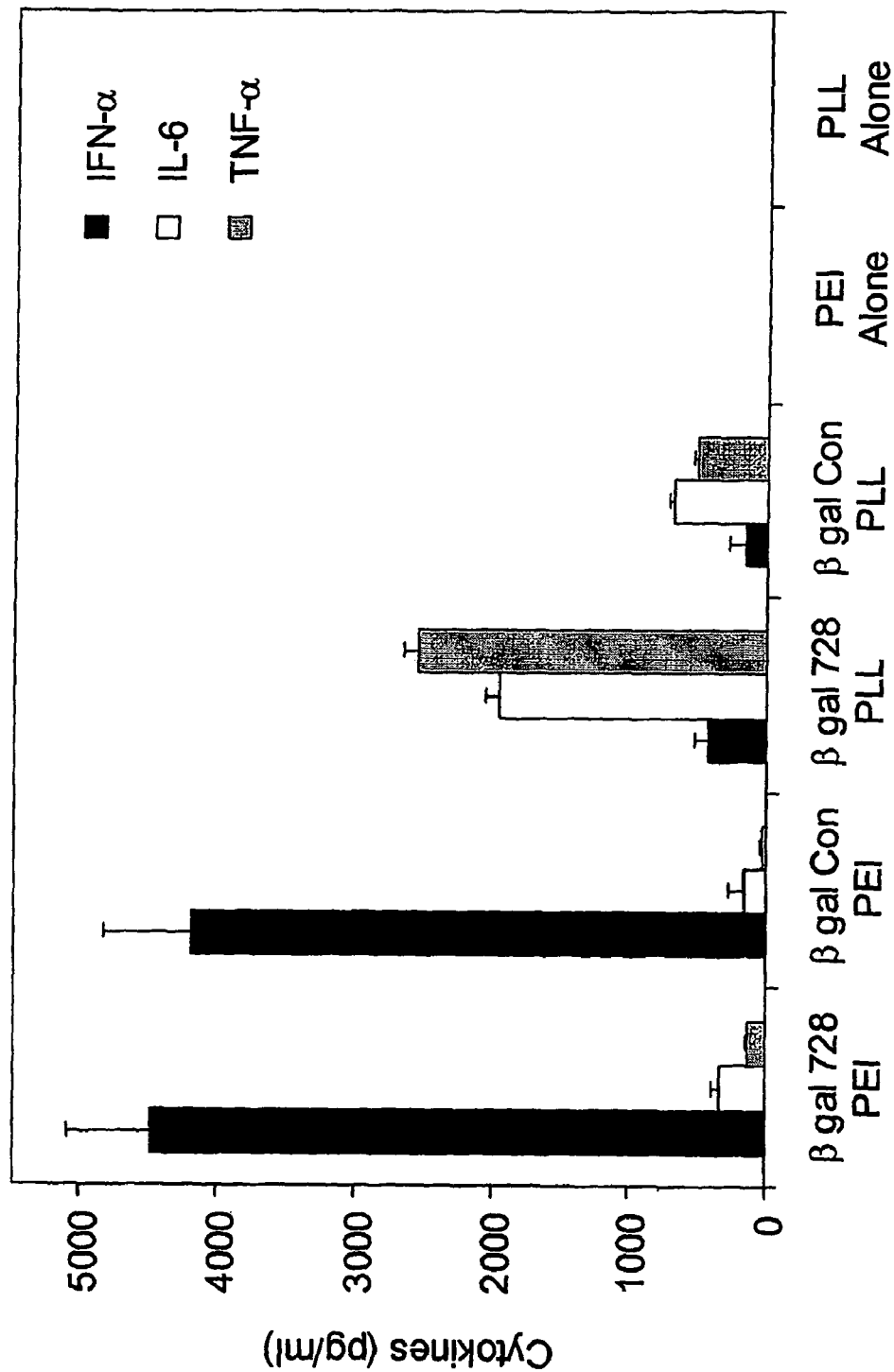
FIG. 14C illustrates data showing levels of IFN-α, IL-6, and TNF-α produced in response to polycation-siRNA complexes.

Polycation-complexed siRNA siRNA Complexed with the Polycations Polyethylenimine or Poly-L-Lysine Also Activate Potent Cytokine Responses From Human PBMC. β-gal 728 or β-gal control siRNA were mixed with either 10 KDa polyethylenimine (PEI) or poly-L-lysine (PLL) as described in Example 1 above to form polyplexes. Human PBMC were stimulated with polyplexes at 3 μg/mL siRNA or polycation alone at equivalent concentrations. IFN-α, IL-6 and TNF-α were measured in the culture supernatants after 24 h. Values are mean+SD of triplicate cultures. All data are representative of at least 3 separate experiments. FIG. 14C illustrates data demonstrating that freshly isolated monocytes can be stimulated with high doses of polycation-complexed siRNA to produce inflammatory cytokines.

Example 14

Sequence Modification of siRNA Ameliorates their Systemic Toxicities.

Systemic inflammatory reactions are often accompanied by a perturbation of hematological parameters. These effects can include a transient reduction in leukocyte and platelet numbers due to the margination of these cells from the peripheral blood. Intravenous treatment of mice with βgal and other immunostimulatory siRNAs resulted in a rapid reduction in platelets and white blood cells (FIG. 12E) that was attributable to the selective loss of lymphocytes from the peripheral blood. This reaction was transient; blood cell numbers returned to baseline levels within 72 h of siRNA administration. At higher siRNA doses (5-10 mg/kg; single dose) more apparent toxicities were observed including body weight loss, hunched posture and piloerection. These toxicities were dependent on the encapsulated siRNA and their extent correlated with the degree of cytokine release induced by each siRNA duplex. Treatment with sequence modified β-gal RNA duplexes that induced minimal cytokine release had little or no effect on platelet or white blood cell counts (FIGS. 12D and 12E) and had no apparent effect on the general condition of the animal. Qualitatively similar results were obtained with the BP-1 series of modified siRNA (FIG. 12F). These findings demonstrate that the use of synthetic siRNA with non-stimulatory sequences can alleviate potential toxicities associated with their systemic administration.

Example 15

Immunostimulatory Activity of siRNA is not Caused by Contaminants Such as ssRNA

To confirm that the immunostimulatory properties of the siRNA duplexes were not caused by contaminants such as ssRNA, siRNA duplexes were subjected t polyacrylamide gel electrophoresis (PAGE) purification and PAGE purification followed by RNAse treatment. siRNA thus purified and treated was cultured with human PBMC in vitro or administered to mice in vivo to confirm retention of immunostimulatory properties. (02461 PAGE purified β-gal control siRNA duplex or its constituent sense and antisense ssRNA oligonucleotides were treated for 10 min with 0.5 µg/mL RNase A in high salt buffer (2 mg/mL RNA in 300mM NaCl) to selectively degrade ssRNA. RNA samples before and after RNase A treatment run on 20% non-denaturing polyacrylamide gels (500 ng/lane) confirmed selective degradation of ssRNA.

β-gal control duplex, GU rich sense and complimentary antisense ssRNA's were digested with RNase A in high salt buffer (2 mg/mL RNA in 300 mM NaCl) for 5 or 15 mins. RNA was then complexed with 10 kDa PEI. 200 nM RNA was added to human PBMC cultures and IFN-α induction was assayed after overnight culture. FIG. 15B illustrates data demonstrating that GU rich sense ssRNA induced no detectable IFN-α following RNase A treatment and that RNase A treatment had minimal effect on the induction of IFN-α by siRNA duplex compared to untreated samples. Values are mean+SD of triplicate cultures. Data is representative of 3 separate experiments.

Figure 15A:
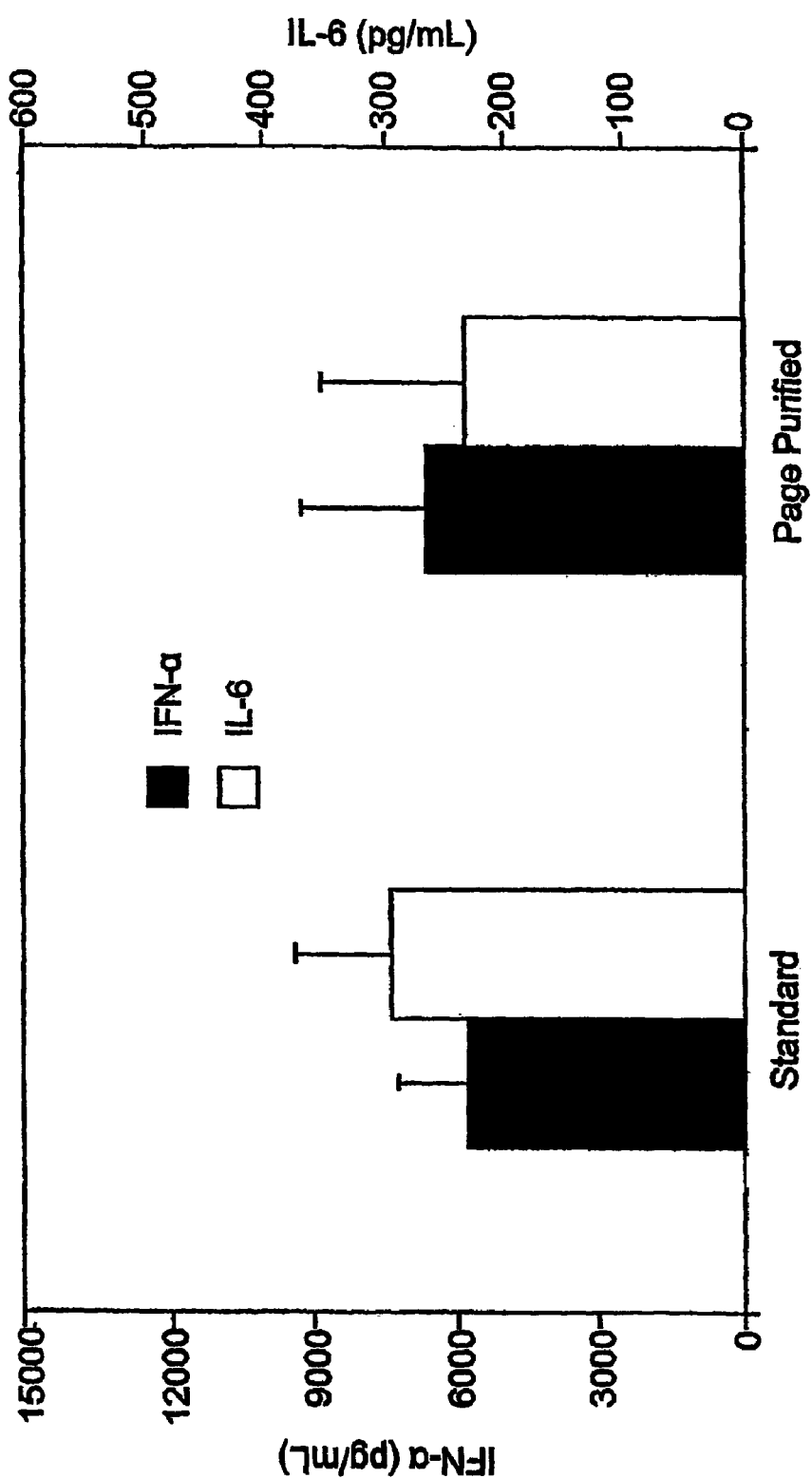
FIG. 15A illustrates data demonstrating that PAGE purification of the siRNA duplex does not affect its immunostimulatory activity.
Figure 15B:
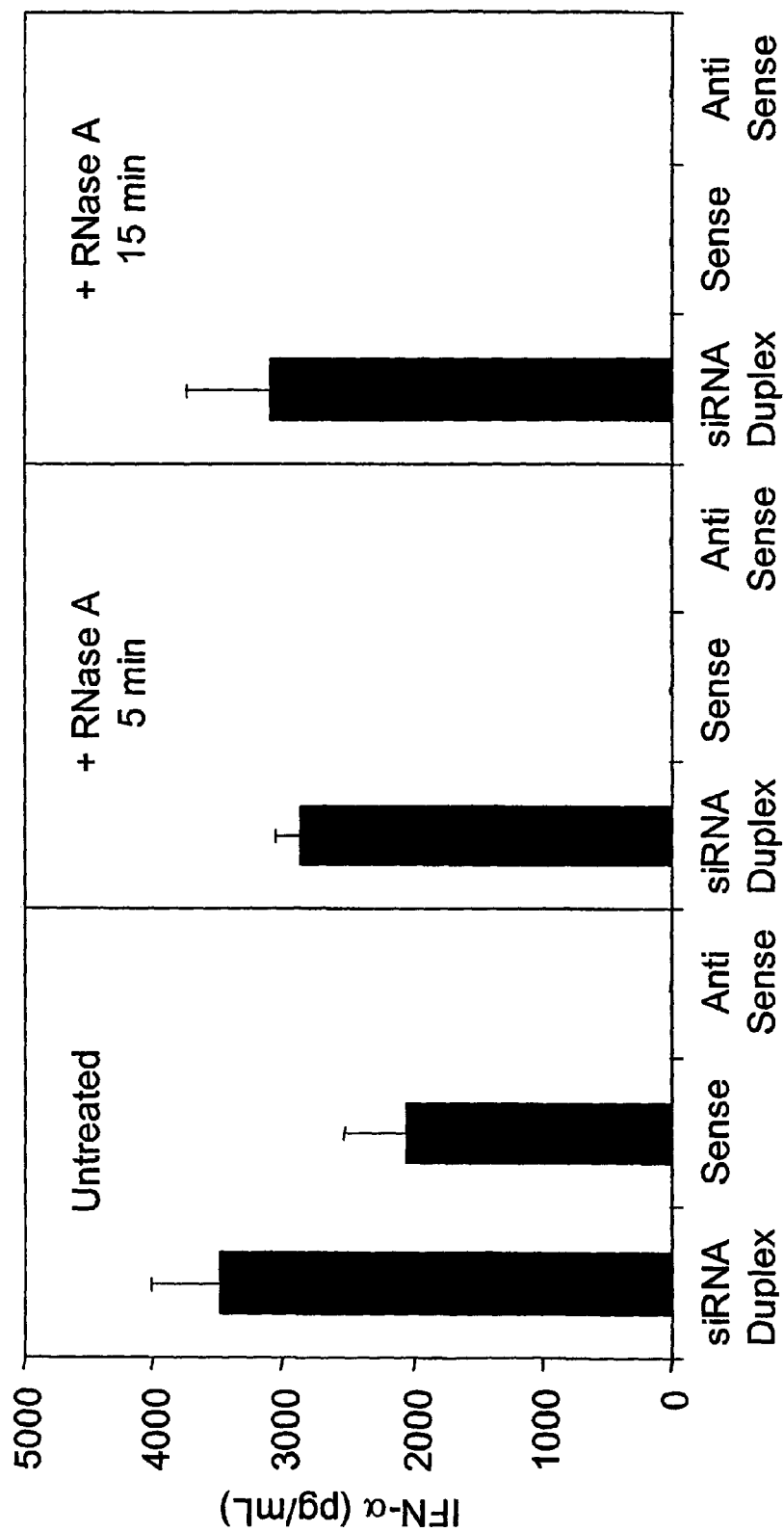
FIG. 15B illustrates data demonstrating that GU rich sense ssRNA induced no detectable IFN-α following RNase A treatment and that RNase A treatment had minimal effect on the induction of IFN-α by siRNA duplex compared to untreated samples.

FIG. 15A illustrates data demonstrating that PAGE purification of the siRNA duplex does not affect its immunostimulatory activity. Mice were treated intravenously with 50 µg of standard or PAGE purified Luciferase siRNA encapsulated in liposomes. Serum IFN-α and IL-6 were measured after 6 h. PAGE purification of the siRNA duplex was performed by Dharmacon (Lafayette, Colo.). Values are mean+SD (n=4 mice).

Example 16

Stimulation of pDC by siRNA Requires Endosomal Acidification

Human and murine pDC have been identified as the primary producers of IFN-α in response to CpG DNA (see, e.g., Hornung et al., J. Immunol. 168, 4531-4537 (2002); Kadowaki et al., J. Exp. Med. 194, 863-869 (2001); and Asselin-Paturel et al., J. Immunol. 171, 6466-6477 (2003)) and ssRNA (see, e.g., Diebold et al., 2004, supra and Heil et al., Science 303, 1526-1529 (2004)) due to their selective expression of TLR9 and TLR7, respectively. Cell fractionation studies using magnetic bead separation revealed BDCA4+pDC (see, e.g., Dzionek et al., J. Immunol. 165, 6037-6046 (2000) and Jego et al., Immunity 19, 225-234 (2003)) to be the primary human PBMC cell type responsible for the IFN-α response to lipid encapsulated siRNA (FIG. 9). By contrast, purified CD 14+ monocytes produced little IFN-α when cultured with stimulatory siRNA whereas monocyte depleted PBMC retained full capacity to respond (FIG. 9). In a separate experiment, relatively high concentrations of lipid complexed siRNA were able to induce IL-6 and TNF-α production from purified monocytes (FIG. 14). These biases in the immune response to either encapsulated or complexed siRNA may reflect differences in how charged siRNA complexes and neutral liposomes are taken up into cells in vitro and the context in which the siRNA is subsequently presented.

Recognition of nucleic acids by TLRs typically occurs within the endosomal/lysosomal compartment of cells. This has been demonstrated for the stimulation of TLR3 (see, e.g., Matsumoto et al., J. Immunol. 171, 3154-3162 (2003)), TLR7/8 (see, e.g., Diebold et al., Science 303, 1529-1531 (2004); Lund et al., PNAS USA 101, 5598-5603 (2004); and Heil, F. et al., Eur. J. Immunol. 33, 2987-2997 (2003)) and TLR9 (see, e.g., Ahamad-Nejad et al., Eur. J. Immunol. 32, 1958-1968 (2002) and Latz et al., Nature Immunol. 5, 190-198 (2004)) by their respective ligands; dsRNA, ssRNA and CpG DNA. Endosomal TLR signaling can be blocked by the lysosmotropic agent chloroquine which acts to inhibit endosome acidification (see, e.g., Yi et al., J. Immunol. 160, 4755-4761 (1998) and Hacker et al., Embo J. 17, 6230-6240 (1998)). Chloroquine inhibited the siRNA mediated release of IFN-α and IL-6 from human PBMC in a dose dependent manner (FIGS. 4A and 4B). This degree of sensitivity to chloroquine (IC90~2 µM) is in agreement with other studies using defined nucleic acid based TLR ligands (see, e.g., Diebold et al., Science 303, 1529-1531 (2004); Latz et al., 2004, supra; and Leadbetter et al., Nature 416, 603-607 (2002)) suggesting that synthetic siRNA may also be recognized by an endosomally located TLR.

Example 17

Figure 18:
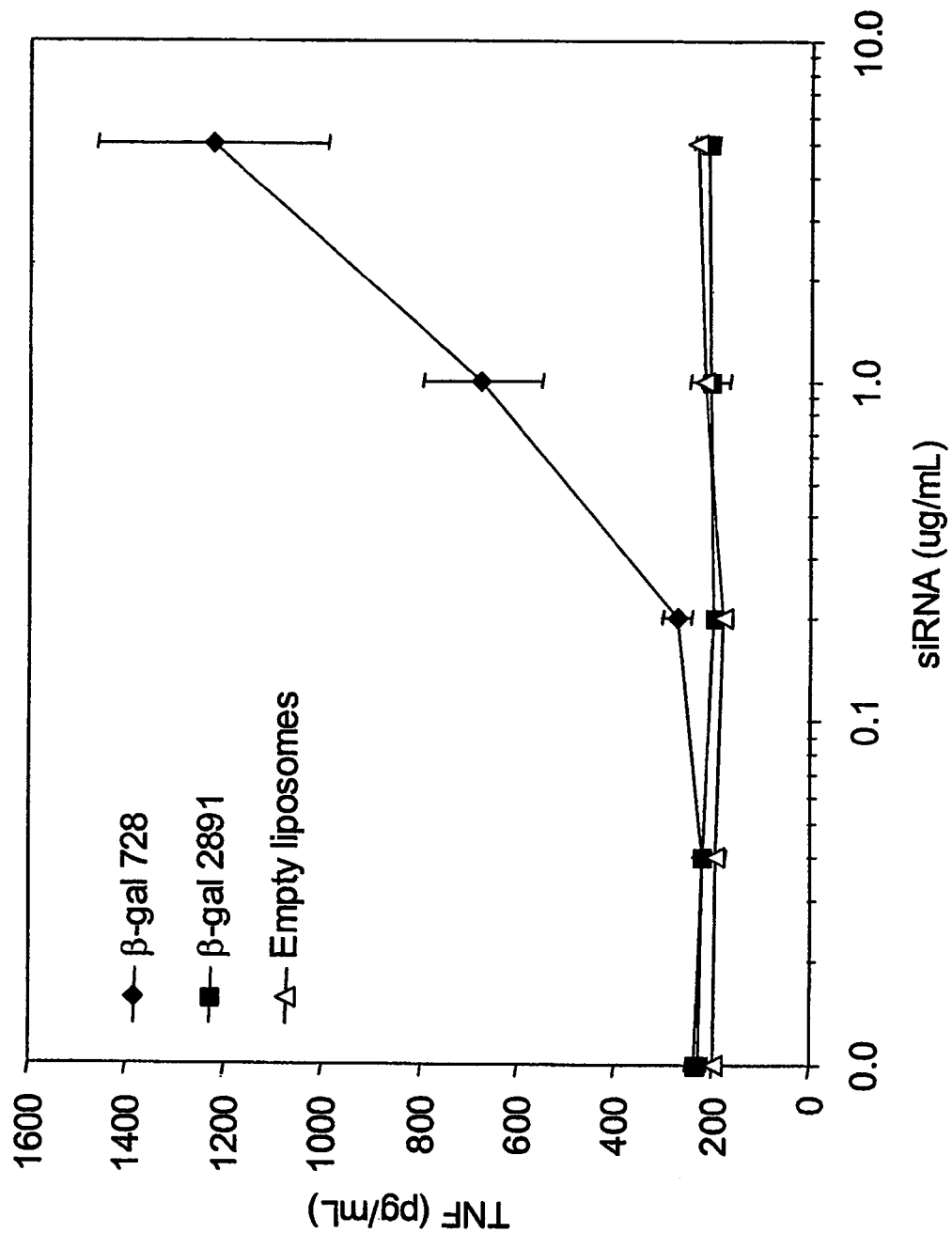
FIG. 18 illustrates data demonstrating that the cytokine response to siRNA in vivo is not limited to pDC cells.

Lipid Encapsulated siRNA Stimulates Inflammatory Cytokine Release from RAW 264 Cells in a Sequence Dependent Manner To confirm that the cytokine response to siRNA in vivo reflects activation of multiple cell types of which IFN-α production by pDC plays a significant but not exclusive role, studies using the murine monocytic cell line RAW 264 were conducted. RAW 264 cells express a range of immune receptors including functional TLR7. RAW 264 cells were plated into 96 well plates, allowed to adhere overnight then treated with lipid encapsulated β-gal 728, β-gal 2891 siRNA or empty liposomes for 48 h. TNF-α was assayed in culture supernatants. Values are mean+/−SD of triplicate cultures. Data are representative of 3 separate experiments. The results demonstrate that the cytokine response to siRNA is not limited to pDC cells and are shown in FIG. 18.

Example 18

Rational Design of Non-Stimulatory siRNA with RNAi Activity

Figure 17B:
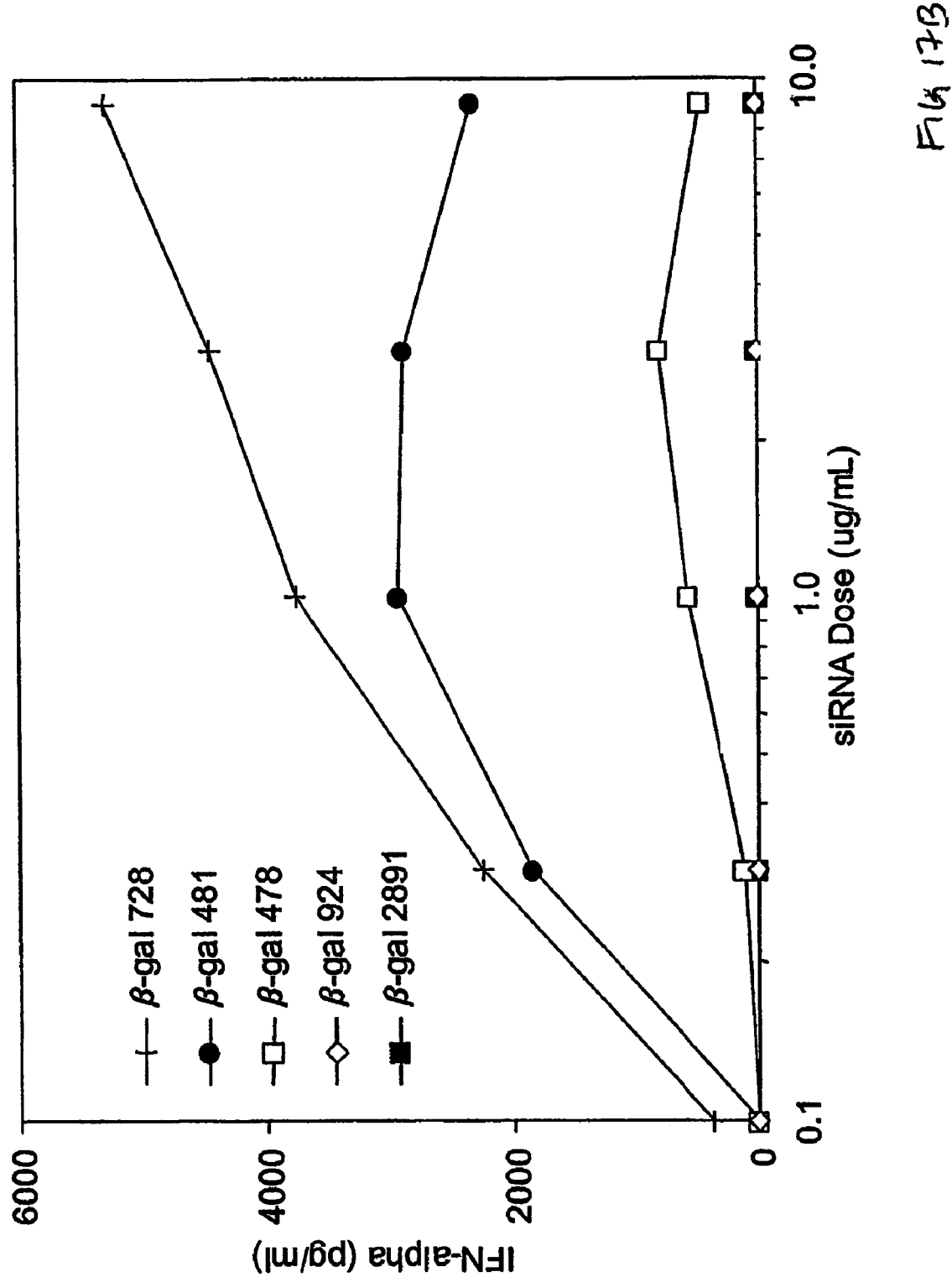
FIG. 17B illustrates data demonstrating the immunostimulatory activity of novel β-gal siRNA on human PBMC.

To demonstrate the applicability of our findings to the development of functional, non-immunostimulatory siRNA, we designed a series of novel siRNA sequences targeting β-gal that avoided GUGU or poly U motifs (FIG. 17A). The immunostimulatory activity of these novel siRNA was significantly reduced compared to the β-gal 728 duplex used in initial studies. IFN-α induction by lipid encapsulated β-gal 478 siRNA in human PBMC cultures was reduced approximately 10-fold while β-gal 924 and 2891 duplexes induced no detectable IFN-α response even at high concentrations (FIG. 17B). A similar reduction in the level of cytokine induction was observed in mice following intravenous administration. These novel β-gal siRNA possessed functional RNAi activity. Lipid encapsulated β-gal 478 and 728 siRNA were equally effective at inhibiting β-gal protein expression in stably transfected Neuro2a (FIGS. 17C and 17D) and CT-26 cell lines. In comparison, β-gal 924 and 2891 siRNA were less potent at mediating RNAi although some degree of target knockdown was achieved at higher nucleic acid concentrations (FIG. 17C).

The non-targeting sequence control duplex had no effect on β-gal expression in the neuroblastoma (FIGS. 17C and 17D) or carcinoma cell lines used in these in vitro studies despite its potent induction of cytokine responses in immunological systems (FIGS. 11 and 12).

Figure 17C:
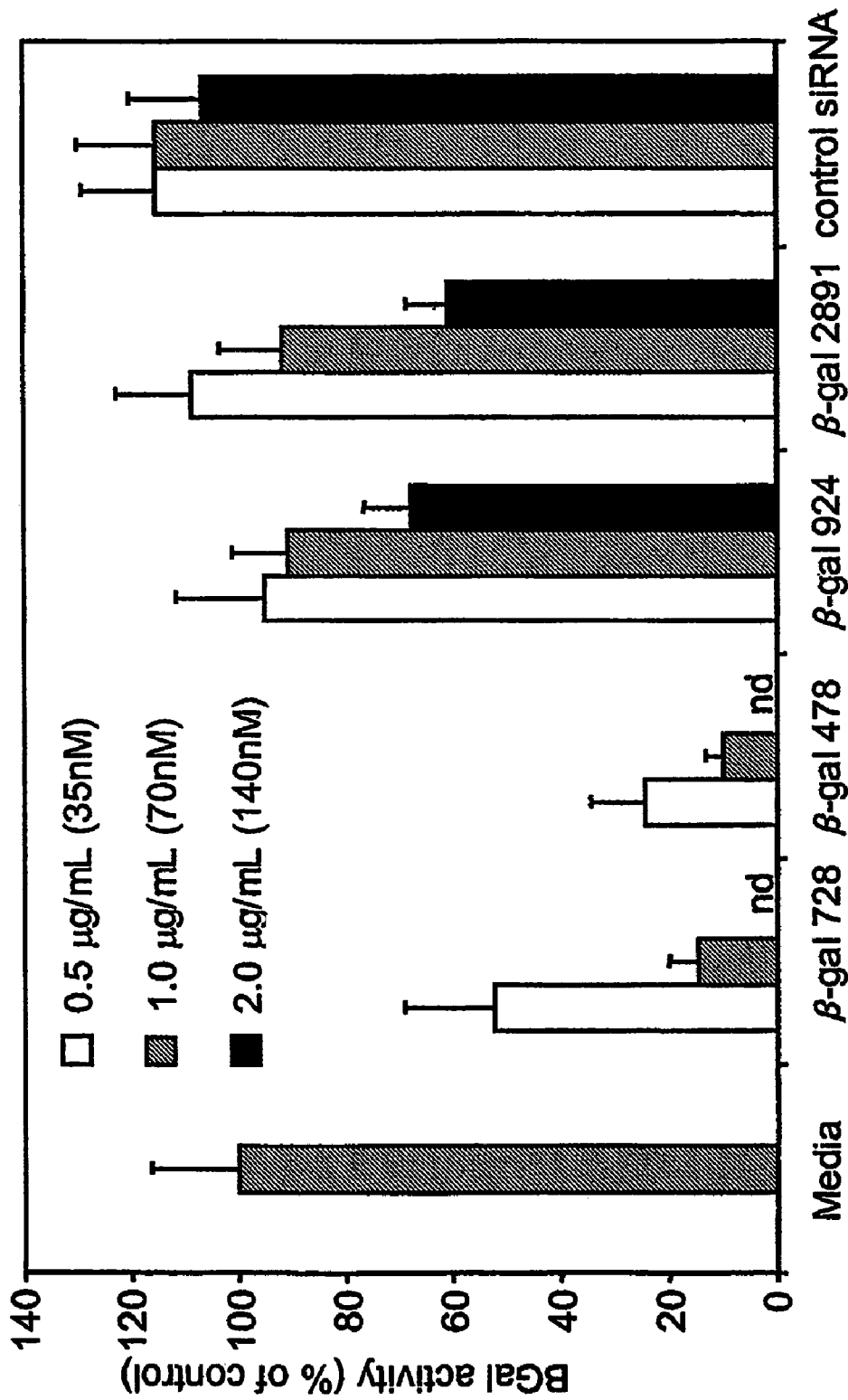
FIG. 17C illustrates data demonstrating inhibition of β-gal activity by novel β-gal targeting siRNA in Neuro 2A cells.
Figure 17D:
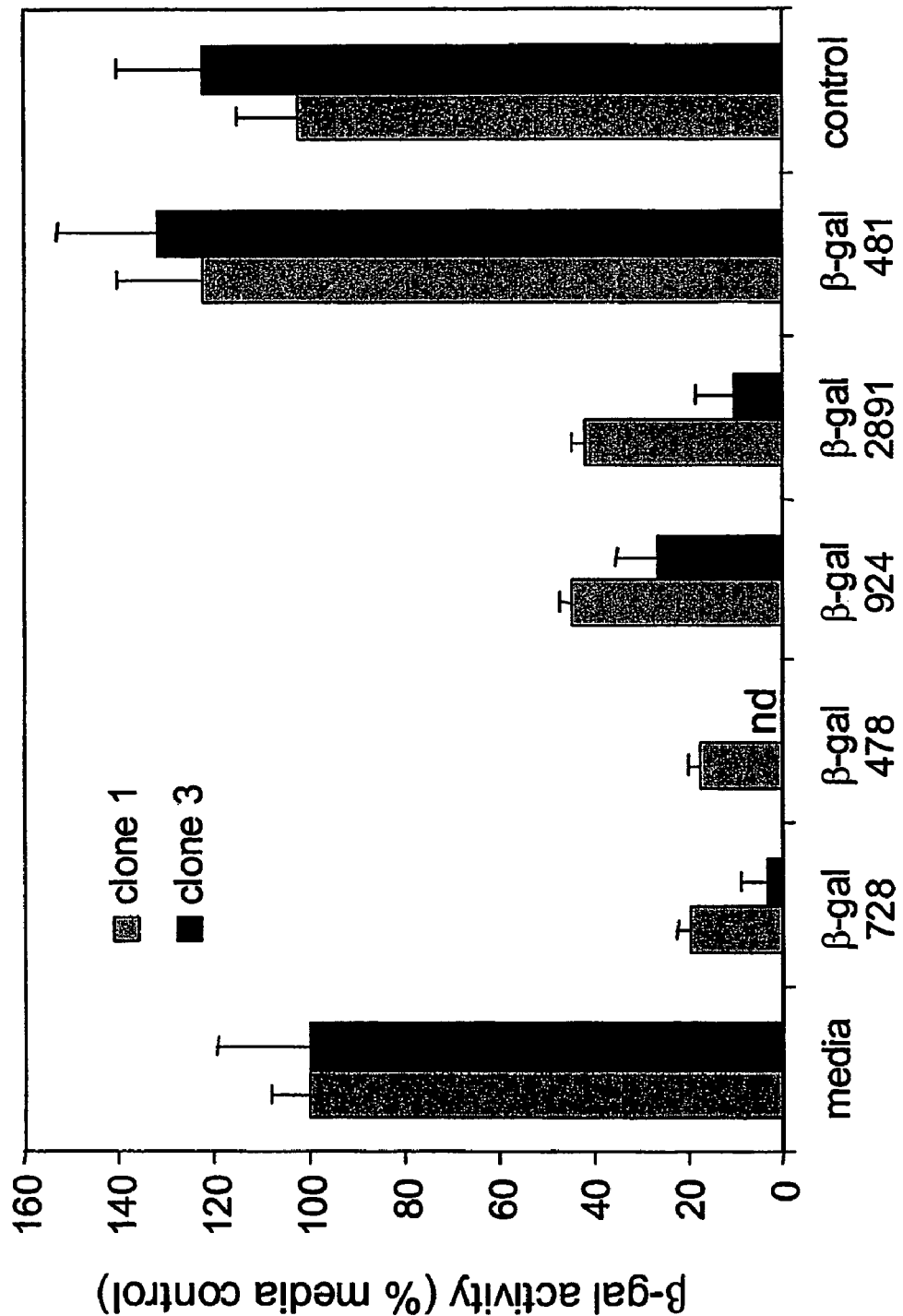
FIG. 17D illustrates data demonstrating inhibition of β-gal activity by GU-rich β-gal targeting siRNA in Neuro2A cells.

FIG. 17 illustrates data demonstrating that siRNA can be designed that are active in mediating RNAi and have minimal capacity to activate innate immune responses. FIG. 17A sets forth siRNA sequences designed to target β-gal (codon start sites 478, 924, and 2891) that lack putative immunostimulatory motifs. FIG. 17B illustrates data demonstrating the immunostimulatory activity of novel β-gal siRNA. Interferon-γ induction from human PBMC cultured overnight with lipid-encapsulated β-gal 728, 481, 478, 924, or 2891 siRNA duplexes. Values are from pooled triplicate cultures at each nucleic acid concentration. Data is representative of 2 separate experiments. FIG. 17C illustrates data demonstrating inhibition of Regal activity by novel β-gal targeting siRNA. Neuro2a-LacZ cells that stably express β-gal protein were cultured for 48 h with lipid encapsulated β-gal siRNA or non-targeting control siRNA. β-gal enzyme activity was assayed in cell lysates and expressed as percent of media only control cultures. nd=no detectable β-gal activity. Values represent mean+/−SD of triplicate cultures. Data is representative of 3 separate experiments. FIG. 17D illustrates data demonstrating inhibition of β-gal activity by GU-rich β-gal targeting siRNA. Lipid encapsulated β-gal siRNA or non-targeting β-gal control siRNA (100 nM) were cultured for 48 h with either Neuro2a LacZ clone 1 or clone 3 cells that express 2534 +/−334 and 1030+/−118 mU β-gal /mg protein respectively. β-gal enzyme activity was assayed in cell lysates and expressed as percent of media only control cultures. nd=no detectable β-gal activity. Values represent mean+/−SD of triplicate cultures. Data is representative of 3 separate experiments.

These findings demonstrate that the selection of mRNA target sequences lacking putative immunostimulatory motifs can generate siRNA duplexes with potent RNAi activity and minimal immune system stimulation. We suggest that such screening and analyses of siRNA become an important selection criteria when developing siRNA for in vivo and therapeutic use.

We have identified a potent mechanism of immune stimulation triggered by the intracellular delivery of synthetic siRNA to cells of the innate immune system. This response to the siRNA molecule leads to the release of inflammatory cytokines and high level production of type I interferons. Significantly, highly stimulatory siRNA were found to activate both freshly isolated human PBMC in vitro (<0.1 μg/mL; ~7.5 nM) and the mouse immune system in vivo (<1 μg; ~0.05 mg/kg) at concentrations routinely employed in RNAi studies to achieve effective knockdown of the target protein. These findings have significant implications for the development of siRNA for in vivo use due to the potential for off target gene effects and toxicities associated with inflammatory responses and the induction of cytokines.

As a hallmark of viral infection, dsRNA can activate several host defense mechanisms including TLR3 (see, e.g., Alexopoulou et al., *Nature* 413, 732-738 (2001)), PKR (see, e.g., Saunders and Barber *FASEB J.* 17, 961-983 (2003)) and other, as yet defined, TLR-independent mechanisms (see, e.g., Diebold et al., *Nature* 424, 324-328 (2003); Hoebe et al., *Nat. Immunol.* 4, 1223-1229 (2003); and Akira and Takeda, *Nature Rev. Immunol.* 4, 499-511 (2004)). Recent evidence suggests that both synthetic and vector-derived siRNA molecules have the potential to activate PKR (see, e.g., Sledz et al., *Nature Cell Biol.* 5, 834-839 (2003); Bridge et al., *Nature genetics* 34, 263-264 (2003); and Kim et al., *Nat. Biotechnol.* 22, 321-325 (2004)) or TLR3-mediated pathways (see, e.g., (see, e.g., Karikó et al., *J. Immunol.* 172, 6545-6549 (2004)) in vitro particularly at high nucleic acid concentrations. Activation of these pathways however is not considered to be dependent on the specific nucleotide sequence of the RNA. This is in striking contrast to the immune response elicited by synthetic siRNA in our studies that was strictly dependent on the nucleotide sequence of the siRNA duplex and could be elicited by relatively low doses of nucleic acid.

By selective base substitutions, we have defined putative immunostimulatory sequence motifs within siRNA duplexes. These are based on G and U rich regions exemplified by the 5'-UGUGU-3' motif identified in the β-gal 728, β-gal control and BP1 Mod 2 RNA duplexes. A single base substitution to disrupt this motif (β-gal Mod 1 RNA) resulted in a duplex with significantly lower immunostimulatory capacity, thus highlighting the role of this motif in activating immune cells that take up the siRNA. Results from modifying the non-immunostimulatory BP-1 control siRNA by a single base substitution (see FIG. 12) suggest that the inclusion of a single GU-rich motif (e.g., a 5'-UGU-3' motif) within the siRNA can be sufficient to render the duplex immunostimulatory. It is of note that the two Luc siRNA sequences that induce moderate cytokine production also contain 5'-UGU-3' motifs (FIG. 16). The effects of relatively minor sequence modifications on the immunostimulatory activity of siRNA is further demonstrated by the comparison of β-gal 478 and β-gal 481 (FIG. 17B) whose mRNA target sequences overlap by 16 of 19 bases (FIG. 17A, FIG. 16). The resulting siRNA sequences differ by only three terminal base pairs, however β-gal 481 is a significantly more potent cytokine inducer compared to β-gal 478. We speculate that this difference results from the introduction of a U-rich 3' terminus in the β-gal 481 duplex based on previous observations that poly U RNA species can be immunostimulatory (see, e.g., Diebold et al., *Science* 303, 1529-1531 (2004)).

Taken together, our findings indicate that the immunostimulatory sequence motifs in siRNA are likely to occur at relatively high frequency in conventionally designed synthetic siRNA. This is supported by data reported here on 16 RNA duplexes and our analysis of more than 20 additional siRNA against diverse targets in which a certain degree of immune activation by the siRNA is the norm rather than the exception, especially at high nucleic acid concentrations. We have demonstrated in these studies that the design of siRNA duplexes that are both active in mediating RNAi and have minimal or no detectable capacity to activate innate immune responses is feasible based on target sequence selection.

The nature of the immune response induced by synthetic siRNA shares many of the hallmarks associated with TLR-mediated recognition of nucleic acids. These include the requirement for endosomal acidification (see, e.g., Diebold et al., Science 303, 1529-1531 (2004); Lund et al., *PNAS USA* 101, 5598-5603 (2004); Yi et al., *J. Immunol.* 160, 4755-4761 (1998); and Hacker et al., *Embo J.* 17, 6230-6240 (1998)) and the rapid activation of pDC to produce high levels of IFN-α. Human and murine pDC have been identified as the primary producers of IFN-α in response to CpG DNA (see, e.g., Hornung, et al., *J. Immunol.* 168, 4531-4537 (2002); Kadowaki et al., *J. Exp. Med.* 194, 863-869 (2001); and Asselin-Paturel et al., *J. Immunol.* 171, 6466-6477 (2003)) and ssRNA (see, e.g., Heil et al., *Science* 303, 1526-1529 (2004); Diebold et al., *Science* 303, 1529-1531 (2004); and Lund et al., *PNAS USA* 101, 5598-5603 (2004)) due to their selective expression of TLR9 and TLR7. ssRNA has also been demonstrated to activate human immune cells through TLR8 (see, e.g., Heil et al., *Science* 303, 1526-1529 (2004)) although this receptor is not considered to be expressed constitutively by human pDC (see, e.g., Hornung, et al., *J. Immunol.* 168, 4531-4537 (2002) and Kadowaki et al., *J. Exp. Med.* 194, 863-869 (2001)). Given the characteristics of the immune response to siRNA and the broad similarities in sequence requirements, we hypothesize that double-stranded RNA molecules such as siRNA, as well as ssRNA oligonucleotides, can also be a ligand for TLR7 within the endosomal compartment. This scenario would be analogous to the recognition of CpG motifs in the context of either single and double stranded DNA by TLR9 (see, e.g., Krieg, *Annu. Rev. Immunol.* 20, 709-760 (2002)). Confirmation of the molecular basis for siRNA recognition by the innate immune system will be of significant benefit in further understanding how such responses can be regulated by modifications of the siRNA duplex.

The potential for synthetic siRNA duplexes to be immunostimulatory must be taken into consideration when utilizing siRNA for in vivo applications. Our identification of putative immunostimulatory sequence motifs within siRNA provides a basis for the rational design of synthetic siRNA that avoid activation of the innate immune response and therefore minimize the potential for off target effects and immunotoxicities. Provided such responses can be regulated, it can also be envisioned that the stimulatory properties of an siRNA may be exploited therapeutically, for example in antiviral indications, where siRNA mediated viral suppression combined with the local induction of interferons may be considered beneficial.

Thus, these data demonstrate that siRNA molecules can be potent activators of innate immunity. Although the mechanism siRNA-mediated immune stimulation has not been completely elucidated, the experiments described herein implicate Toll-Like Receptors. These findings have significant implications for the clinical development of RNAi as a novel therapeutic approach and in the interpretation of specific gene silencing effects using siRNA.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Accession Nos. are incorporated herein by reference for all purposes.

What is claimed is:

1. A nucleic acid-lipid particle comprising:
(a) a modified siRNA comprising a double-stranded sequence of about 15 to about 30 nucleotides in length, said sequence comprising a non-immunostimulatory mismatch motif relative to an unmodified siRNA sequence that is capable of silencing expression of a target sequence, wherein the mismatch motif consists of a 5'-XX'-3' dinucleotide corresponding to a 5'-GU-3' dinucleotide in the sense or antisense strand of the unmodified siRNA sequence, wherein X and X' are independently selected from the group consisting of A, U, C, and G, with the proviso that if X is G, X' is not U and if X' is U, X is not G,
wherein the modified siRNA is less immunogenic than the unmodified siRNA sequence, and
wherein the modified siRNA is capable of silencing expression of the target sequence;
(b) a cationic lipid, wherein said cationic lipid is selected from the group consisting of 1,2-DiLinoleyloxy-N,N-dimethylaminopropane (DLinDMA), 1,2-Dilinolenyloxy-N,N-dimethylaminopropane (DLenDMA), and a mixture thereof;
(c) a non-cationic lipid; and
(d) a conjugated lipid that inhibits aggregation of particles.

2. The nucleic acid-lipid particle in accordance with claim 1, wherein the modified siRNA has reduced toxicity relative to an siRNA that is not in a nucleic acid-lipid particle.

3. The nucleic acid-lipid particle in accordance with claim 1, wherein said cationic lipid is DLinDMA.

4. The nucleic acid-lipid particle in accordance with claim 1, wherein said non-cationic lipid is a member selected from the group consisting of distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16O-monomethyl PE, 16-O-dimethyl PE, 18-1-trans PE, 1-stearoyl-2-oleoyl-phosphatidyethanolamine (SOPE), cholesterol, and a mixture thereof.

5. The nucleic acid-lipid particle in accordance with claim 1, wherein said non-cationic lipid is DSPC.

6. The nucleic acid-lipid particle in accordance with claim 1, wherein the conjugated lipid that inhibits aggregation of particles comprises a polyethyleneglycol (PEG)-lipid and the PEG-lipid is member selected from the group consisting of a PEG-diacylglycerol, a PEG dialkyloxypropyl, a PEG-phospholipid, a PEG-ceramide, and a mixture thereof.

7. The nucleic acid-lipid particle in accordance with claim 1, wherein the conjugated lipid that inhibits aggregation of particles comprises a PEG-dialkyloxypropyl (DAA) conjugate.

8. The nucleic acid-lipid particle in accordance with claim 7, wherein the PEG-DAA conjugate is a member selected from the group consisting of a PEG-dilauryloxypropyl ($C_{12}$), a PEG-dimyristyloxypropyl ($C_{14}$), a PEG-dipalmityloxypropyl ($C_{16}$), and a PEG-distearyloxypropyl ($C_{18}$).

9. The nucleic acid-lipid particle in accordance with claim 7, wherein the PEG-DAA conjugate is a PEG-dimyristyloxypropyl ($C_{14}$).

10. The nucleic acid-lipid particle in accordance with claim 1, wherein said cationic lipid comprises from about 15% to about 35% of the total lipid present in said particle.

11. The nucleic acid-lipid particle in accordance with claim 1, wherein said non-cationic lipid comprises from about 15% to about 25% of the total lipid present in said particle.

12. The nucleic acid-lipid particle in accordance with claim 7, wherein said PEG-DAA conjugate comprises from 1% to about 10% of the total lipid present in said particle.

13. The nucleic acid-lipid particle in accordance with claim 7, wherein said PEG-DAA conjugate comprises about 2% of the total lipid present in said particle.

14. The nucleic acid-lipid particle in accordance with claim 1, further comprising cholesterol.

15. The nucleic acid-lipid particle in accordance with claim 14, wherein the cholesterol comprises from about 40% to about 60% of the total lipid present in said particle.

16. The nucleic acid-lipid particle in accordance with claim 1, wherein the modified siRNA is fully encapsulated in said nucleic acid-lipid particle.

17. A composition comprising a nucleic acid-lipid particle in accordance with claim 1 and a carrier.

18. The nucleic acid-lipid particle in accordance with claim 1, wherein said cationic lipid comprises from about 2% to about 60% of the total lipid present in said particle.

19. The nucleic acid-lipid particle in accordance with claim 1, wherein said cationic lipid comprises from about 40% to about 50% of the total lipid present in said particle.

20. The nucleic acid-lipid particle in accordance with claim 1, wherein said non-cationic lipid comprises from about 5% to about 90% of the total lipid present in said particle.

21. The nucleic acid-lipid particle in accordance with claim 1, wherein said non-cationic lipid comprises from about 20% to about 85% of the total lipid present in said particle.

22. The nucleic acid-lipid particle in accordance with claim 14, wherein the cholesterol comprises from about 20% to about 45% of the total lipid present in said particle.

23. The nucleic acid-lipid particle in accordance with claim 1, wherein said particle has a median diameter of from about 50 nm to about 150 nm.

24. The nucleic acid-lipid particle in accordance with claim 1, wherein said non-cationic lipid comprises a phospholipid and cholesterol, and wherein said conjugated lipid that inhibits aggregation of particles comprises a PEG-DAA conjugate.

25. The nucleic acid-lipid particle in accordance with claim 1, wherein the modified siRNA further comprises a second non-immunostimulatory mismatch motif.

26. The nucleic acid-lipid particle in accordance with claim 1, wherein the modified siRNA comprises a double-stranded sequence of about 19 to about 25 nucleotides in length.

27. The nucleic acid-lipid particle in accordance with claim 1, wherein the modified siRNA comprises 3' overhangs.

28. The nucleic acid-lipid particle in accordance with claim 1, wherein said conjugated lipid that inhibits aggregation of particles comprises from about 1% to about 15% of the total lipid present in said particle.

* * * * *